United States Patent
Singer et al.

(10) Patent No.: US 11,781,173 B2
(45) Date of Patent: Oct. 10, 2023

(54) RNA TAGGING SYSTEM FOR VISUALIZATION OF SINGLE MRNA MOLECULES

(71) Applicant: ALBERT EINSTEIN COLLEGE OF MEDICINE, Bronx, NY (US)

(72) Inventors: Robert H. Singer, New York, NY (US); Evelina Tutucci, New York, NY (US); Maria Vera Ugalde, New York, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 513 days.

(21) Appl. No.: 16/606,046

(22) PCT Filed: Apr. 19, 2018

(86) PCT No.: PCT/US2018/028269
§ 371 (c)(1),
(2) Date: Oct. 17, 2019

(87) PCT Pub. No.: WO2018/195254
PCT Pub. Date: Oct. 25, 2018

(65) Prior Publication Data
US 2021/0139964 A1  May 13, 2021

Related U.S. Application Data

(60) Provisional application No. 62/487,058, filed on Apr. 19, 2017.

(51) Int. Cl.
*C07H 21/02* (2006.01)
*C12Q 1/6841* (2018.01)
*C12Q 1/6897* (2018.01)

(52) U.S. Cl.
CPC ......... *C12Q 1/6841* (2013.01); *C12Q 1/6897* (2013.01)

(58) Field of Classification Search
USPC .................. 435/6.1, 6.11, 91.1; 436/94, 501; 536/23.1, 24.3, 24.33
See application file for complete search history.

(56) References Cited

U.S. PATENT DOCUMENTS

| 6,203,986 B1 | 3/2001 | Singer et al. |
| 2010/0086917 A1 | 4/2010 | Haim et al. |
| 2011/0189674 A1* | 8/2011 | Tomigahara ......... C12Q 1/6834 436/501 |

OTHER PUBLICATIONS

1988 Stratagene Catalog, p. 39. Published by Stratgene, 11011 North Torrey Pines Road, La Jolla, CA 92037, USA.*
Mayr, What Are 3' UTRs Doing? Cold Spring Harb. Perspect. Biol., 11, a034728, 2019.*
Cleveland et al., Multiple determinants of eukaryotic mRNA stability. The New Biologist, 1, 121-126, 1989.*
PCT International Search Report and Written Opinion dated Aug. 1, 2018 for PCT International Patent Application No. PCT/US2018/028269.

(Continued)

*Primary Examiner* — Frank W Lu
(74) *Attorney, Agent, or Firm* — Foley Hoag LLP

(57) ABSTRACT

An RNA tagging system for visualization of single mRNA molecules based on a MSB-MCP system, as well as methods of use.

8 Claims, 17 Drawing Sheets

Specification includes a Sequence Listing.

(56) References Cited

OTHER PUBLICATIONS

Valegard et al., The Three-dimensional Structures of Two Complexes between Recombinant MS2 Capsids and RNA Operator Fragments Reveal Sequence-specific Protein-RNA Interactions. J. Mol. Biol. Aug. 1, 1997, vol. 270, No. 5, pp. 724-738. Espeically p. 726, Figure 2 legend; p. 735, col. 2, para 1.

Wu et al., Fluorescence Fluctuation Spectroscopy Enables Quantitative Imaging of Single mRNAs in Living Cells. Biophysical Journal, Jun. 20, 2012, vol. 102, No. 12, pp. 2936-2944. Espeically p. 2937, col. 1, para 2; p. 2938, col. 1, para 7.

Anke et al., A versatile toolbox for PCR-based tagging of yeast genes: new fluorescent proteins, more markers and promoter substitution cassettes. Yeast, Aug. 2004, vol. 21, No. 11, pp. 947-962. Espeically p. 955, col. 2, last para; p. 958, col. 1, para 2.

\* cited by examiner

US 11,781,173 B2

RNA TAGGING SYSTEM FOR VISUALIZATION OF SINGLE MRNA MOLECULES

CROSS-REFERENCE TO RELATED APPLICATIONS

This application is a U.S. national stage entry under 35 U.S.C. § 371 of PCT International Patent Application No. PCT/US2018/028269, filed Apr. 19, 2018, which claims benefit of U.S. Provisional Application No. 62/487,058, filed Apr. 19, 2017, the contents of each of which are incorporated herein by reference into the subject application.

STATEMENT OF GOVERNMENT SUPPORT

This invention was made with government support under grant number GM57071 awarded by the National Institutes of Health. The government has certain rights in the invention.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: the text file named "AET-02801_SL.txt", which was created on Jan. 23, 2023 and is 44,763 bytes in size.

BACKGROUND OF THE INVENTION

Throughout this application various publications are referred to. Full citations for the references may be found at the end of the specification. The disclosures of these publications are hereby incorporated by reference in their entirety into the subject application to more fully describe the art to which the subject invention pertains.

The ability to visualize single molecules in intact cells is a powerful tool to study gene expression quantitatively from transcription to translation with high temporal and spatial resolution (Vera et al., 2016). However, the last step of the mRNA life cycle, degradation, remained a challenging event to visualize in living cells at the single molecule level. Previous work from our lab used single molecule in situ hybridization (smFISH) to analyze the degradation of highly unstable mRNAs in yeast (Trcek et al., 2011). This work provided the first evidence that the promoter sequence of cell cycle regulated genes dictates when mRNAs decay in the cytoplasm. However, using fixed cells precludes determining single mRNA dynamics from transcription to degradation in a single cell. Hence, important information is missed about where mRNA degradation occurs in the cell and how variable this process is from cell to cell.

To report mRNA decay in living cells we used the available MS2-MCP system. This method utilizes RNA loops derived from the single-stranded RNA bacteriophage MS2. In the phage genome, the MS2 binding sites (MBS) and the MS2 coat protein homo-dimer (MCP) interact to control viral particle assembly (Bernardi and Spahr, 1972). For mRNA detection, 24 MBSs are inserted in the 3'UTR of an mRNA of interest and co-expression of MCP fused with fluorescent proteins renders single mRNAs visible using wide-field epi-fluorescence microscopy. This approach has been used to image and follow single mRNA molecules in living eukaryotic cells to study mRNA transcription, export, localization and translation (Bertrand et al., 1998; Fusco et al., 2003; Grunwald and Singer, 2010; Larson et al., 2011; Shav-Tal et al., 2004; Wu et al., 2016). However, the attempt to use the available MBS-MCP system to study mRNA decay of tagged mRNAs in S. cerevisiae revealed that mRNA degradation is impaired by MCP binding to MBS, which can inhibit the cytoplasmic exonuclease Xrn1 (Garcia and Parker, 2015, 2016). Consequently, a significant fraction of the signal observed using the MBS-MCP system is due to 3' decay fragments containing MS2 loops (Garcia and Parker, 2015; Heinrich et al., 2017). This degradation inhibition differs based on mRNA levels, whether the mRNA is expressed from a plasmid or from the endogenous locus and the intrinsic stability of the mRNA (Haimovich et al., 2016) and is enhanced in stress conditions, such as glucose starvation (Heinrich et al., 2017). Because the MBS system has been used to study various aspects of cytoplasmic mRNA regulation in living yeast (Sheth and Parker, 2003; Zid and O'Shea, 2014; Zipor et al., 2009), the uncertainty as to whether the MBS signal represents full-length mRNA raises the concern that the available MBS-MCP system can yield spurious results in S. cerevisiae.

The present invention addresses the need for a new method and system for visualization of single mRNA molecules.

SUMMARY OF THE INVENTION

A nucleic acid is provided encoding from twelve to twenty four loops of 5'-ANC/UA-3', (SEQ ID NO:1) wherein the 5' end of each loop is connected to a sequence of eight nucleotides, seven of which are complementary to a sequence of seven nucleotides connected to the 3' end of the same loop, such that a stem and loop structure is formed for each loop, and wherein a stem of each loop is separated from a stem of each adjacent loop by a nucleotide sequence of more than 39 nucleotides.

A nucleic acid is provided encoding from seven to twelve loops of 5'-ANC/UA-3', (SEQ ID NO:1) wherein the 5' end of each loop is connected to a sequence of eight nucleotides, seven of which are complementary to a sequence of seven nucleotides connected to the 3' end of the same loop, such that a stem and loop structure is formed for each loop, and wherein a stem of each loop is separated from a stem of each adjacent loop by a nucleotide sequence of more than 40 nucleotides.

In an embodiment, the nucleic acid comprises SEQ ID NO:2 or 3. In an embodiment, the nucleic acid comprises SEQ ID NO:2. In an embodiment, the nucleic acid comprises SEQ ID NO:3.

In an embodiment, the nucleic acid encodes from twelve to twenty four loops. In an embodiment, the nucleic acid encodes twelve loops. In an embodiment, the nucleic acid encodes twenty four loops.

Also provided is a nucleic acid encoding, in 5' to 3' order or 3' to 5' order:
(i) a CYC1 promoter;
(ii) a MS2 bacteriophage coat protein homo-dimer (MCP);
(iii) a first fluorescent protein;
(iv) a second fluorescent protein;
(v) a nuclear localization sequence (NLS);
(vi) a CYC1 terminator sequence.

Also provided is a nucleic acid encoding, in 5' to 3' order or 3' to 5' order:
(i) a CYC1 promoter;
(ii) a MS2 bacteriophage coat protein homo-dimer (MCP);
(iii) a nuclear localization sequence (NLS);
(iv) a first fluorescent protein;

(v) a second fluorescent protein;
(vi) a CYC1 terminator sequence.

In an embodiment, the nucleic acid comprises SEQ ID NO:4 or 32. In an embodiment, the nucleic acid comprises SEQ ID NO:4. In an embodiment, the nucleic acid comprises SEQ ID NO:32.

A kit is provided comprising two plasmids, (1) and (2), wherein:
(1) encodes from seven to twenty four loops of 5'-ANC/UA-3'(SEQ ID NO:1), each wherein the 5' end of each loop is connected to a sequence of eight nucleotides, seven of which nucleotides complementary to a sequence of seven nucleotides connected to the 3' end of the same loop, such that a stem and loop structure is formed for each loop, and wherein each loop is separated from each adjacent loop by a nucleotide sequence of 40-55 nucleotides, and
(2) encodes, in 5' to 3' order or 3' to 5' order:
(A) (i) a CYC1 promoter;
(ii) a MS2 bacteriophage coat protein homo-dimer (MCP);
(iii) a nuclear localization sequence (NLS);
(iv) a first fluorescent protein;
(v) a second fluorescent protein;
(vi) a CYC1 terminator sequence, or
(B) (i) a CYC1 promoter;
(ii) a MS2 bacteriophage coat protein homo-dimer (MCP);
(iii) a nuclear localization sequence (NLS);
(iv) a first fluorescent protein;
(v) a second fluorescent protein;
(vi) a CYC1 terminator sequence; and
(3) instructions for use in visualizing an RNA of interest in a eukaryotic cell.

A kit is provided comprising two plasmids, (i) and (ii), wherein:
(i) encodes from seven to twelve loops of 5'-ANC/UA-3' (SEQ ID NO:1), each wherein the 5' end of each loop is connected to a sequence of eight nucleotides, seven of which nucleotides complementary to a sequence of seven nucleotides connected to the 3' end of the same loop, such that a stem and loop structure is formed for each loop, and wherein each loop is separated from each adjacent loop by a nucleotide sequence of 45-55 nucleotides, and
(ii) encodes, in 5' to 3' order or 3' to 5' order:
(i) a CYC1 promoter;
(ii) a MS2 bacteriophage coat protein homo-dimer (MCP);
(iii) a nuclear localization sequence (NLS);
(iv) a first fluorescent protein;
(v) a second fluorescent protein;
(vi) a CYC1 terminator sequence, and
(iii) instructions for use in visualizing an RNA of interest in a eukaryotic cell.

Also provided is a method of detecting or of monitoring an RNA of interest in a yeast cell, the method comprising:
(i) inserting in a cell the nucleic acid, encoding from twelve to twenty four loops of 5'-ANC/UA-3', as described herein into the 3'-UTR of a gene encoding the RNA of interest by homologous recombination and using Cre-Lox recombination so as to remove a marker gene so as to tag the RNA of interest with the twelve to twenty four loops;
(ii) transfecting the cell with a nucleic acid, encoding an MCP, as described herein so as to permit expression of a fusion protein comprising the MCP, NLS and the first and second fluorescent proteins
(iii) detecting or monitoring the movement and/or location of a fluorescent signal of the first and second fluorescent proteins so as to detect or monitor the RNA of interest.

Also provided is a method of detecting or of monitoring an RNA of interest in a yeast cell, the method comprising:
(i) inserting in a cell the nucleic acid, encoding from seven to twelve four loops of 5'-ANC/UA-3', as described herein into the 3'-UTR of a gene encoding the RNA of interest by homologous recombination and using Cre-Lox recombination so as to remove a marker gene so as to tag the RNA of interest with the seven to twelve four loops;
(ii) transfecting the cell with a nucleic acid, encoding an MCP, as described herein so as to permit expression of a fusion protein comprising the MCP, NLS and the first and second fluorescent proteins
(iii) detecting or monitoring the movement and/or location of a fluorescent signal of the first and second fluorescent proteins so as to detect or monitor the RNA of interest.

Also provided is a method of detecting or of monitoring an RNA of interest in a yeast cell, the method comprising:
(i) inserting in a cell the nucleic acid, encoding from twelve to twenty four loops of 5'-ANC/UA-3', as described herein into the 3'-UTR of a gene encoding the RNA of interest by homologous recombination and using Cre-Lox recombination so as to remove a marker gene so as to tag the RNA of interest with the twelve to twenty four loops;
(ii) transfecting the cell with a nucleic acid, encoding an MCP, as described herein so as to permit expression of a fusion protein comprising the MCP, NLS and the first and second fluorescent proteins
(iii) detecting or monitoring the movement and/or location of a fluorescent signal of the first and second fluorescent proteins so as to detect or monitor the RNA of interest.

Also provided is a method of detecting or of monitoring an RNA of interest in a yeast cell, the method comprising:
(i) inserting in a cell the nucleic acid, encoding from seven to twelve loops of 5'-ANC/UA-3', as described herein into the 3'-UTR of a gene encoding the RNA of interest by homologous recombination and using Cre-Lox recombination so as to remove a marker gene so as to tag the RNA of interest with the seven to twelve loops;
(ii) transfecting the cell with a nucleic acid, encoding an MCP, as described herein so as to permit expression of a fusion protein comprising the MCP, NLS and the first and second fluorescent proteins
(iii) detecting or monitoring the movement and/or location of a fluorescent signal of the first and second fluorescent proteins so as to detect or monitor the RNA of interest.

Also provided is a method of detecting or monitoring an RNA of interest in a eukaryotic cell, the method comprising:
(i) transfecting the eukaryotic cell with a plasmid or RNA that has been in vitro modified to encode from twelve to twenty four loops of 5'-ANC/UA-3', as described herein, into the 3'-UTR of a gene encoding the RNA of interest
(ii) transfecting the cell with a nucleic acid encoding a MS2 bacteriophage coat protein homo-dimer (MCP) and a fluorescent protein;
(iii) detecting or monitoring the movement and/or location of a fluorescent signal of the first and second fluorescent proteins so as to detect or monitor the RNA of interest.

Also provided is a method of detecting or of monitoring an RNA of interest in a eukaryotic cell, the method comprising:
(i) transfecting the eukaryotic cell with a plasmid or RNA that has been in vitro modified to encode from seven to twelve loops of 5'-ANC/UA-3', as described herein, into the 3'-UTR of a gene encoding the RNA of interest
(ii) transfecting the cell with a nucleic acid encoding a MS2 bacteriophage coat protein homo-dimer (MCP) and a fluorescent protein;

(iii) detecting or monitoring the movement and/or location of a fluorescent signal of the first and second fluorescent proteins so as to detect or monitor the RNA of interest.

Additional objects of the invention will be apparent from the description which follows.

BRIEF DESCRIPTION OF THE DRAWINGS

FIG. 2A shows ACAUCAC-CAUUACCCAUCU (SEQ ID NO: 33). (B) MBSORF loops are dimers of 2 different loop sequences distanced by 20 nts repeated every 50 nts. MBSORF is C-variant (cytosine at position −5). The stem loop is 7 nts long. (C) MBSV5 loops have non repeated sequences and 30 nt linkers with stem loops of 9 nts. All loops are C-variant. (D) RNA loop sequences used for EMSA assays. MBS is the original MS2 bacteriophage sequence (MBS shows ACAUGAGGAU-CACCCAUGU (SEQ ID NO: 34) or ACAUGAG-GAUUACCCAUGU (SEQ ID NO: 35). Loops 1 and 2 have randomized stem sequence of 7 nts (Loop1 shows GACGCAGGACCACCGCGUC (SEQ ID NO: 36) or GACGCAGGACUACCGCGUC (SEQ ID NO: 37) (Loop2: CGCAGAGGAACACCCUGCG (SEQ ID NO: 38) or CGCAGAGGAAUACCCUGCG (SEQ ID NO: 39). The three loops were generated either as a wt (U) or C variants (C). The affinity of MCP for the six loops was tested by EMSA. (E-G) Binding affinity of MCP for the MBS C-variants and wt-variants. Plot of the fraction of RNA bound as a function of MCP concentration and its fit to the Hill equation. The Kd from three independent measurements is indicated on the plots for (E) the original MBS sequence, (F) the Loop1 and (G) the Loop2, either wt or C-variant. (H and I) Schematic representation of new MBS systems. MBSV6 and MBSV7 have a randomized sequence of twelve stem loops and linkers. The length of the stem is 7 nts and the linkers are 50 nt (MBSV6, H) or 40 nts (MBSV7, I). MBSV6 and MBSV7 were synthetized in two versions: C-variant (12 loops with C) or a wt-variant (12 loops with U). (J-K) Image of living cells co-expressing MCP. (J) ASH1 24×MBSV6 C variant (left) or MDN1 24×MBSV7 C variant (right). (K) ASH1 24×MBSV6 wt-variant (left) or MDN1 24×MBSV7 wt-variant (right). Yellow arrows indicate MBS aggregates. White arrows indicate single mRNAs.

DETAILED DESCRIPTION OF THE INVENTION

Figure 1A:
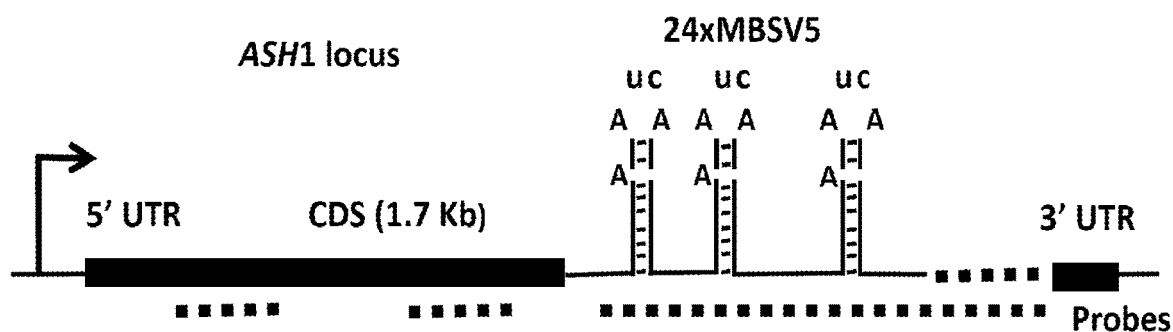
FIG. 1A-1H: Current MBS systems resist degradation in yeast. (A and B) Scheme of ASH1 and MDN1 loci tagged currently used MBS (A) Schematic representation of 24×MBSV5 inserted in the 3'UTR of endogenous ASH1 gene. All loops have a different stem sequence to avoid recombination. Purple boxes represent the localization sequences of ASH1 mRNA. (B) Schematic representation of 24×MBSORF inserted in the 3'UTR of the endogenous MDN1 gene. Loops have no STOP codons in the 3 frames to avoid NMD. (A and B) Dotted lines designate smFISH probe positions recognizing the CDS (green) or MBS sequences (red). (C and D) Two color smFISH for tagged mRNAs (C) ASH1 mRNA tagged with 24×MBSV5 and (D) MDN1 tagged with 24×MBSORF, in cells expressing MCP (YcpLac111 CYC1p-MCP-NLS-2xyeGFP) or the vector alone (YcpLac111). (C) DIC/MERGE shows the overlap of the DAPI signal in the nucleus (blue), smFISH for the ASH1 CDS (green) and the MBS (red) with the differential interference contrast (DIC) image. (D) MERGE shows the overlap of the DAPI (blue), smFISH for the MDN1 CDS (green) and the MBS (red). Yellow lines define the shape of a single cell and the corresponding cell cycle stage. Arrows designate single mRNAs. Scale bar=5 μm. TS=transcription site. (E and F) Quantification of smFISH represented in 1C and 1D with CDS probes (green plots) or MBS probes (red) reported as frequency distribution of mature ASH1 (E) and MDN1 (F) mRNAs per cell. Mean and SD of two biological replicates, n=~500 cells per experiment. (G) MBS aggregates in the cytoplasm detected as bright fluorescent spots by smFISH. Merge shows the overlap of the DAPI (blue), smFISH for the CDS (green, for either ASH1 or MDN1) and the MBS (red, for MBSV5 or MBSORF) in cells co-expressing MCP. MBS aggregates (arrows) are not detected with CDS probes. The percentage indicates cells positive for MBS aggregates. Scale bar=5 μm (H) MBS aggregates in live cells detected in the cytoplasm of living cells co-expressing MCP. Single ASH1 (left) and MDN1 (right) mRNAs are visualized as discrete GFP dots in the cytoplasm (white arrows). MBS aggregates are visualized as GFP dots brighter than single mRNAs (yellow arrows).

To address this problem of spurious MBS-MCP system signals, the inventors designed a new MBS system that mimics the actual regulation of the endogenous untagged mRNA in eukaryotic cells.

A nucleic acid is provided encoding from twelve to twenty four loops of 5'-ANC/UA-3', (SEQ ID NO:1) wherein the 5' end of each loop is connected to a sequence of eight nucleotides, seven of which are complementary to a sequence of seven nucleotides connected to the 3' end of the same loop, such that a stem and loop structure is formed for each loop, and wherein a stem of each loop is separated from a stem of each adjacent loop by a nucleotide sequence of more than 39 nucleotides.

A nucleic acid is provided encoding from seven to twelve loops of 5'-ANC/UA-3', (SEQ ID NO:1) wherein the 5' end of each loop is connected to a sequence of eight nucleotides, seven of which are complementary to a sequence of seven nucleotides connected to the 3' end of the same loop, such that a stem and loop structure is formed for each loop, and wherein a stem of each loop is separated from a stem of each adjacent loop by a nucleotide sequence of more than 40 nucleotides.

In an embodiment, a stem of each loop is separated from a stem of each adjacent loop by a nucleotide sequence of 40-55 nucleotides. In an embodiment, a stem of each loop is separated from a stem of each adjacent loop by a nucleotide sequence of 41-60 nucleotides. In an embodiment, a stem of each loop is separated from a stem of each adjacent loop by a nucleotide sequence of 45-55 nucleotides. In an embodiment, a stem of each loop is separated from a stem of each adjacent loop by a nucleotide sequence of 50 nucleotides.

In an embodiment, the nucleotide of the eight nucleotides that is not complementary to the seven nucleotides connected to the 3' end of the loop is an unpaired purine. In an embodiment, the unpaired purine is an A. In an embodiment, the nucleotide of the eight nucleotides that is not complementary to the seven nucleotides connected to the 3' end of the loop is the third nucleotide of the sequence of eight nucleotides as counted from the 5' end of the '-ANC/UA-3' loop. In an embodiment, the first two nucleotides of the sequence of eight nucleotides as counted from the 5' end of the '-ANC/UA-3' loop are, respectively, complementary to the first two nucleotides of the sequence of seven nucleotides as counted from the 3' end of the '-ANC/UA-3' loop.

In an embodiment, the fourth to eighth nucleotides of the sequence of eight nucleotides as counted from the 5' end of the '-ANC/UA-3' loop are, respectively, complementary to the third to seventh nucleotides, respectively, of the sequence of seven nucleotides as counted from the 3' end of the '-ANC/UA-3' loop.

In an embodiment, N in the sequence ANC/UA is any nucleotide or ribonucleotide. In an embodiment, N is A. In an embodiment, N is U. In an embodiment, N is C. In an embodiment, N is G.

In an embodiment, the nucleic acid, at a 3' portion thereof, further comprises a two LoxP sites, optionally separated by a marker gene. In an embodiment, the marker gene is a kanamycin resistance gene.

In an embodiment, the nucleic acid encodes twelve loops of 5'-ANC/UA-3'.

In an embodiment, each loop stem is separated from each adjacent loop stem by a nucleotide sequence of 50 nucleotides.

In an embodiment, the stem of the stem and loop structure for each of the loops has a different sequence than the stems of the stem and loop structure for all of the remaining loops.

In an embodiment, the stem of the stem and loop structure for each of the loops has the same sequence than the stems of the stem and loop structure for all of the remaining loops.

In an embodiment, the loops encoded by the nucleic acid all have the sequence 5'-ANUA-3'.

In an embodiment, the loops encoded by the nucleic acid all have the sequence 5'-ANCA-3'.

In an embodiment, the nucleic acid comprises SEQ ID NO:2 or 3. In an embodiment, the nucleic acid comprises SEQ ID NO:2. In an embodiment, the nucleic acid comprises SEQ ID NO:3.

In an embodiment, the nucleic acid encodes from twelve to twenty four loops. In an embodiment, the nucleic acid encodes twelve loops. In an embodiment, the nucleic acid encodes twenty four loops.

Also provided is a nucleic acid encoding, in 5' to 3' order or 3' to 5' order:
(i) a CYC1 promoter;
(ii) a MS2 bacteriophage coat protein homo-dimer (MCP);
(iii) a first fluorescent protein;
(iv) a second fluorescent protein;
(v) a nuclear localization sequence (NLS);
(vi) a CYC1 terminator sequence.

Also provided is a nucleic acid encoding, in 5' to 3' order or 3' to 5' order:
(i) a CYC1 promoter;
(ii) a MS2 bacteriophage coat protein homo-dimer (MCP);
(iii) a nuclear localization sequence (NLS);
(iv) a first fluorescent protein;
(v) a second fluorescent protein;
(vi) a CYC1 terminator sequence.

In an embodiment, the nucleic acid comprises SEQ ID NO:4 or 32. In an embodiment, the nucleic acid comprises SEQ ID NO:4. In an embodiment, the nucleic acid comprises SEQ ID NO:32.

In an embodiment, the nucleic acid encodes (i) through (iv) in 5' to 3' order.

In an embodiment, the first fluorescent protein and second fluorescent protein have the same amino acid sequence.

In an embodiment, the first fluorescent protein and second fluorescent protein are a GFP or a tdTomato.

In an embodiment, the first fluorescent protein and second fluorescent protein are eGFP.

A kit is provided comprising two plasmids, (1) and (2), wherein:
(1) encodes from seven to twenty four loops of 5'-ANC/UA-3'(SEQ ID NO:1), each wherein the 5' end of each loop is connected to a sequence of eight nucleotides, seven of which nucleotides complementary to a sequence of seven nucleotides connected to the 3' end of the same loop, such that a stem and loop structure is formed for each loop, and wherein each loop is separated from each adjacent loop by a nucleotide sequence of 40-55 nucleotides, and
(2) encodes, in 5' to 3' order or 3' to 5' order:
(A) (i) a CYC1 promoter;
(ii) a MS2 bacteriophage coat protein homo-dimer (MCP);
(iii) a nuclear localization sequence (NLS);
(iv) a first fluorescent protein;
(v) a second fluorescent protein;
(vi) a CYC1 terminator sequence, or
(B) (i) a CYC1 promoter;
(ii) a MS2 bacteriophage coat protein homo-dimer (MCP);
(iii) a nuclear localization sequence (NLS);
(iv) a first fluorescent protein;
(v) a second fluorescent protein;
(vi) a CYC1 terminator sequence; and
(3) instructions for use in visualizing an RNA of interest in a eukaryotic cell.

Exemplary plasmid sequences are set forth in SEQ ID NOS:2, 3, 4 and 32. In embodiments, (1) is SEQ ID NO:2 or 3. In embodiments, (2) is SEQ ID NO:4 or 32.

A kit is provided comprising two plasmids, (i) and (ii), wherein:
(a) encodes from seven to twelve loops of 5'-ANC/UA-3' (SEQ ID NO:1), each wherein the 5' end of each loop is connected to a sequence of eight nucleotides, seven of which nucleotides complementary to a sequence of seven nucleotides connected to the 3' end of the same loop, such that a stem and loop structure is formed for each loop, and wherein each loop is separated from each adjacent loop by a nucleotide sequence of 45-55 nucleotides, and
(b) encodes, in 5' to 3' order or 3' to 5' order:
(i) a CYC1 promoter;
(ii) a MS2 bacteriophage coat protein homo-dimer (MCP);
(iii) a nuclear localization sequence (NLS);
(iv) a first fluorescent protein;
(v) a second fluorescent protein;
(vi) a CYC1 terminator sequence, and
(iii) instructions for use in visualizing an RNA of interest in a eukaryotic cell.

Exemplary sequences of (a) and (b) are set forth in SEQ ID NOS:2, 3, 4 and 32. In embodiments, (a) is SEQ ID NO:2 or 3. In embodiments, (b) is SEQ ID NO:4 or 32.

Also provided is a method of detecting or of monitoring an RNA of interest in a yeast cell, the method comprising:
(i) inserting in a cell the nucleic acid, encoding from twelve to twenty four loops of 5'-ANC/UA-3', as described herein into the 3'-UTR of a gene encoding the RNA of interest by homologous recombination and using Cre-Lox recombination so as to remove a marker gene so as to tag the RNA of interest with the twelve to twenty four loops; (ii) transfecting the cell with a nucleic acid, encoding an MCP, as described herein so as to permit expression of a fusion protein comprising the MCP, NLS and the first and second fluorescent proteins
(iii) detecting or monitoring the movement and/or location of a fluorescent signal of the first and second fluorescent proteins so as to detect or monitor the RNA of interest.

Also provided is a method of detecting or of monitoring an RNA of interest in a yeast cell, the method comprising:
(i) inserting in a cell the nucleic acid, encoding from seven to twelve four loops of 5'-ANC/UA-3', as described herein into the 3'-UTR of a gene encoding the RNA of interest by homologous recombination and using Cre-Lox recombination so as to remove a marker gene so as to tag the RNA of interest with the seven to twelve four loops;
(ii) transfecting the cell with a nucleic acid, encoding an MCP, as described herein so as to permit expression of a fusion protein comprising the MCP, NLS and the first and second fluorescent proteins
(iii) detecting or monitoring the movement and/or location of a fluorescent signal of the first and second fluorescent proteins so as to detect or monitor the RNA of interest.

Also provided is a method of detecting or of monitoring an RNA of interest in a yeast cell, the method comprising:
(i) inserting in a cell the nucleic acid, encoding from twelve to twenty four loops of 5'-ANC/UA-3', as described herein into the 3'-UTR of a gene encoding the RNA of interest by homologous recombination and using Cre-Lox recombination so as to remove a marker gene so as to tag the RNA of interest with the twelve to twenty four loops;
(ii) transfecting the cell with a nucleic acid, encoding an MCP, as described herein so as to permit expression of a fusion protein comprising the MCP, NLS and the first and second fluorescent proteins
(iii) detecting or monitoring the movement and/or location of a fluorescent signal of the first and second fluorescent proteins so as to detect or monitor the RNA of interest.

Also provided is a method of detecting or of monitoring an RNA of interest in a yeast cell, the method comprising:
(i) inserting in a cell the nucleic acid, encoding from seven to twelve loops of 5'-ANC/UA-3', as described herein into the 3'-UTR of a gene encoding the RNA of interest by homologous recombination and using Cre-Lox recombination so as to remove a marker gene so as to tag the RNA of interest with the seven to twelve loops;
(ii) transfecting the cell with a nucleic acid, encoding an MCP, as described herein so as to permit expression of a fusion protein comprising the MCP, NLS and the first and second fluorescent proteins
(iii) detecting or monitoring the movement and/or location of a fluorescent signal of the first and second fluorescent proteins so as to detect or monitor the RNA of interest.

Also provided is a method of detecting or of monitoring an RNA of interest in a eukaryotic cell, the method comprising:
(i) transfecting the eukaryotic cell with a plasmid or RNA that has been in vitro modified to encode from twelve to twenty four loops of 5'-ANC/UA-3', as described herein, into the 3'-UTR of a gene encoding the RNA of interest
(ii) transfecting the cell with a nucleic acid encoding a MS2 bacteriophage coat protein homo-dimer (MCP) and a fluorescent protein;
(iii) detecting or monitoring the movement and/or location of a fluorescent signal of the first and second fluorescent proteins so as to detect or monitor the RNA of interest.

Also provided is a method of detecting or of monitoring an RNA of interest in a eukaryotic cell, the method comprising:
(i) transfecting the eukaryotic cell with a plasmid or RNA that has been in vitro modified to encode from seven to twelve loops of 5'-ANC/UA-3', as described herein, into the 3'-UTR of a gene encoding the RNA of interest
(ii) transfecting the cell with a nucleic acid encoding a MS2 bacteriophage coat protein homo-dimer (MCP) and a fluorescent protein;

(iii) detecting or monitoring the movement and/or location of a fluorescent signal of the first and second fluorescent proteins so as to detect or monitor the RNA of interest.

In an embodiment, the nucleic acid encoding a MS2 bacteriophage coat protein homo-dimer (MCP) and a fluorescent protein is that described in (Wu, B et al, 2012).

In an embodiment, the eukaryotic cell is a mammalian cell. In an embodiment, the cell is a yeast cell. In an embodiment, in (i) the nucleic acid is inserted in the cell by way of a plasmid. In an embodiment, in (ii) the nucleic acid is transfected into the cell by way of a plasmid. In an embodiment, the fluorescent signal is monitored or detected by way of epifluorescence microscopy.

In an embodiment, in yeast cells (i) the nucleic acid is inserted in the cell by way of a PCR product or digested plasmid. In an embodiment, in (ii) the nucleic acid is transfected into the cell by way of a plasmid. In an embodiment, (iii) the fluorescent signal is monitored or detected by way of epifluorescence microscopy. In an embodiment, in mammalian cells (i) the nucleic acid is transfected in the cell by plasmid or RNA. In an embodiment, in (ii) the nucleic acid is transfected into the cell by way of a plasmid. In an embodiment, (iii) the fluorescent signal is monitored or detected by way of epifluorescence microscopy.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

Experimental Details

To address this problem of spurious MBS-MCP system signals, the inventors designed a new MBS system that mimics the actual regulation of the endogenous untagged mRNA in eukaryotic cells by inhibition elicited by previous MBS versions, and then by engineering a novel MBS-MCP system that overcame the limitations. To minimize variability and preserve the original regulatory sequences, all MBS versions were tested by tagging the mRNAs at the endogenous loci. The system disclosed herein differs from previous systems by: (i) the controlled low expression of the MCP fused to a fluorescent protein, (ii) the reduced affinity of MBSV6 for MCP, (iii) the increased distance between MS2 loops, and (iv) reduction of the number of loops from 24 to 12 to facilitate degradation. Because MBSV6 decays with the same kinetics of the tagged mRNA, these modifications made the new MBS-MCP system an accurate reporter to image mRNAs from transcription to degradation. Finally, the inventors challenged this new MBS by following single mRNA decay for the highly unstable mRNAs, GAL1 and ASH1, and obtained successful results.

Figure 1B:
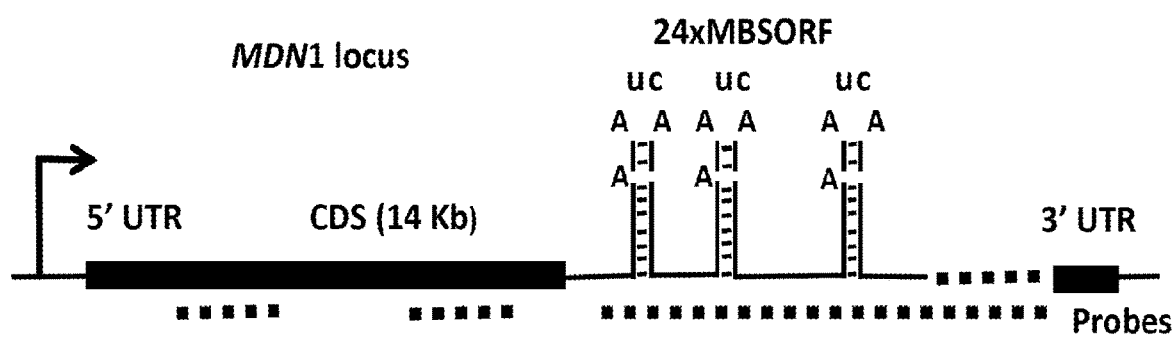

Characterization of the expression of mRNAs tagged with the MBS-MCP system: Previous studies indicating that the MBS-MCP system affected the degradation of tagged mRNAs used semi-quantitative ensemble approaches to assess this issue (eg. northern blot). To extend this analysis, we used two color smFISH to measure whether MBS-MCP tagged mRNAs accumulate 3' decay fragments in *S. cerevisiae*. Two-color smFISH has several advantages over the northern blot approach i) RNA degradation is minimized because cells are intact ii) the integrity of the full length mRNA can be assessed at the single molecule level iii) the mRNA localization can be resolved and iv) cell-to-cell variation can be quantified. Two well characterized genes were analyzed: ASH1, a cell cycle regulated mRNA with a rapid turnover that localizes to the bud tip (Bertrand et al., 1998; Long et al., 1997b), and MDN1, a constitutively expressed mRNA (Hocine et al., 2013; Zenklusen et al., 2008). Both genes were endogenously tagged with 24×MBS in the 3'UTR. The most recent MBS version, MBSV5, contains non-repetitive stem loops (to avoid recombination) was used for ASH1 (Wu et al., 2015); FIG. 1A) and a previous version MBSORF that contains repetitive stem loops without stop codons (to avoid NMD) was used for MDN1 ((Hocine et al., 2013); FIG. 1B). Cells expressed the MCP fused to two GFP molecules from the constitutive Cytochrome C1 promoter (CYC1p) (Mumberg et al., 1995), which guaranteed an homogenous expression among cells. The addition of a nuclear localization signal to the MCP reduced the cytoplasmic background during live imaging (CYC1p-MCP-NLS-2×GFP, hereafter MCP).

Figure 1C:
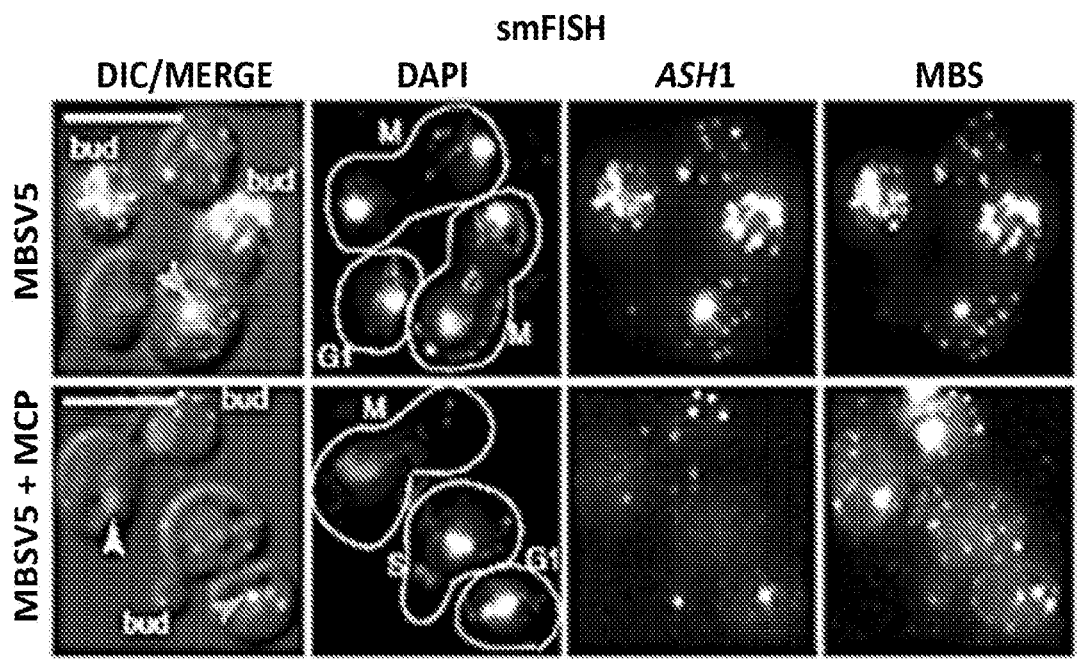
Figure 1D:
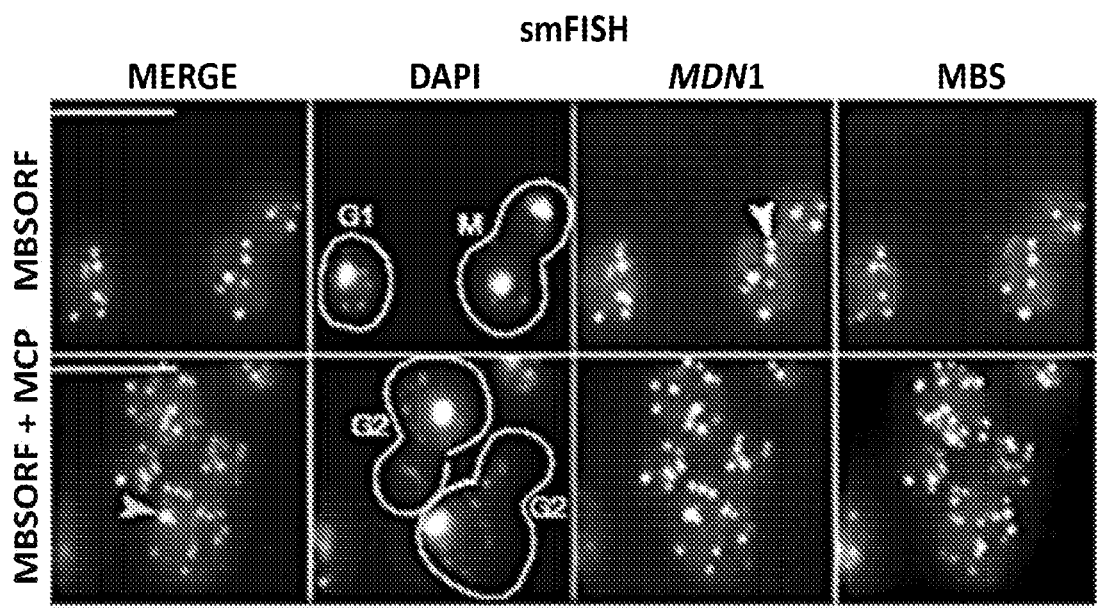
Figure 1E:
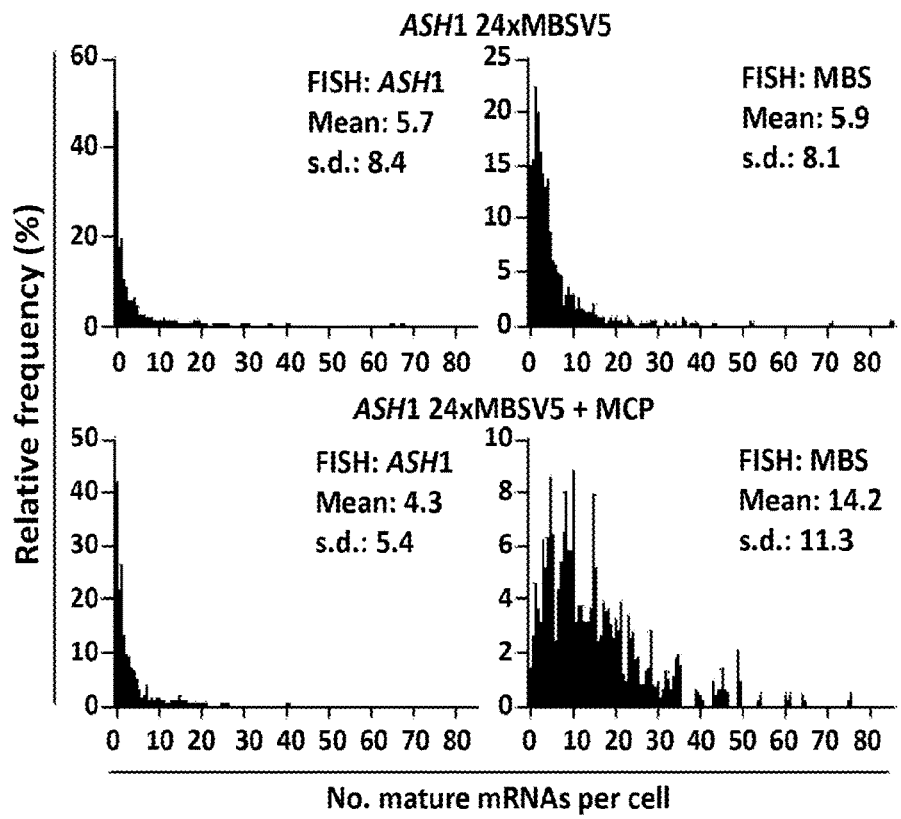
Figure 1F:
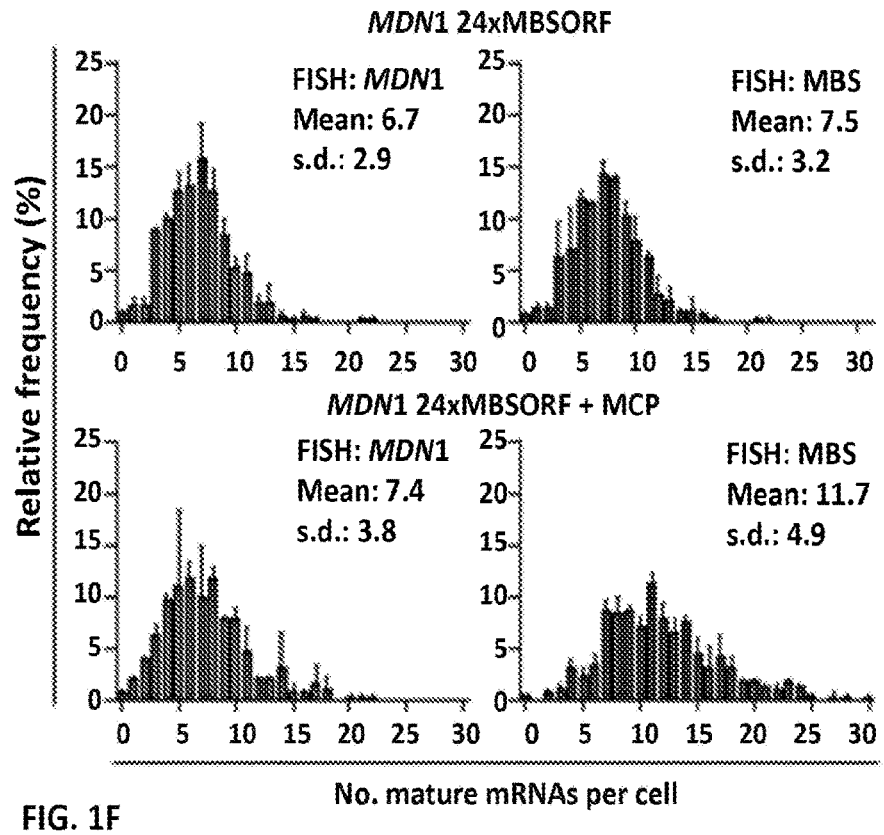

The mRNA integrity was probed by two color smFISH simultaneously recognizing the coding sequence, CDS, (ASH1 or MDN1) or the MBS sequence (MBSV5 or MBSORF) of the same mRNA (FIG. 1A-B). In an asynchronous population of cells, ASH1 mRNAs endogenously tagged with 24×MBSV5 properly localized to the bud tip during mitosis (FIG. 1C, top panels). Quantification using CDS probes showed similar expression level whether tagged or not, with or without MCP. However, in cells expressing MCP, two color smFISH showed an increased number of MBS molecules, without corresponding signal for ASH1 CDS, demonstrating an accumulation of 3' decay fragments (FIGS. 1C and 1E). The number of MBS fragments varied among cells and was, on average, 2.3 times higher than the full length ASH1 mRNA (FIG. 1E). We obtained similar results for MDN1 mRNAs tagged with 24×MBSORF. The expression of endogenous MDN1 is constitutive with a Gaussian distribution that ranges from 0 to ~15 mRNAs per cell (Zenklusen et al., 2008). However, the number of MBS doubled in the presence of the MCP relative to the mRNAs quantified with the CDS probes (FIGS. 1D and 1F).

Figure 1G:
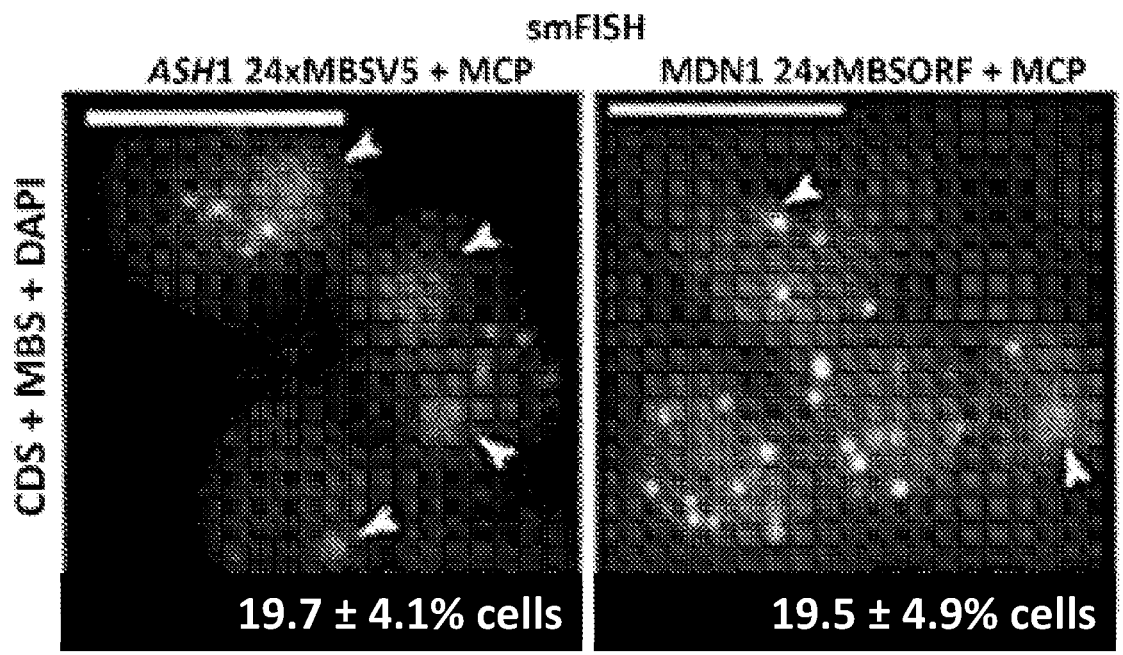

In about 20% of both ASH1 and MDN1 tagged yeast strains expressing MCP, bright aggregates were seen containing only the MBS sequence that did not hybridize to the CDS probes (FIG. 1G). These MBS aggregates resulted from the accumulation of single MBS sequences protected from degradation by MCP. Strains not expressing MCP showed a strong correlation between the number of single mRNAs quantified with the CDS probes or MBS probes (Pearson coefficient for ASH1 r=0.91, MDN1 r=0.76) that was reduced in strains expressing MCP (ASH1 r=0.56, MDN1 r=0.23). This resistance to degradation was underestimated because cells with MBS aggregates were not included in the analysis since the fluorescent signal was saturated impeding the quantification. Moreover, reducing the number of MBSV5 to twelve did not improve the degradation defect as observed by ASH1 and MBS smFISH.

Figure 1H:
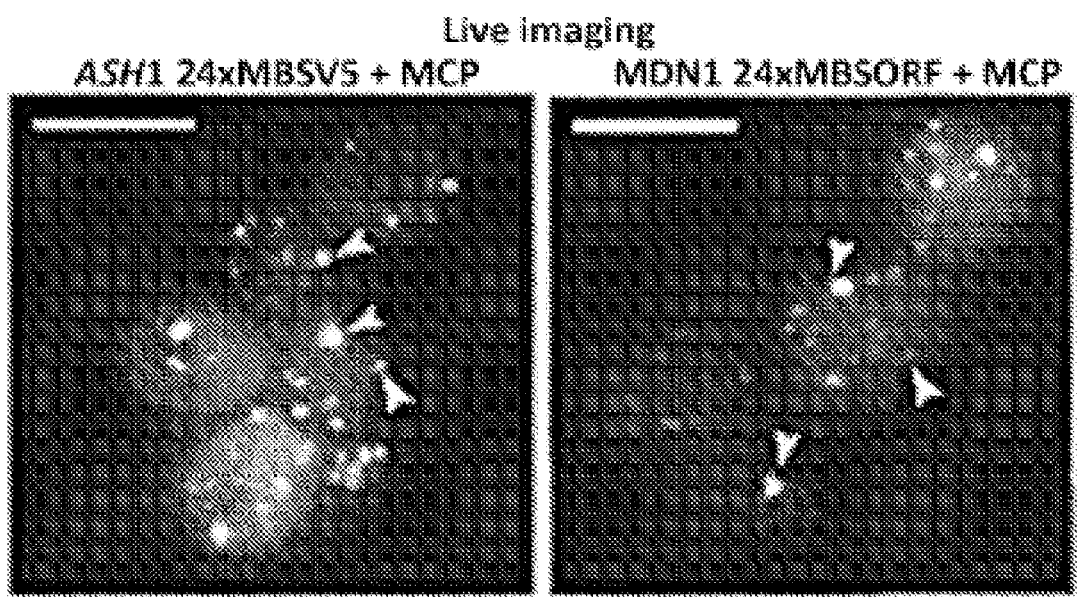

Live imaging was consistent with the smFISH results. Strains expressing MCP with tagged ASH1 or MDN1 revealed that 20% of the cells contained MBS aggregates that were less mobile and brighter than single molecules (FIG. 1H). These aggregates were not only MCP because they required an MBS-tagged mRNA. ASH1 MBS fragments were found in all cells, regardless of the cell cycle phase, demonstrating that degradation was dysregulated. Hence, the use of the available MBS-MCP systems in living yeast can lead to false conclusions about mRNA expression and localization and mRNA tagging should be validated using two color smFISH experiments. These observations suggested that the tight binding between the MCP and MBS may block the access of the cytoplasmic exonuclease Xm1, to the RNA (Garcia and Parker, 2015, 2016; Haimovich et al., 2016). Consequently, the kinetics of MBS fragment degradation would be slower than that of the CDS, leading to the formation of single MBS fragments that accumulate as aggregates. Consistent with the hypothesis that MBS aggregates form because of an mRNA degradation defect, only full-length ASH1 mRNAs but not MBS fragments localized to the bud tip, suggesting that the binding of the MCP to the MBS allows proper expression and localization of ASH1 mRNA but delays the degradation of the MBS sequence. The severity of the phenotype is aggravated for highly regulated and short-lived mRNAs, like ASH1, compared to constitutively expressed genes like MDN1. To overcome this problem, we designed degradable MBS versions.

Figure 2A:
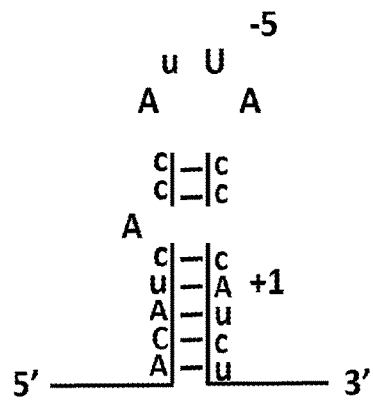
FIG. 2A-2K: Design and characterization of a new MBS-MCP system (A-C) Schematic representation of current MBS systems. (A) MBS wt sequence from the bacteriophage MS2. Nucleotide positions are relative to the translation start codon AUG (+1).
Figure 2B:
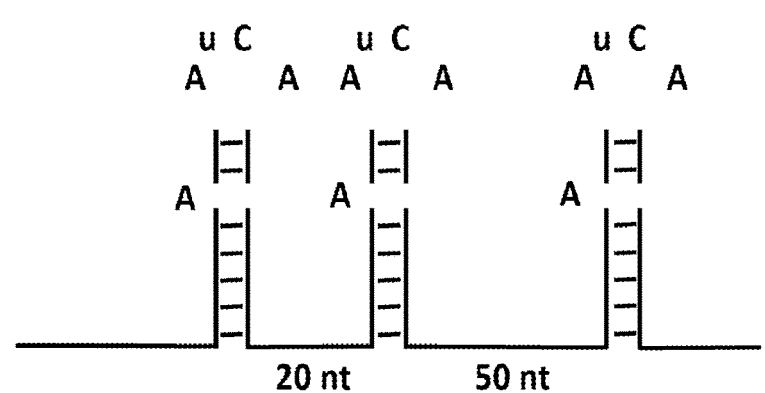
Figure 2C:
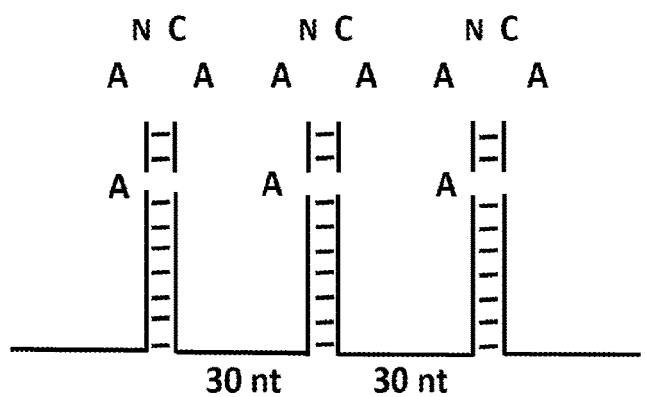
Figure 2D:
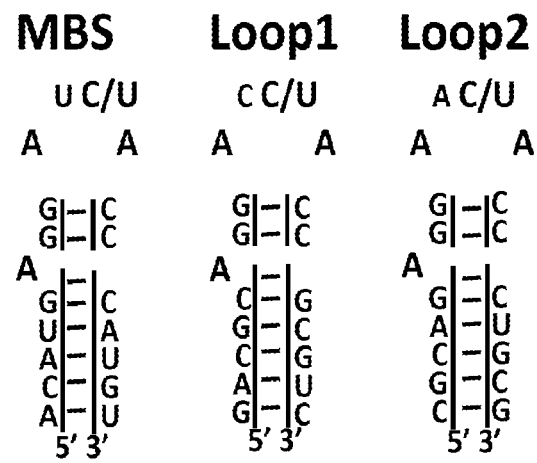
Figure 2E:
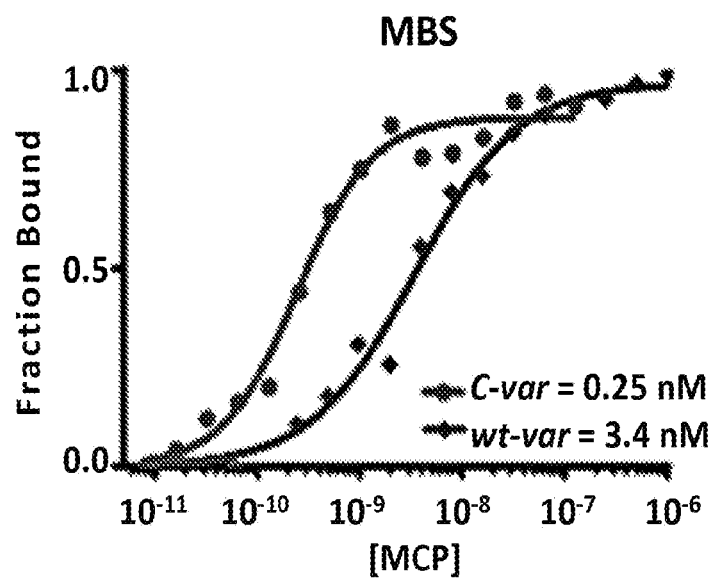
Figure 2F:
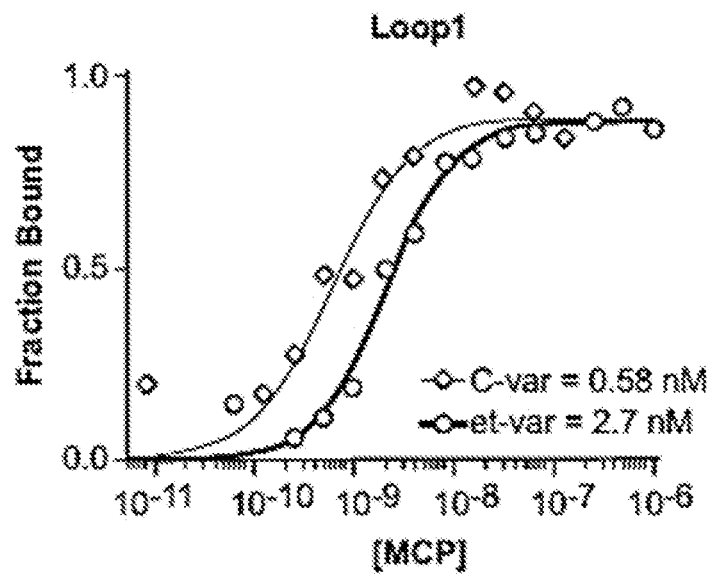
Figure 2G:
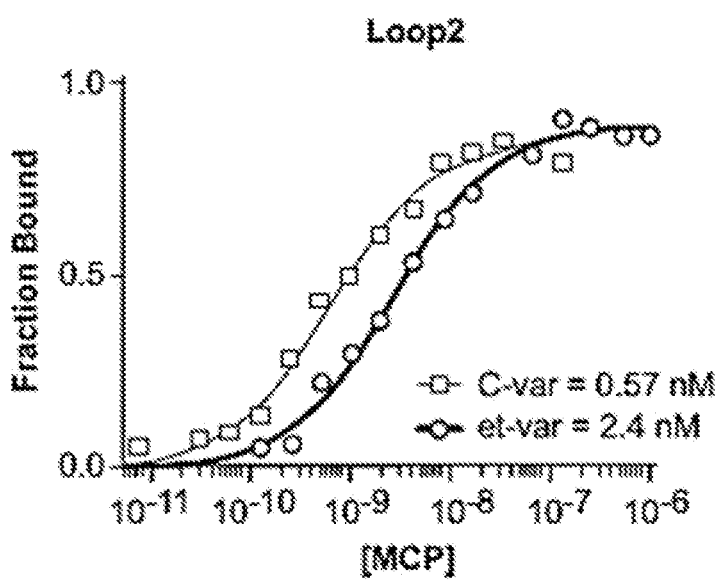

Design of a new MBS-MCP system faithfully recapitulating mRNA kinetics—We considered four variables that could influence the ability of the MS2 array to block degradation by Xm1 when MCP is bound. First, the loop sequence can affect the affinity of MCP for the stem. Previous in vitro characterization of the MBS-MCP interaction identified the MS2 C-variant, in which the wild-type (wt) uridine at position −5 of the loop is substituted by a cytosine (FIG. 2A), increasing the affinity of the MCP tenfold (Kd from 10 nM to 1 nM) and decreasing the dissociation kinetics about 90 times (Lowary and Uhlenbeck, 1987; Valegard et al., 1994; Valegard et al., 1997). The current MBSV5 and MBSORF versions have a U to C change in position −5 of all loops (FIG. 2A-C). We compared the high affinity C-variant loops to the wt-loops (FIG. 2D). The affinities of the MBS-MCP binding were analyzed by electrophoretic mobility shift assay (EMSA). As a control, we used the original loop sequence from the bacteriophage with a U or a C at position −5. In addition, C or U variants were generated for two MS2 loops (Loop1 and Loop2), each of them with a different stem sequence (FIG. 2D). Apparent equilibrium dissociation constants (Kd) were extracted from plots of MCP bound versus free (FIG. 2E-G).

For the three loops tested, MBS, Loop1 and Loop2, the Kd values of wt-variants were in the nanomolar range while the C-variants were in the sub-nanomolar range (FIG. 2, E-G). Therefore, the C to U mutation was sufficient to reduce the affinity of the MCP for the MBS independent of the sequence.

We made three additional alterations we anticipated would allow increased degradation of the RNA by Xm1. First, the stem of MBSV5 was reduced to 7 nt to further decrease affinity. Second, we increased the length of the linkers from 30 nt to either 40 or 50. Finally, we reduced the stem-loops to 12 compared to 24 to provide less substrate for degradation.

Figure 2H:
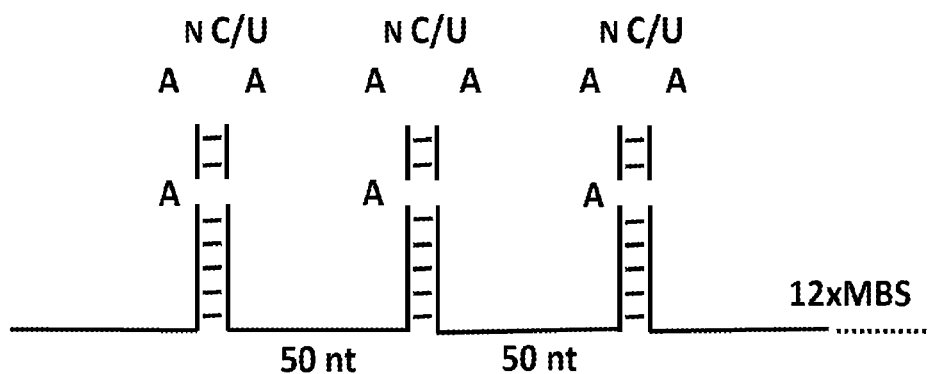
Figure 2I:
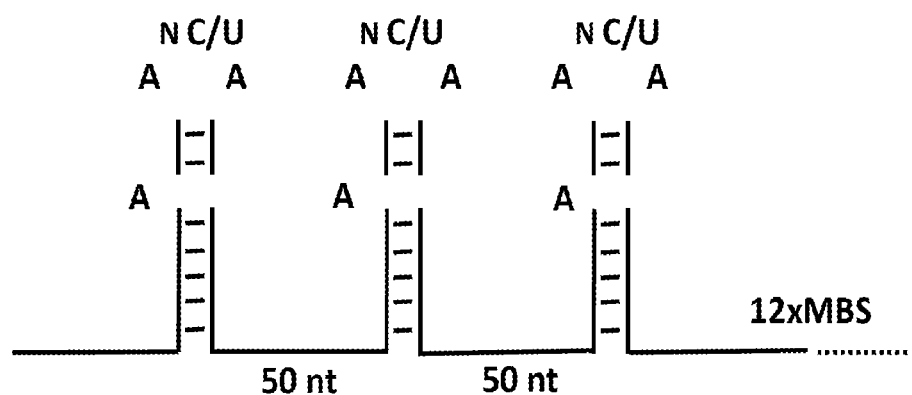
Figure 2J:
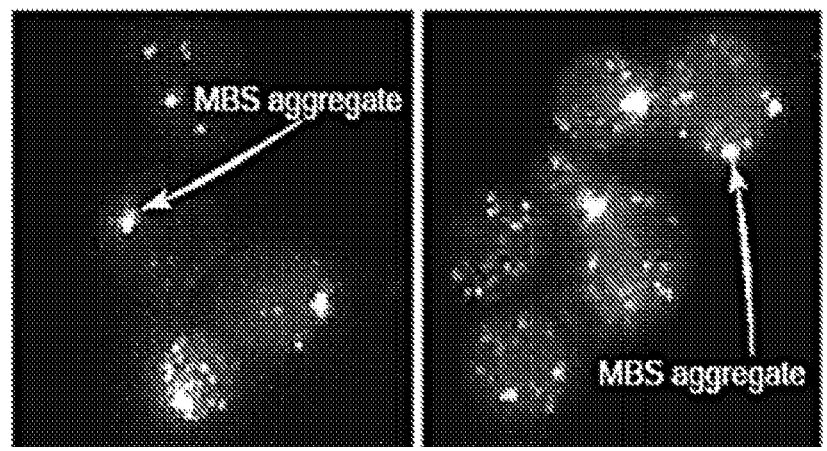
Figure 2K:
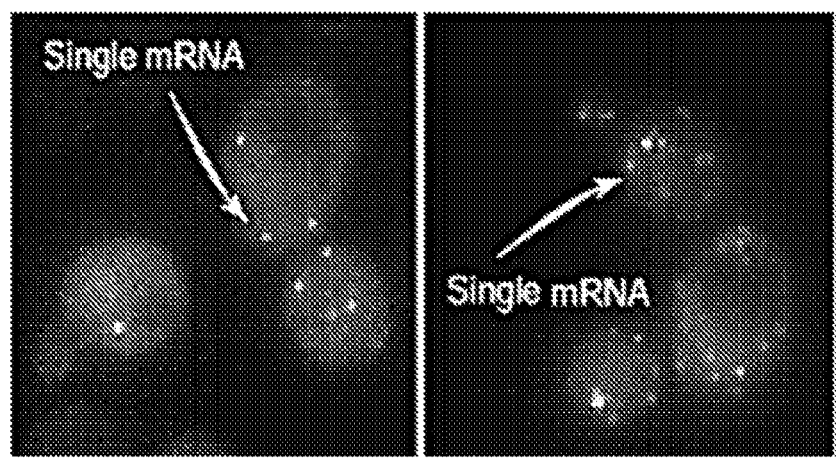
Figure 3A:
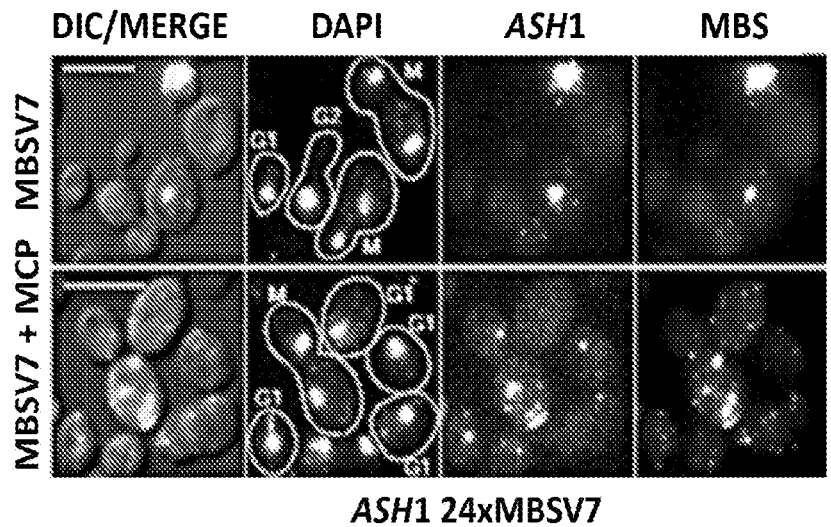
FIG. 3A-3H: Endogenous mRNAs tagged with the new MBS systems are rapidly degraded. (A and B) Two color smFISH for ASH1 mRNAs (A) and MDN1 mRNAs (B) tagged with 24×MBSV7, in cells expressing MCP (YcpLac111 CYC1p-MCP-NLS-2xyeGFP) or the vector alone (YcpLac111). (A) DIC/MERGE shows the overlap of the DAPI (blue), smFISH for the ASH1 CDS (green) and the MBSV7 (red) with the DIC image. (B) MERGE shows the overlap of the DAPI signal (blue), smFISH for the MDN1 CDS (green) and the MBSV7 (red). The shape of the cell is indicated and the corresponding cell cycle stage. Scale bar=5 μm. (C and D) Quantification of smFISH represented in 3A and 3B with CDS probes (green plots) or MBS probes (red) reported as frequency distribution of mature ASH1 (C) and MDN1 (D) mRNAs per cell. Mean and SD of two biological replicates, n=~500 cells per experiment. (E and F) Two color smFISH for ASH1 mRNAs (E) and MDN1 mRNAs (F) tagged with 24×MBSV6, in cells expressing MCP (YcpLac111 CYC1p-MCP-NLS-2xyeGFP) or the vector alone (YcpLac111). (A) DIC/MERGE shows the overlap of the DAPI (blue), smFISH for the ASH1 CDS (green) and the MBSV6 (red) with the DIC image. (B) MERGE shows the overlap of the DAPI signal (blue), smFISH for the MDN1 CDS (green) and the MBSV6 (red). The shape of the cell is indicated and the corresponding cell cycle stage. Scale bar=5 μm. (G and H) Quantification of smFISH represented in 3E and 3F with CDS probes (green plots) or MBSV6 probes (red) reported as frequency distribution of mature ASH1 (G) and MDN1 (H) mRNAs per cell. Mean and SD of two biological replicates, n=~500 cells per experiment.
Figure 3B:
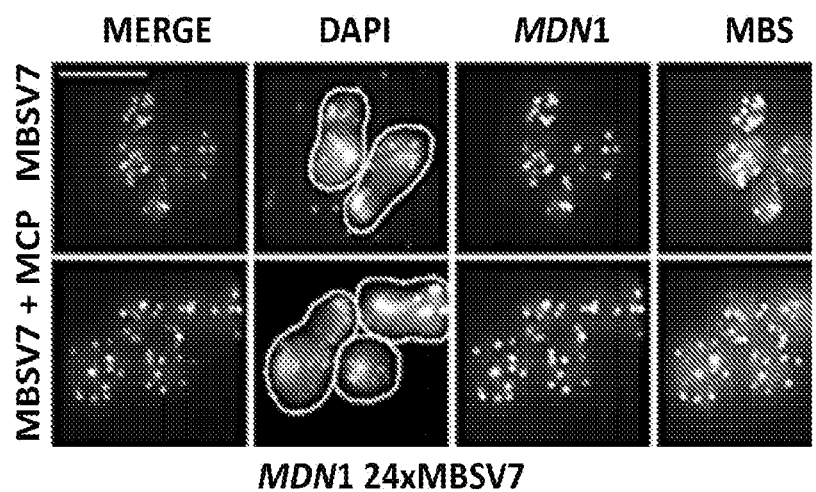
Figure 3C:
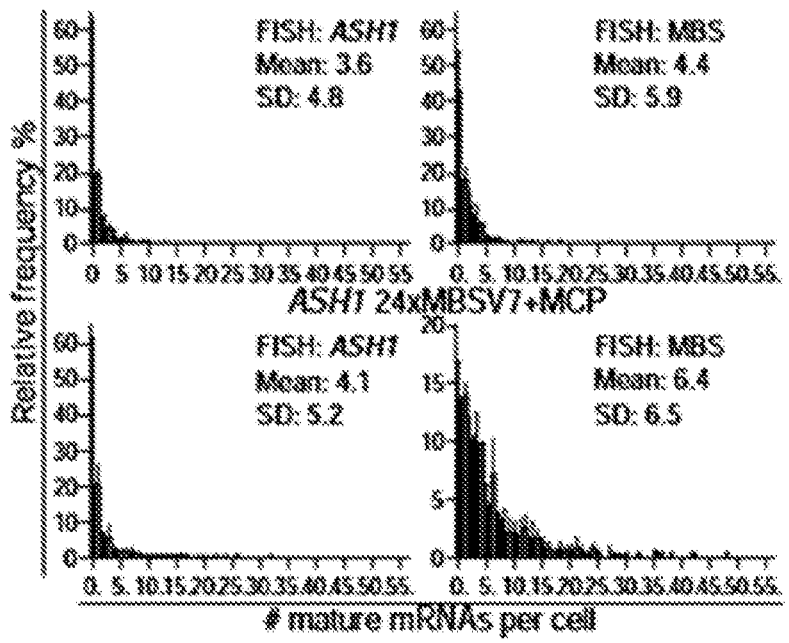
Figure 3D:
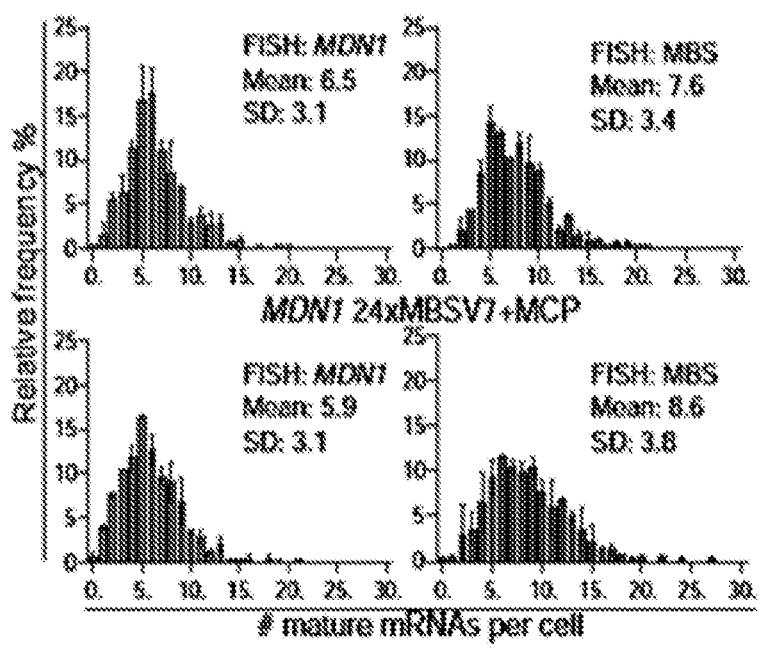
Figure 3E:
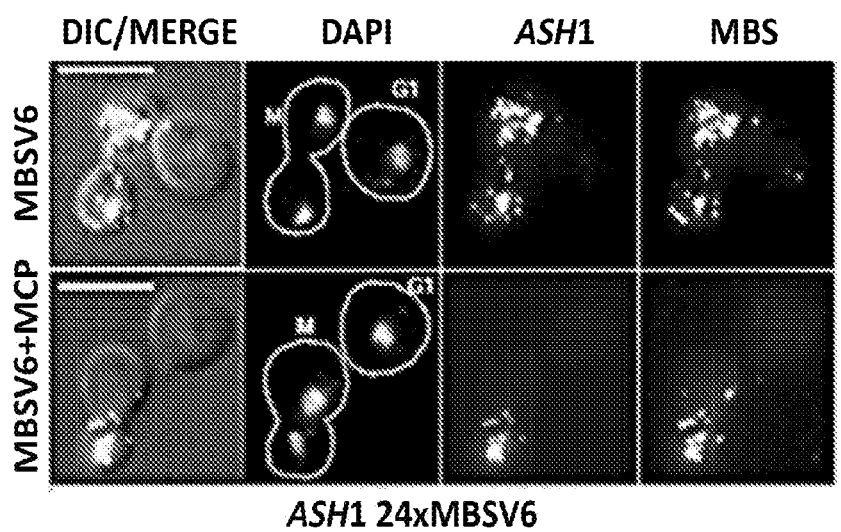
Figure 3F:
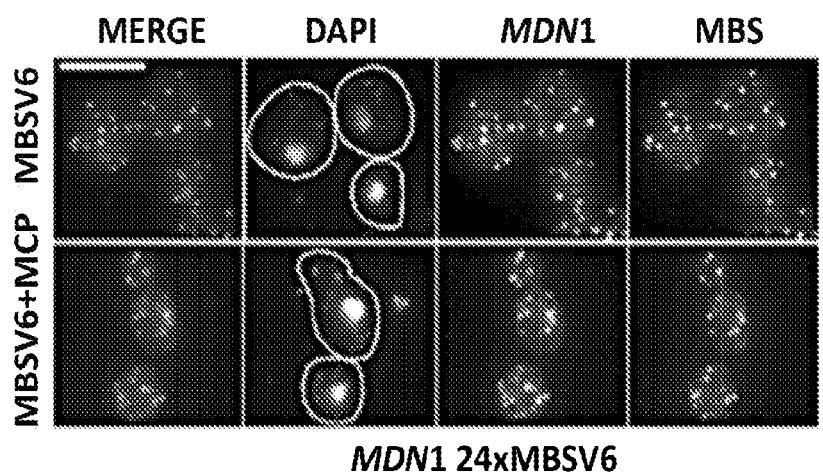
Figure 3G:
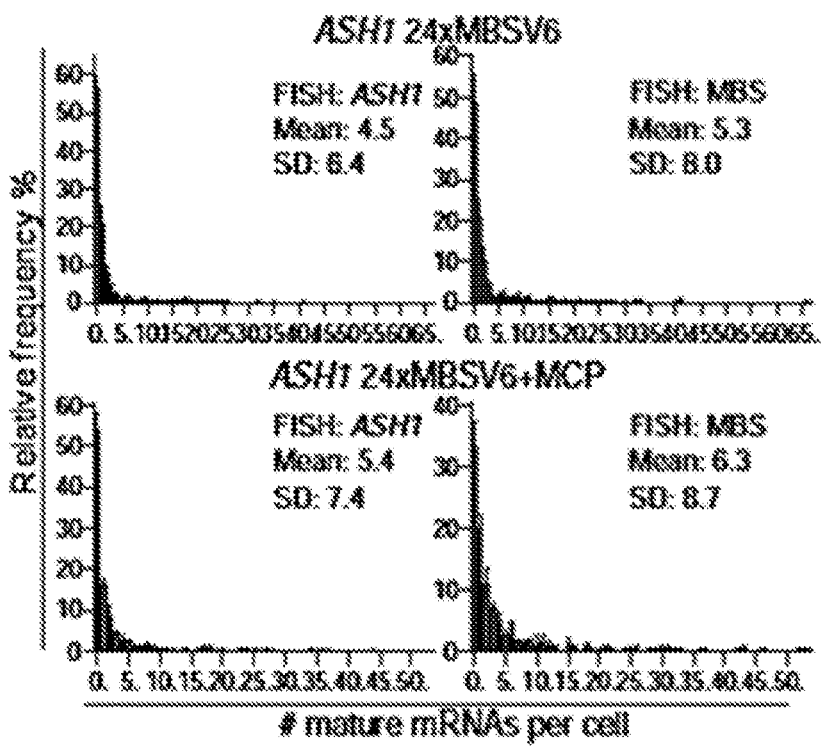
Figure 3H:
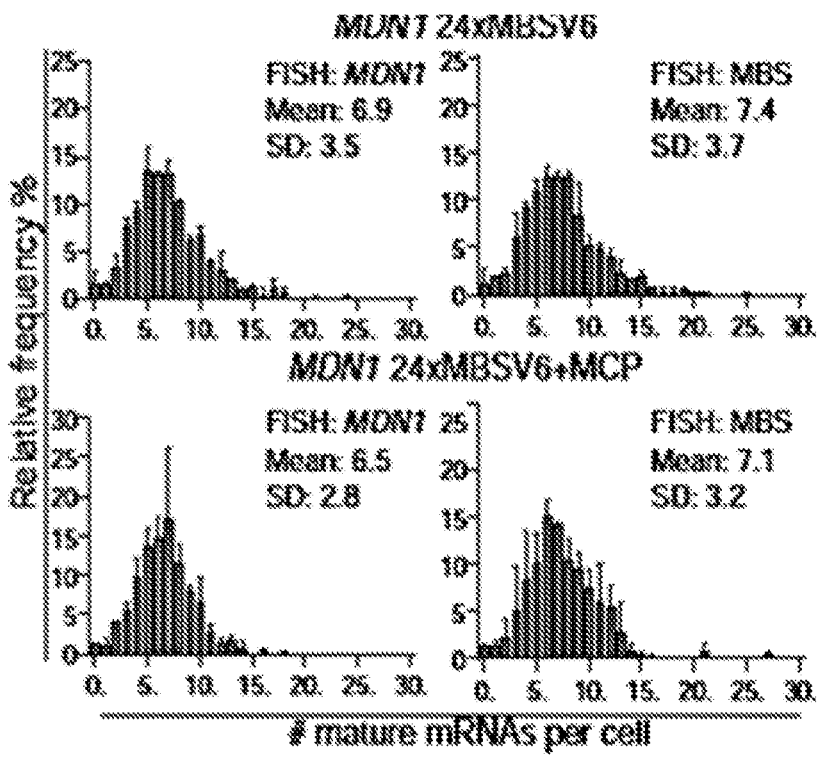
Figure 4A:
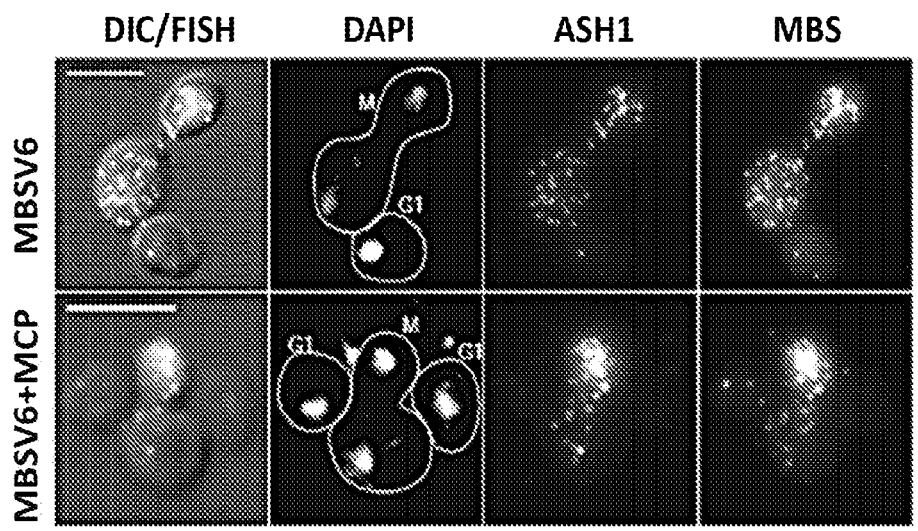
FIG. 4A-4D: Reducing the number of MBS for endogenous mRNAs tagging favors degradation. (A and B) Two color smFISH for ASH1 mRNAs (A) and MDN1 mRNAs (B) tagged with 12×MBSV6, in cells expressing MCP (YcpLac111 CYC1p-MCP-NLS-2xyeGFP) or the vector alone (YcpLac111). (A) DIC/MERGE shows the overlap of the DAPI (blue), smFISH for the ASH1 CDS (green) and the MBSV6 (red) with the DIC image. (B) MERGE shows the overlap of the DAPI signal (blue), smFISH for the MDN1 CDS (green) and the MBSV6 (red). The shape of the cell is indicated and the corresponding cell cycle stage. Scale bar=5 μm. (C and D) Quantification of smFISH represented in 4A and 4B with CDS probes (green plots) or MBSV6 probes (red) reported as frequency distribution of mature ASH1 (C) and MDN1 (D) mRNAs per cell. Mean and SD of two biological replicates, n=500 cells per experiment.
Figure 4B:
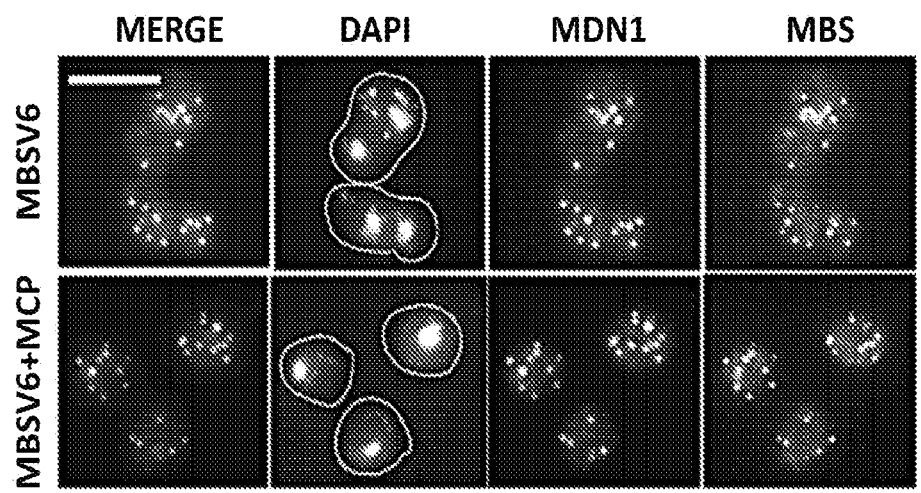
Figure 4C:
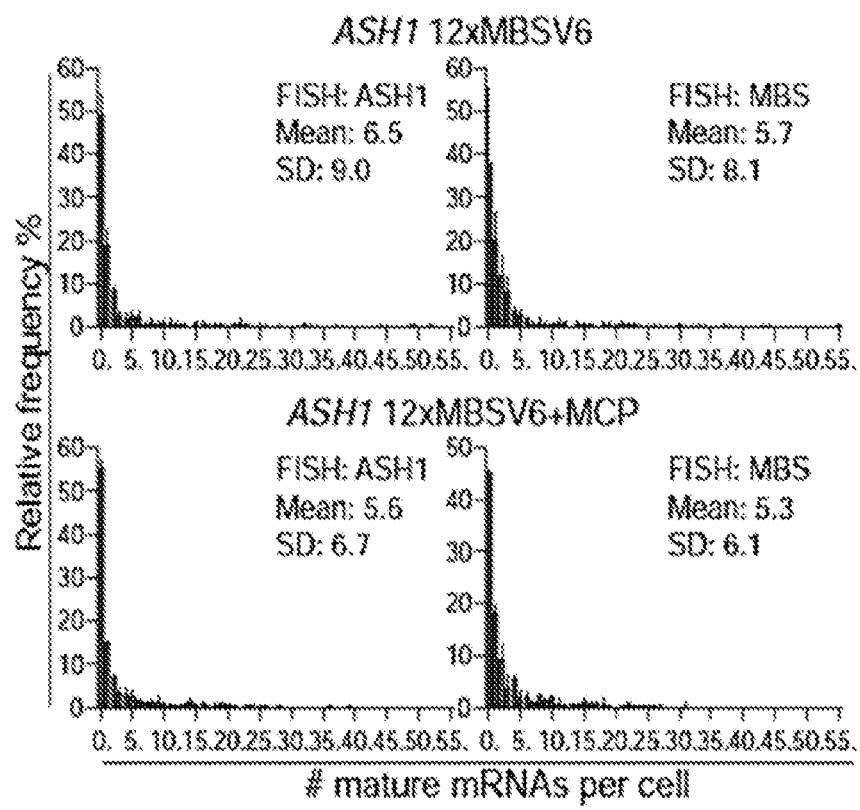
Figure 4D:
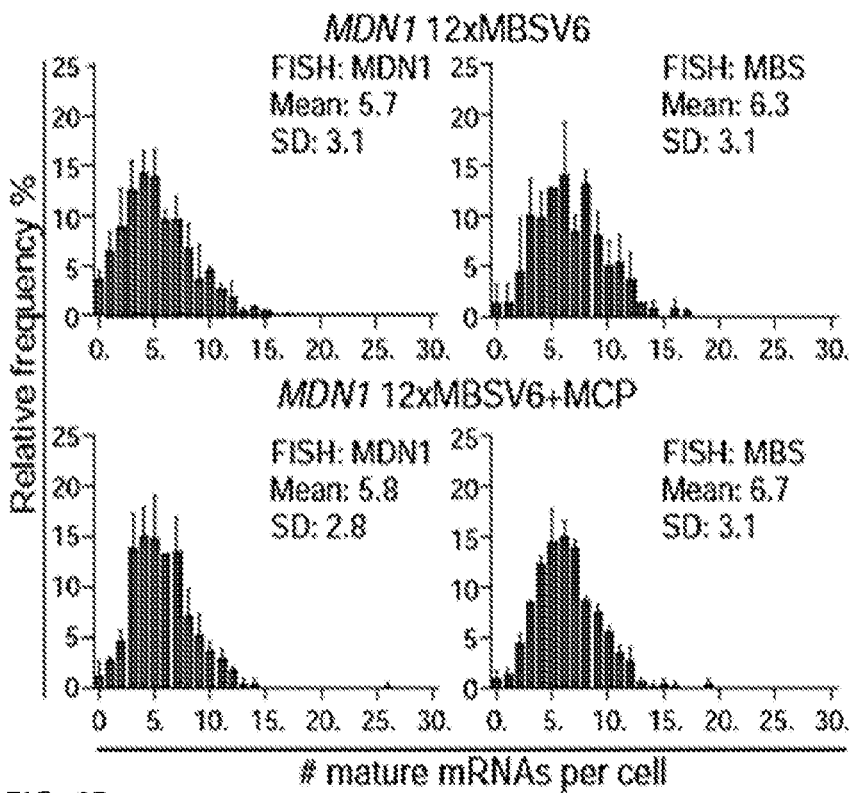

Based on these variables, we generated eight constructs: (1) 12×MBSV7 wt-variant with 12 different loops, but with a U at position −5, interspaced by 40 nt linkers; (2) 12×MBSV7 C-variant, with the same sequence but with C instead of U at position −5 in the 12 loops; (3) 12×MBSV6 wt-variant, the same loop sequences of (1) but with 50 nt linkers; (4) 12×MBSV6 C-variant, with the same sequence as (3) but with C instead of U at position −5 in the 12 loops. For comparison, a 24×MBS variant was generated by duplication of the 12 loop cassette (FIGS. 2H-I). Additionally, to avoid NMD, STOP codons were avoided in all frames. Cells co-expressing MCP with ASH1 24×MBSV6 or MDN1 24×MBSV7 Cvariant in the 3' UTR, had MBS aggregates in the cytoplasm (FIG. 2J). These observations indicated that the high affinity binding of MCP to C-variant MBS triggers the formation of MBS aggregates, independent of the stem loop sequences and the length of the stem or the linkers. In contrast, no MBS aggregates were observed in cells co-expressing the ASH1 24×MBSV6 or MDN1 24×MBSV7 lower affinity wt-variants (FIG. 2K). Most importantly, single mRNA molecules could be detected in vivo. Therefore, we proceeded with the molecular characterization of the wt-variants, MBSV6 or MBSV7.

smFISH of endogenous mRNAs tagged with wt-variants MBSV6 and MBSV7—The key experiment to see how these new MBS-MCP systems affected degradation by Xm1 was to determine if tagged mRNAs were full length. Two color smFISH was used to analyze yeast strains tagged in the 3'UTR with 24×MBSV6 or 24×MBSV7. The insertion of 24×MBSV7 in MDN1 or ASH1 mRNAs did not affect their expression (FIG. 3A-D). Co-expressing MCP reduced the percentage of cells forming small MBS aggregates to 2%, compared to 20% observed for previous MBS versions (data not shown). Reducing the insertion further to 12 stem loops (12×MBSV7) still did not prevent the accumulation of MBS aggregates in the presence of MCP (data not shown). Therefore, the MBSV7 wt, with lower affinity and 40 nucleotide linkers, ameliorated, but did not eliminate the number of cells containing MBS fragments and aggregates. In contrast to MBSV7, tagging ASH1 and MDN1 with 24×MBSV6, did not lead to the formation of MBS aggregates when co-expressing MCP and almost no fragments. Moreover, the distributions and the mean of the CDS and the MBS single molecules were similar (FIG. 3E-H). The Pearson correlation analysis of the CDS with MBSV6 or MBSV7 molecules in single cells confirmed this improvement. Reducing the stem loops from 24 to 12 for MBSV6 yielded similar results (FIG. 4A-D). Quantification of ASH1 and MDN1 mRNAs by two-color smFISH was essentially the same between the numbers of MBS and CDS molecules in cells expressing MCP, with no extra fragments (non-parametric T test, Mann Whitney test) (FIGS. 4C and 4D). To confirm that mRNAs tagged with the new MSBV6-MCP system were full length, northern blot analysis was performed using a probe hybridizing to the ASH1 mRNA after the site of MBS integration. We compared the endogenous ASH1 mRNA with tags MBSV5, MBSV7 and MBSV6, either with 24 or 12 stem loops. Consistent with previous observations, ASH1 mRNAs tagged with C-variant 24×MBSV5 and co-expressed with MCP showed the accumulation of MBS fragments (Garcia and Parker, 2015, 2016; Haimovich et al., 2016). In contrast, ASH1 mRNAs tagged with wt-variants MBSV7 and MBSV6, either 24 or 12 MBS showed a significant reduction in the accumulation of MBS fragments, as observed by smFISH.

Therefore, tagging of cycling ASH1, or constitutive MDN1 genes with the MBSV6 system recapitulated the endogenous pattern of expression and the expected cellular localization of the full-length mRNA, even when bound by MCP.

Characterization by live imaging of mRNAs tagged with MBSV6 in yeast and U2OS cells To compare the brightness of single mRNAs in live cells between the old and new constructs, we used mixed cultures from strains expressing either MDN1 24×MBSORF or MDN1 24×MBSV6. Cells were differentiated by the nuclear pore protein Nup49 tagged with tdTomato in the strain expressing MBSV6. The average intensity of single MDN1 mRNAs was determined for each strain and no significant (P=0.6753) differences were found. The bright cytoplasmic MBS aggregates in the 24×MBSORF-MCP expressing cells were excluded from the analysis because they were so bright, they were visible in the NUP (red) channels. The number of mRNAs per cell for both strains was consistent with the quantifications obtained by smFISH, indicating that the decreased affinity of MCP for the wt-variant did not compromise the detection of single mRNA molecules by live imaging.

MBSV6 could also be used to visualize single mRNAs in mammalian cells as with the previously characterized MBSV5 system (Wu et al., 2016; Wu et al., 2015). A reporter gene (coding for BFP) tagged with 24×MBSV5 or 24×MBSV6 co-expressed with tdMCP in U2OS cells after transient transfection, (Wu et al., 2016)) showed transcription sites in the nucleus (yellow circles) and single mRNAs in the cytoplasm (orange circles). The intensities of the mRNAs tagged with the two systems were similar and had a Gaussian distribution, as expected for single mRNAs molecules. These results suggested that although in mammalian cells MBS aggregates were not observed for the reporter, the MBSV6-MCP technology could be a further improvement to analyze highly unstable mRNAs.

mRNA localization during stress induced by glucose starvation—The MBS-MCP system has been used to co-localize mRNAs with Processing Bodies (PBs), stress granules or peroxisomes during stress conditions (Haim-Vilmovsky et al., 2011; Haim-Vilmovsky and Gerst, 2009; Haim et al., 2007; Sheth and Parker, 2003; Simpson et al., 2014; Zid and O'Shea, 2014). However, recent experiments suggested that only the MBS fragments, but not the CDS of the tagged mRNA, colocalize with PBs (Heinrich et al., 2017). To ensure that during stress the MBSV6 system eliminates the possibility of misinterpretation in mRNA localization experiments, we used live imaging to visualize ASH1 or MDN1 mRNAs and PBs markers during glucose starvation. We monitored PB formation during glucose starvation by co-expressing the de-capping co-factor Edc3 fused to mCherry (Haimovich et al., 2013; Kshirsagar and Parker, 2004) in cells where ASH1 or MDN1 were tagged with either the previous 24×MBSMCP system (MBSV5 or MBSORF) or 24×MBSV6-MCP. Cells expressing ASH1 or MDN1 tagged with the previous system showed cytoplasmic MBS aggregates even before glucose deprivation in both channels and substantial bleed-through that could affect interpretation of co-localization with a second labeled component. Edc3-mCherry granules started to form but no co-movement with MCP aggregates was observed after 10 minutes of glucose starvation. However, repeated interactions occurred over time between Edc3-mCherry and MCP aggregates. These results suggested that the PBs may recognize MCP aggregates as potential targets even if enclosed mRNAs were MBS fragments. However, glucose starvation did not induce the formation of MCP aggregates in cells expressing ASH1 and MDN1 mRNAs tagged with 24×MBSV6-MCP, and did not recruit single ASH1 and MDN1 mRNA molecules to PBs. Two-color smFISH confirmed that ASH1 and MDN1 mRNAs tagged with 24×MBSV6-MCP were full length throughout glucose starvation. The stress response was confirmed by smFISH for the heat shock mRNA HSP104 (Zid and O'Shea, 2014). These results validate the use of the MBSV6-MCP system for analyzing mRNA regulation during stress conditions.

Following rapid changes in mRNA degradation—Changing the carbon source produces drastic adjustments in the transcriptome of yeast cells (Lohr et al., 1995). One of the most sensitive genes to these changes is GAL1, which encodes the galactokinase involved in the first step of galactose metabolism. Shifting cells from glucose to raffinose creates a preinduced state, leading to a rapid induction of the GAL1 mRNA upon galactose addition (Hsu et al., 2012).

Conversely, washing out the galactose and adding glucose inhibits GAL1 transcription and induces GAL1 mRNA decay (Hsu et al., 2012), allowing determination of GAL1 mRNA half-life (t1/2). Two yeast strains expressing the GAL1 mRNA tagged with 24×MBSV6 with or without MCP were analyzed by two color smFISH. As expected, cells growing in raffinose do not express GAL1 mRNA.

Addition of 0.2% galactose for 30 minutes triggered similar induction of GAL1 mRNA expression quantified with either CDS or MBS probes (FIGS. 6B and S6A). After switching back from galactose to glucose, the number of CDS and MBS single molecules declined similarly over time in presence or absence of MCP, reaching undetectable levels after sixty minutes. The high levels of mRNA produced led to small MBS aggregates in a minor population analyzed separately.

To calculate the $t_{1/2}$ of GAL1 mRNA in cells without aggregates, the average number of single mRNA molecules per cell, quantified with both CDS and MBS probes at each time point after glucose addition, was normalized to that before glucose. A wt GAL1 yeast strain grown in the same conditions was used as control. The data collected for each strain were fitted to a single exponential decay model to calculate $t_{1/2}$. The endogenous GAL1 had a $t_{1/2}$=14 min. Tagging of GAL1 with 24×MBSV6 shortened its half life to $t_{1/2}$=11 minutes. Notably, the curves obtained for the CDS and the MBS probes were practically identical. In presence of MCP, the $t_{1/2}$ obtained with the MBS probes was $t_{1/2}$=17 mm, on average 1.3 times longer than the one obtained with the CDS probes ($t_{1/2}$=14 min) or the endogenous GAL1. In cells co-expressing GAL1 12×MBSV6 and MCP, the CDS and the MBS sequence were degraded simultaneously, in contrast to 12×MBSV5. The real time decay of GAL1 12×MBSV6-MCP induced by glucose was observed by live imaging during an hour. Because cells in galactose contained mRNAs at the same time points as the glucose repression, it was concluded that the reason for the mRNA signal disappearance was degradation instead of photobleaching.

Remarkably, no MBS aggregates were observed in the 12×MBSV6 strain while in 12×MBSV5, the percentage of cells with MBS aggregates increased over time from 15%, at 15 minutes of recovery, to 30% at 60 minutes. Instead, the amount of single MBS molecules per aggregate as well as the percentage of cells with aggregates decreased over time for the GAL1 tagged with 24×MBSV6 strain. Cells with MBS aggregates had more MBS single molecules than CDS molecules at any time point during recovery (data not shown). It is possible that MBSV6 aggregates formed in either cells with slower mRNA degradation or cells with stronger GAL1 induction. Therefore, by reducing the number of MBSV6 repeats from 24 to 12 we could measure precisely the abundance and degradation of highly induced and regulated genes in cells undergoing rapid metabolic adjustments.

Figure 5A:
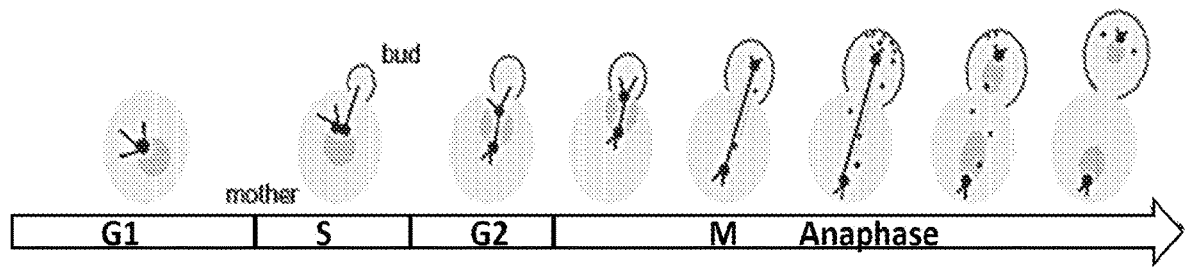
FIG. 5A-5D: ASH1 mRNA expression throughout the cell cycle can be measured with MBSV6-MCP (A) Scheme of ASH1 mRNA expression during the cell cycle (marked on red arrow). Green dots represent ASH1 mRNA. mRubyTub1 (red) marks the spindle pole body (SPB), duplicated during S phase. The bud emergence (outlined) starts during S-phase and ends with the formation of the daughter cell. (B) Representative images of video. Simultaneous two-color imaging of cells co-expressing ASH1 24×MBSV6-MCP (gray) and mRubyTub1 (red). Time 0 indicates the beginning of anaphase. Images were acquired every 2 minutes. Single molecules are seen at 10 min and end at 24 min. (C) Quantification of single ASH1 mRNAs of cell shown in (B) during the cell cycle (black dots connected by green line). Black curve indicates cytoplasmic ASH1 mRNA profiles fitted to a single exponential decay model. $t_{1/2}$=5.6 min. (D) Quantification of single DOA1 mRNAs tagged with 24×MBSV6-MCP during the complete cell cycle (n=15). Images were acquired every 2 minutes.
Figure 5B:
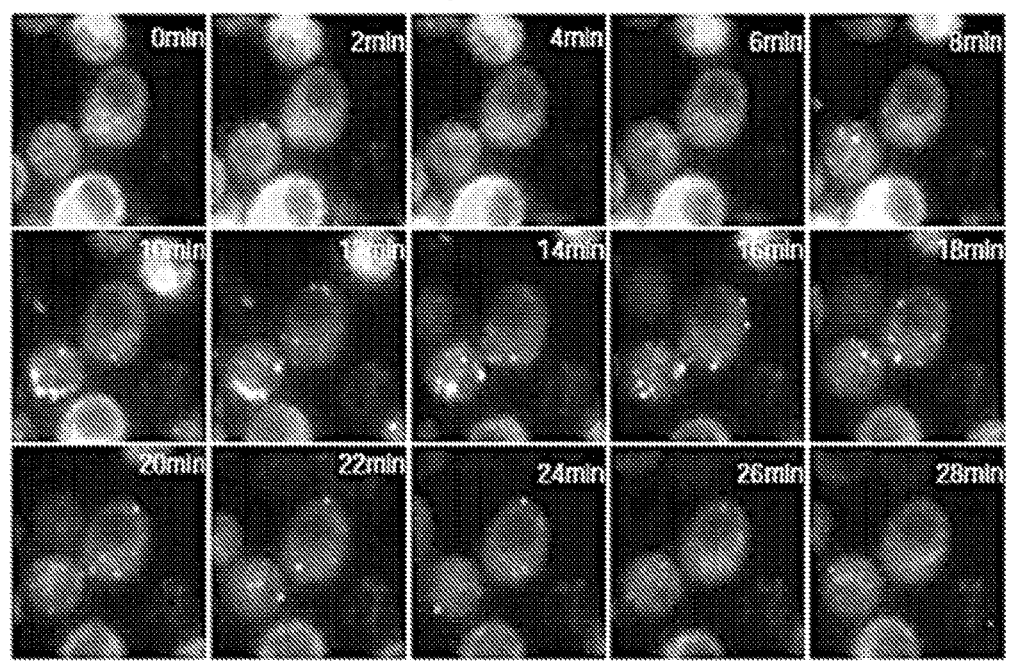

ASH1 mRNA cell cycle expression—Cell cycle regulated genes require precise regulation of their synthesis and degradation (Trcek et al., 2011). In yeast, ASH1 mRNA expression is temporally restricted to anaphase and the mRNA localizes to the bud tip where it is locally translated to control mating type switching (Heym and Niessing, 2012; Long et al., 1997a; Long et al., 1997b). To quantify ASH1 mRNAs during the cell cycle, ASH1 was tagged with 24×MBSV6 and cell cycle progression was monitored with the TUB1 gene tagged with mRuby (FIG. 7A). The microtubules extend from the spindle pole body (SPB) between the mother and daughter cell, participating in chromosome separation and mitosis (Pereira and Schiebel, 2001); FIG. 5A). ASH1 mRNA expression was preceded by microtubule stretching, allowing the clear identification of mother-daughter pairs and cell cycle phase (FIG. 5A-5B). The number of single ASH1 mRNAs for each time point was counted (a representative cell is shown and quantified in FIGS. 5B and 5C). The quantification of 21 cells showed that ASH1 mRNA was expressed during 30 minutes corresponding to anaphase of mitosis. We measured t1/2 (5.6-6.1 min), that was consistent with recent reports that the full cycle of ASH1 mRNA lasted about 30 min and the mean half-life was 6.31 min at 30° C. (FIG. 5C) (Eser et al., 2014). We observed bursts of transcription in the mother that were followed by localization of the mRNAs to the bud tip; surprisingly before the end of mitosis a second burst of accumulation occurred in the bud tip, presumably from transcription in the daughter. The ASH1 mRNAs in the daughter cell stayed for a prolonged period before degradation.

To investigate the origin of the second accumulation, we analyzed ASH1 transcription during the cell cycle. To facilitate the visualization of the transcription site, a kanamycin resistance gene was added to the ASH1 24×MBSV6 3'UTR, in order to increase the residence time of the nascent transcripts. To identify the nucleus, and the transcription site therein, we co-expressed 2×mCherry fused to an NLS. Simultaneous imaging of MCP and NLS-2×mCherry, revealed that transcription occurred both in the mother and the daughter cell nuclei. This suggests that mRNA transport from the nucleus to the bud tip may be regulated differently between mRNAs produced in the mother or the daughter cell.

To demonstrate that the disappearance of the mRNA signal is due to mRNA decay and not to photo-bleaching, we used the live imaging method to follow an mRNA with a longer half-life. The DOA gene that is constantly expressed throughout the cell cycle (Trcek et al., 2011) was tagged with 24×MBSV6. The number of single DOA1 molecules was constant over the cell cycle with an average of 2.9±1.1 mRNAs/cell (FIG. 5D). Accordingly, two-color smFISH experiments with DOA or MBSV6 probes reported 3.6±2.9 mRNAs/cells and a Gaussian distribution, characteristic of constitutive genes. Thus, most of the mRNAs expressed in the cell could be visualized in vivo by the MBSV6-MCP system. These experiments demonstrated that the MBSV6 system provided the temporal and spatial resolution required to quantify the expression of mRNAs from birth to death in cells grown in optimal or stress conditions.

Discussion

The MBS-MCP system has been extensively used to study gene expression regulation by following endogenously tagged mRNAs (Vera et al., 2016). The use of MBSV5 with the C-variant is appropriate for mammalian cells where mRNAs with long half-lives are investigated. However, in cases where the mRNA half-life is short and degradation of the MBS becomes rate limiting, the MBS can accumulate (Garcia and Parker, 2015, 2016; Haimovich et al., 2016; Heinrich et al., 2017). Therefore, we engineered and characterized a new MBS-MCP system that faithfully recapitulates the life cycle of the mRNA while preserving single molecule resolution. The approach can be used to validate mRNAs tagged with orthologous systems, such as PP7 (Chao et al., 2008) or U1A in yeast (Caponigro et al., 1993). Other systems to detect endogenous mRNA molecules, like the Spinach aptamer (Guet et al., 2015) or the Cas9 System (Nelles et al., 2016), do not yet reach the single-molecule sensitivity obtained by the MBS-MCP system.

The key improvement made for the application of the MBS-MCP system to short-lived mRNAs was to reduce the binding affinity between the MBS and MCP. Strikingly, the modification of one nucleotide at position −5 of the MS2 loop, from the wt uridine to cytosine in the C-variant, was sufficient to reduce the Kd about 10 fold, regardless of the stem loops sequence (FIG. 2 E-G) (Lowary and Uhlenbeck, 1987).

Figure 5C:
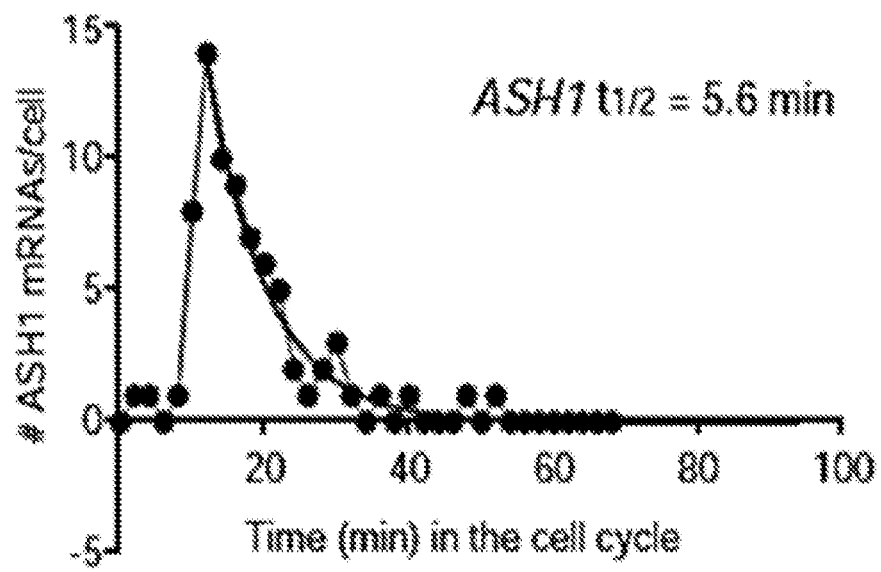
Figure 5D:
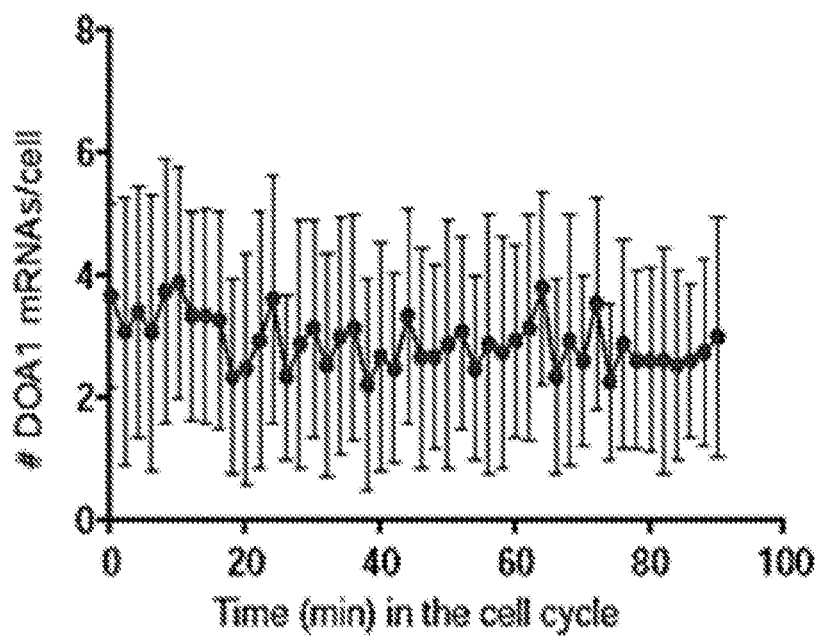

Importantly this modification did not affect the brightness and detection of single molecule mRNAs suggesting that the recycling of MCP molecules could compensate for the decrease in affinity, and might reduce photobleaching by replenishment of the MCP (FIG. 5C). This MBS-MCP system, MBSV6, was inserted into the 3'UTRs of ASH1, MDN1 and DOA mRNAs, at the endogenous loci to preserve the regulatory elements. In all cases, MBSV6 faithfully reported the lifetime of the full-length mRNA by reducing the accumulation of MBS fragments and preventing the formation of MBS aggregates. Therefore, for imaging or biochemical experiments the MBSV6 avoids the risk of experimental artifacts derived from the accumulation of intermediate degradation products. Nonetheless, for highly expressed genes like GAL1, 24×MBSV6 still triggered the formation of small MBS aggregates in 5% of the cells co-expressing MCP, indicating that degradation of highly expressed long stem loops (24×) is challenging for yeast cells.

Shorter stem loops (12×) however avoided the formation of degradation intermediates and enabled the degradation of the CDS and the MBS with the same kinetics (FIG. 6C). Further work will elucidate if the accumulation of RNA-protein aggregates is a mechanism to degrade structured mRNAs, such as the one bearing poly-G tracts, already known for blocking Xm1 activity (Sheth and Parker, 2003).

Previous reports suggested that the MBS system is particularly sensitive to stress conditions (Heinrich et al., 2017). Upon stress induction, coordinated recruitment of mRNAs tagged with MBSV6 to PBs was not observed. Because mRNAs in the cytoplasm are efficiently translated (Ingolia et al., 2009), long mRNAs like MDN1 are likely protected by ribosomes from recruitment to PBs. Conversely, the ASH1 mRNA translation is inhibited until the mRNA localizes to the bud tip, suggesting that other mechanisms could exist to protect these mRNAs from going to PBs. Further work is required to re-evaluate the role of PBs, and other cytoplasmic structures, in coordinating the cellular response to stress. For this purpose, the MBSV6-MCP offers the spatial and temporal resolution to elucidate the interactions of mRNAs and RNA binding proteins, forming cytoplasmic mRNP granules. These two color experiments would also provide insights on mRNA decay regulation and on the kinetics of assembly and disassembly of stress granules.

MBSV6 allows quantifying single mRNA in living cells during their entire life-cycle. Time-lapse imaging showed that the ASH1 mRNAs were produced from a transcriptional burst rapidly occurring during anaphase both in the mother and in the daughter nuclei. ASH1 mRNAs are then correctly localized to the bud tip, where they remained for as little as 8 minutes during mitosis (FIG. 7B), emphasizing the precise temporal resolution of this approach. The improved sensitivity of this system allowed us to observe a second burst of transcription in the daughter nucleus that led to mRNAs that could be observed in the cytoplasm for few minutes after mitosis, although mRNAs did not remain in the mother cell.

These results suggest either that ASH1 mRNAs are efficiently transported from the mother to the daughter cell, or they are selectively degraded in the mother. Further experiments using the MBSV6 will elucidate factors required to regulate the coupling between ASH1 mRNA localization, translation and decay.

The value of this new MS2 system is to provide a new capability for imaging and measuring the regulatory events of the entire RNA lifetime without perturbation. In particular, the decay events of single RNAs in single cells can now be elucidated with temporal and spatial resolution sufficient to study the localization and function of highly unstable RNAs, such as non-coding or regulatory RNAs.

Materials and Methods

Yeast strains construction—Yeast strains were constructed in the BY4741 or BMA64-1A background. All strains where a gene of interest was tagged with MBSs in the 3'UTR, right after the STOP codon, were prepared as follow: PCR amplification of the MBS insert (see plasmids in Table 2) followed by the kanamycin resistance gene, flanked by Loxp sequences, was performed with oligos (see oligos Table 3) containing homology sequences (50-70 nt) for the specific gene. For all strains, the Kanamycin resistance gene was removed by expressing the CRE recombinase under the control of the GAL1 promoter. Genomic DNA was extracted using standard techniques and PCR amplification of the 3' UTR was loaded on a gel and sent for sequencing to verify the size of the insert.

Plasmids construction—The new MBS sequences, wt or C-variants, 12×MBSV6 and 12×MBSV7 were synthetized by Genscript. To obtain the 24×MBSV6 and 24×MBSV7 we cloned the 12×MBS V6/V7 in tandem by using restriction enzymes BamHI and BglII. Orientation of the insert was confirmed by sequencing. The 12×MBS or 24×MBS variants were then transferred in the yeast vector containing the Kanamycin resistance gene flanked by Loxp by using the restriction enzymes BamHI SalI. The plasmid pET296 was generated by inserting the CYC1p, amplified from genomic DNA of BY4741, with flanking restriction enzymes XhoI and BamHI. The NLS from SV40 was added at the C-terminus of the MCP coding sequence by PCR amplification using a reverse oligo containing the NLS sequence, flanked by restriction enzymes BamHI and Age. In the SINAPV5 plasmid the sequence of 24×MBSV5 was replaced by digesting with AgeL and ClaI restriction enzymes and inserting within the same site 24×MBSV6 amplified by PCR. For EMSAs a C-terminal His Tag was added by PCR and MCP-His was cloned using BamHI and HindIII sites into a pMalc derivative that contains a Tobacco Etch Virus (TEV) site after the maltose-binding protein (plasmid pET336-Table 1).

smFISH probes preparation—ASH1, DOA1, GAL1, MDN1, MBSV5, MBSV6, MBSV7 probes were designed using the Stellaris™ Probe Designer by LGC Biosearch Technologies and purchased from Biosearch Technologies. HSP104 and MBSORF probes were synthetized by Invitrogen-Thermo Fisher, and labelled in the lab using Cy3 dyes (Amersham) as previously described (Trcek et al., 2012).

smFISH and image acquisition and analysis—Single molecule FISH (smFISH), was essentially performed as described in (Trcek et al., 2012) with the following modifications. Yeast strains were grown overnight at 25° C. in selective medium with 2% glucose. In the morning cells were diluted to OD600 0.1 and allowed to grow until OD600 0.3-0.4. Yeast strains tagged in the GAL1 gene were grown for twenty-four hours in SC-Leu supplemented with 2% Raffinose. At OD=0.3, GAL1 expression was induced with 0.2% galactose for thirty minutes and decay was induced by adding 4% glucose, as described in FIG. 5A. Cells were fixed by adding paraformaldehyde (32% solution, EM grade; Electron Microscopy Science #15714) to a final concentration of 4% and gently shacked at room temperature for 45 minutes. Cells were then washed 3 times with buffer B (1.2M sorbitol and 100 mM potassium phosphate buffer pH=7.5) and resuspended in 500 µL of spheroplast buffer (buffer B containing 20 mM VRC (Ribonucleoside-vanadyl complex NEB #S1402S), and 25 U of Lyticase enzyme (Sigma #L2524) per OD of cells for about 10 minutes at 30° C. Digested cells were washed once with buffer B and resuspended in 1 mL of buffer B. 150 µL of cells were seeded on 18 mm poly-lysine treated coverslips and incubated at 4° C. for 30 minutes. Coverslips were washed once with buffer B, gently covered with ice-cold 70% ethanol and stored at −20° C. For hybridization, coverslips were rehydrated by adding 2×SSC at room temperature twice for 5 minutes. Coverslips were pre-hybridized with a mix containing 10% formamide (ACROS organics #205821000)/2×SSC, at room temperature for 30 minutes. For each coverslip the probe mix (to obtain a final concentration in the hybridization mix of 125 nM) was added to 5 µL of 10 mg/µL E. coli tRNA/ssDNA (1:1) mix and dried with a speed-vac. The dried mix was resuspended in 25 µL of hybridization mix (10% formamide, 2×SSC, 1 mg/ml BSA, 10 mM VRC, 5 mM NaHPO4 pH 7.5) and heated at 95° C. for 3 minutes. Cells were then hybridized at 37° C. for 3 hours in the dark. Upon hybridization coverslips were washed twice with pre-hybridization mix for 30 minutes at 37° C., once with 0.1% Triton X-100 in 2×SSC for 10 minutes at room temperature, once with 1×SSC for 10 minutes at room temperature. Nuclei were stained with 0.5 µg/mL DAPI in 1×PBS for 2 minutes at room temperature, washed with 1×PBS for 10 minutes at room temperature. Coverslips were mounted on glass slides using ProLong Gold antifade (Thermo Fisher). Images were acquired using an Olympus BX61 wide field epi-fluorescence microscope with a 100×/1.35NA UPanApo objective. Samples were visualized using an X-Cite 120 PC lamp (EXFO) and the ORCA-R2 Digital CCD camera (Hamamatsu). Metamorph software (Molecular Devices) was used for acquisition. Z-sections were acquired at 200 nm intervals over an optical range of 8.0 µm. Image pixel size: XY, 64.5 nm. FISH images were analyzed using FISHQUANT (Mueller et al., 2013). Briefly, after background subtraction, the FISH spots in the cytoplasm were fit to a three-dimensional (3D) Gaussian to determine the coordinates of the mRNAs. The intensity and width of the 3D Gaussian were thresholded to exclude nonspecific signal. The average intensity of all the mRNAs was used to determine the intensity of each transcription site.

Sample preparation for live yeast fluorescence imaging Yeast cells were grown at 25° C. in synthetic selective medium. Exponentially growing cells (O.D. 0.2-0.4) were plated on coated Delta-T dishes (Bioptech-04200417C). The dishes coating was done by incubating with Concanavalin A 1 mg/ml (Cayman chemical company) for 10 minutes at room temperature. Excess liquid was aspirated and dishes were dried at room temperature. To activate Concanavalin A, dishes were incubated for 10 minutes at room temperature with a 50 mM $CaCl_2$ 50 mM $MnCl_2$ solution. Excess was removed and dishes dried at room temperature. Finally, dishes were washed once with ultrapure water (Invitrogen), and let completely dry at room temperature. Cells attachment was performed by gravity for 20 minutes at room temperature, excess liquid removed and substitution with fresh media.

Glucose deprivation was performed by growing cells co-transformed with plasmids MCP-2×GFP and Edc3-mCherry in double selective medium with—2% glucose overnight at 25° C. Cells were diluted in the morning and grown until OD600 0.3-0.4. Cells were plated on Concanavalin A coated dishes. Images were acquired before glucose starvation and then, keeping the dishes on the microscope stage with appropriate temperature control, washes were performed 6 times with 1 ml of medium without glucose. Cells were then kept in medium lacking glucose at 25° C. taking z-stacks every minute for 40 minutes.

Live cells fluorescence imaging and image analysis—The two-color simultaneous imaging of mRNAs and the appropriate cellular marker was performed on a modified version of the home-built microscope described in (Wu et al., 2016). Briefly, the microscope was built around an IX71 stand (Olympus). For excitation, a 491 nm laser (Calypso™, Cobolt) and a 561 nm laser (Jive™, Cobolt) were combined and controlled by an acoustic-optic tunable filter (AOTF, AOTFnC-400.650-TN, AA Opto-electronic) before coupled into a single mode optical fiber (Qioptiq). The output of the fiber was collimated and delivered through the back port of the microscope and reflected into an Olympus 150×1.45 N. A. Oil immersion objective lens with a dichroic mirror (zt405/488/561rpc, 2 mm substrate, Chroma). The tube lens (180 mm focal length) was removed from the microscope and placed outside of the right port. A triple band notch emission filter (zet405/488/561m) was used to filter the scattered laser light. A dichroic mirror (T560LPXR, 3 mm substrate, Chroma) was used to split the fluorescence onto two precisely aligned EMCCDs (Andor iXon3, Model DU897) mounted on alignment stages (x, y, z, θ- and φ-angle). Emission filters FF03-525/50-25 and FF01-607/70-25 (Semrock) were placed in front of green and red channel cameras respectively. The two cameras were triggered for exposure with a TTL pulse generated on a DAQ board (Measurement Computing). The microscope was equipped with a piezo stage (ASI) for fast z-stack and a Delta-T incubation system (Bioptech) for live cell imaging. The microscope (AOTF, DAQ, Stage and Cameras) was automated with the software Metamorph (Molecular Devices). For two-color live cell imaging, yeast cells were streamed at 50 ms, Z plane was streamed, and Z-stacks acquired every 0.5 μm. Single molecule analysis was done on the maximal projected images using AIRLOCALIZE (Lionnet et al., 2011).

Recombinant Protein Preparation—Transformation of pET336 and purification were performed as previously described (Chao et al., 2008). In brief, constructs were transformed into Rosetta2 cells (EMD Millipore) and protein induction was performed for 4 hours at 37° C. Cell pellets were lysed by sonication in 50 mM Tris pH 7.2, 1.5M NaCl, 1 mM EDTA, 1 mM DTT supplemented with one Complete EDTA-free protease inhibitor tablet (Roche). After centrifugation, the soluble protein was first purified by amylase affinity chromatography (New England Biolabs) and subsequently by TALON affinity chromatography (Takara Bioscience).

Electrophoretic Mobility Shift Assay (EMSA)—Single stem loop fragments with 5' fluorescein modification (Dharmacon) were deprotected as per the manufacturer recommendation. Prior to the experiment, RNA stocks were heated to 70° C. for 5 minutes then snap cooled on ice. The sequences of the RNAs used for these experiments are listed in Table 1.

TABLE 1

RNA used for EMSA

| Name | Variant | Sequence |
| --- | --- | --- |
| MS2 | wt | ACATGAGGATTACCCATGT |
| MS2 | C | ACATGAGGATCACCCATGT |
| V6/V7 SL_1 | wt | GACGCAGGACTACCGCGTC |
| V6/V7 SL_1 | C | GACGCAGGACCACCGCGTC |
| V6/V7 SL_9 | wt | CGCAGAGGAATACCCTGCG |
| V6/V7 SL_9 | C | CGCAGAGGAACACCCTGCG |

(Top to bottom, SEQ ID NOS:5-10, respectively).

Complexes were monitored and quantified by EMSA as previously described (Chao et al., 2008). In brief, 100 pM RNAs were incubated at room temperature for three hours with 2 fold dilutions of MCP in 10 mM Tris, 100 mM NaCl, 0.1 mM EDTA, 0.01 mg/mL tRNA, 50 g/mL heparin and 0.01% IGEPAL CA630. Complexes were then run using 5% native PAGE in 0.5×TBE and visualized using the Typhoon 9400 variable mode laser scanner (GE Healthcare).

RNA preparation and Northern blots—Total mRNA was isolated from yeast cultures grown at 25° C. in synthetic selective medium as described in (Caponigro et al., 1993). Northern blots were performed by resolving 10 μg total RNA on 1.5% formaldehyde agarose gel, transferring by capillary action to a Nytran membrane, and, probing blots with [32P] end-labelled oligonucleotide complementary to the 3' UTR of ASH1 (5'-ACAAGGAGAGAAATGTA-CAATTGTTTCGTGATAATGTCTCTTATTAGTTG-3') (SEQ ID NO:11) as described in detailed in (Passos and Parker, 2008). Blots were stripped and reprobed for the 7S RNA using the following probe oRP100 (5'-GTCTAGCCGCGAGGAAGG-3') (SEQ ID NO:12). Blots were visualized using a phosphoimager.

Mammalian cell cultures—Human U2OS osteoscarcoma cell line (American Type Culture Collection HTB-96) stable expressing tdMCPGFP (Wu et al., 2012) were grown at 37° C. and 5% CO2 in DMEM supplemented with 10% fetal bovine serum, 4.5 g/L glucose and 1% penicillin-streptomycin. Cells were transient transfected with SINAPV5 (Wu et al., 2016) or SINAPV6 (Table 1) with lipofectamine 3000 twenty-four hours before being subjected to live imaging experiments.

TABLE 2

Plasmids used in this study

| Code | Name | Yeast Marker | Reference | Notes |
|---|---|---|---|---|
| pDZ415 | 24xMS2ORF | KAN | Hocine S, Raymond P, Zenklusen D, Chao J A, Singer R H. Nat Methods. 2013 February; 10(2): 119-21. | Addgene 45162 |
| pET157 | YcpLac111 | LEU2 | Rizzardi et al Genetics. 2012 October; 192(2): 371-84. doi: 10.1534/genetics.112.142349 | Addgene 53249 |
| pET184 | pSH47 GAl1p CRE ricombinase URA3 | URA3 | Güldener U, Heck S, Fiedler T, Beinhauer J, Hegemann J H. A new efficient gene disruption cassette for repeated use in budding yeast. Nucleic Acids Research 1996; 24, 2519-2524 | from Euroscarf |
| pET185 | pSH62 GAl1p CRE ricombinase HIS3 | HIS3 | Güldener U, Heinisch J, Köhler G J, Voss D, Hegemann J H. A second set of loxP marker cassettes for Cre-mediated multiple gene knockouts in budding yeast. Nucleic Acids Research 2002; 30, e23 | from Euroscarf |
| pET194 | p415 KAN 24xMS2V5 | KAN | Wu, B., V. Miskolci, H. Sato, E. Tutucci, C. A. Kenworthy, S. K. Donnelly, Y. J. Yoon, D. Cox, R. H. Singer and L. Hodgson (2015). "Synonymous modification results in high-fidelity gene expression of repetitive protein and nucleotide sequences." Genes Dev 29(8): 876-886. | |
| pET334 | p415 KAN 12xMS2V5 | KAN | This study | |
| pET246 | pUC57 12xMS2V6 wt loop 50 nt linker | XXX | This study | |
| pET247 | pUC57 12xMS2V6 C-var loop 50 nt linker | XXX | This study | |
| pET248 | pUC57 12xMS2V7 wt loop 41 nt linker | XXX | This study | |
| pET249 | pUC57 12xMS2V7 C-var loop 41 nt linker | XXX | This study | |
| pET251 | p415 12xMS2V6 50 nt linker WT Loxp KANr Loxp | KAN | This study | |
| pET252 | p415 12xMS2V6 50 nt linker C-var Loxp KANr Loxp | KAN | This study | |
| pET255 | p415 12xMS2V7 41 nt linker WT Loxp KANr Loxp | KAN | This study | |
| pET256 | p415 12xMS2V7 41 nt linker C-var Loxp KANr Loxp | KAN | This study | |
| pET259 | pUC57 inverted 24xMS2V6 wt 50 nt linker | XXX | This study | |
| pET261 | pUC57 24xMS2V6 C-var 50 nt linker | XXX | This study | |

TABLE 2-continued

Plasmids used in this study

| Code | Name | Yeast Marker | Reference | Notes |
|---|---|---|---|---|
| pET262 | pUC57 24xMS2V7 wt loop 41 nt linker | XXX | This study | |
| pET263 | pUC57 24xMS2V7 C-vart loop 41 nt linker | XXX | This study | |
| pET264 | p415 24xMS2V6 50 nt linker WT Loxp KANr Loxp | KAN | This study | |
| pET265 | p415 24xMS2V6 50 nt linker C-var Loxp KANr Loxp | KAN | This study | |
| pET268 | p415 24xMS2V7 41 nt linker WT Loxp KANr Loxp | KAN | This study | |
| pET269 | p415 24xMS2V7 41 nt linker C-var Loxp KANr Loxp | KAN | This study | |
| pET296 | YcpLac111 CYC1p 1xMCP-NLS-2xyeGFP | LEU2 | This study | NLS form SV40 |
| pET316 | pHIS3p mRuby2-Tub1 + 3'UTR HIS3 | HIS3 | Markus S M, Omer S, Baranowski K, Lee W L. Traffic. 2015 July; 16(7): 773-86. doi: 10.1111/tra.12276 | Addgene 50657 |
| pET317 | pCUP1-DuDre-Atg8-404 | TRP1 | Li D, Song J Z, Shan M H, Li S P, Liu W, Li H, Zhu J, Wang Y, Lin J, Xie Z. *Autophagy*. 2015; 11(6): 954-60. doi: 10.1080/15548627.2015. | Addgene 69201 |
| pET336 | pMBP-TEV-MCP-6HIS | XXX | This study | |
| SINAPV5 | Flag-24xSuntagV4-oxBFP-AID-24MBSV5 | XXX | Wu et al Science. 2016 | |
| SINAPV6 | Flag-24xSuntagV4-oxBFP-AID-24MBSV6 | XXX | This study | |
| pDZ274 | tdTomato Loxp KanR Loxp | KAN | Larson et al. Science 2011 | |
| pMC438 | Edc3-mCherry under endogenous promoter | URA3 | Haimovich et al. Cell 2013 | |
| pRP1152 | Dcp2-RFP under endogenous promoter | URA3 | Seth and Parker Science 2003 | |

TABLE 3

Oligos used in this study (SEQ ID NOS: 13-31, top to bottom, respectively)

| code | Name | Sequence 5'-3' |
|---|---|---|
| OET156 | ASH1 3UTR Tagging Fw (V5) | TGCGAAATTGAAGGGTACCGTTGCTTATTTTGTAATTACATAACTGAGACAGTAGAGAATTGAAACCTACAAACGGGTGGAGGATCA |
| OET157 | ASH1 3UTR Tagging Fw (V6/V7) | TGCGAAATTGAAGGGTACCGTTGCTTATTTTGTAATTACATAACTGAGACAGTAGAGAATTGACCGCTCTAGAACTAGTGGAT |
| OET257 | ASH1 tagging Rev (V5/V6/V7) | TGTACAATTGTTTCGTGATAATGTCTCTTATTAGTTGAAAGAGATTCAGTTATCCATGTAGCATAGGCCACTAGTGGATCTG |
| OET138 | ASH1 3`end cds Fw | AACACATACAAGATGTTTGAACG |
| OET214 | Kanr 5`end Rev | CTGATTGCCCGACATTATCGC |
| OET258 | DOA1 3UTR tagging Fw (V6) | GCTTGCAAACATCAAAAGGAGCTATGGGAACGTGCCAAGGTTTAAGGATATTTTCGACGATCTCTCCTAACCGCTCTAGAACTAGTGGAT |
| OET259 | DOA1 3UTR tagging Rev (V6) | GGGCAGAAAGAATTTTAAAGATTATTTGCTATCTAGACATTATGTGTTTTATATGATTGCTGTAAAAGTAGCATAGGCCACTAGTGGATCTG |
| OET260 | DOA1 3`end cds Fw | GGAACGTGCCAAGGTTTAAG |
| MDN1MS2F | MDN1 3UTR tagging Fw (V6/V7) | CACGATATAAGCGAACTACCCGAAATGCTTTCACTGATTTTGCGTCAATACTTTACAGACCTGGCATCCAGCTAAcgctctagaactagtggatc |
| MDN1MS2R | MDN1 3UTR tagging Rev (V6/V7) | TTTTTTTTCAGTTCCATGATTTTTTTGTTCCTTTGATTCGTGTAGTAAACCTCCTCTTCTTGGTTTTCACGATATACACTAGTGGATCTGATATCACC |
| SH | MDN1 3UTR tagging Fw MS2ORF | TTCACTGATTTTGCGTCAATACTTTACAGACCTGGCATCCAGCTAAGCCGCTCTAGAACTAGTGGATCC |
| SH | MDN1 3UTR tagging Rev MS2ORF | CCTTTGATTCGTGTAGTAAACCTCCTCTTCTTGGTTTTCACGATATAGCATAGGCCACTAGTGGATCTG |
| KanChRev | KanChRev | CTGATTGCCCGACATTATCGC |
| MDN1ChF | MDN1ChF | GATGGTATTTGCGAAGACCATG |
| GAL1MS2F | GAL1 3UTR tagging Fw (V6/V7) | TGCTGAGCTAGAAAATGCTATCATCGTCTCTAAACCAGCATTGGGCAGCTGTCTATATGAATTATAAGCCCCTGGCAATCGCGGG |
| GAL1MS2Fw | GAL1 3UTR tagging Fw (V5) | TTTTGTGATGCTAAAGTTATGAGTAGAAAAAAATGAGAAGTTGTTCTGAACAAAGTAAAAAAAGAAGTATACACTAGTGGATCTGATATCACC |
| GAL1MS2R | GAL1 3UTR tagging Rev (V5/V6/V7) | TTTTGTGATGCTAAAGTTATGAGTAGAAAAAAATGAGAAGTTGTTCTGAACAAAGTAAAAAAAGAAGTATACACTAGTGGATCTGATATCACC |
| GAL1ChF | GAL1ChF | GAAGCCCTTGCCAATGAGTTC |
| JG222 | ASH1 probe for Northern Blot | GTTTCGTGATAATGTCTCTTATTAGTTG |

MBSV6_U_variant.
(SEQ ID NO: 2)
TATTCTTTTGATTTATAAGGGATTTTGCCGATTTCGGCCTATTGGTTAAAAAATG

AGCTGATTTAACAAAAATTTAACGCGAATTTTAACAAAATATTAACGCTTACAA

TTTCCATTCGCCATTCAGGCTGCGCAACTGTTGGGAAGGGCGATCGGTGCGGGC

CTCTTCGCTATTACGCCAGCTGGCGAAAGGGGGATGTGCTGCAAGGCGATTAAG

TTGGGTAACGCCAGGGTTTTCCCAGTCACGACGTTGTAAAACGACGGCCAGTGA

GCGCGCGTAATACGACTCACTATAGGGCGAATTGGAGCTCCACCGCGGTGGCG

GCCGCTCTAGAACTAGTGGATCCCAGAGCCCCTGGCAATCGCGGGGAGACGC

AGGACTACCGCGTCTTCACTCTCGCTTGCGCGGTATACGCAGGGAGCAACGTCA

CCCAGGGCGACACAGAGGAATACCCTGTGTGGCCCCACGGTGCTACAAAGAAC

ATTCCGTATTGCTCACCAGTGTCACATGTGGAGGACTACCCCACAAGCGAGTCA

-continued

```
GGAAACCTTCGGGGCATCGCACCATTATCCCGAACAATCGACACGCAGGATTA
CCGCGTGGGACACTCTGTTCCCCGTCAAAATTGGACCATACCGGAGTCGGCTTA
CGTCATGCAGGATTACCGCATGCATGGTGCAGAATATCGGCATGTCTACTCGTA
CAGTCAAATCTACTCGTGTGGTCAGGACTACCGACCACTTCTATTCTATTCATCT
TTTCGGTTGTGCAGGTATTCTGCCGATGTACGAGAAGACGATTACGCTTCTCGA
CTACCTTCATCATACATGGTGTGCAGATGGCCGCCAAGTTTTTTGCCAATGGAG
GAATACCCCATTCTCTGTCAACCAACCCATGCAAAGTTTACACTCTGCTATGGC
AGCACTGTCGCAGAGGAATACCCTGCGAGCCAAAACGGCCCCCGGTGCGTGTA
TTGCATCTGCCTTGCGAGCATTCACAGGGACGAATACGCCCTGCCGTTGCATTA
CTTCAATATGGGTGCTCTGTCGTCGTCATCAGGACCATTTGCGCAGGACTACCG
CGCATATATCATCAGCACTCGTGCGGATACTTCTGGGATTCCTATTGTTACGCG
AGCTCAGGAATACCGAGCTCTGGCGACAGAGACCCTCACACGgAAGATCTATCG
ATCTCGACAACCCTTAATATAACTTCGTATAATGTATGCTATACGAAGTTATTA
GGTCTAGAGATCTGTTTAGCTTGCCTCGTCCCCGCCGGGTCACCCGGCCAGCGA
CATGGAGGCCCAGAATACCCTCCTTGACAGTCTTGACGTGCGCAGCTCAGGGGC
ATGATGTGACTGTCGCCCGTACATTTAGCCCATACATCCCCATGTATAATCATTT
GCATCCATACATTTTGATGGCCGCACGGCGCGAAGCAAAAATTACGGCTCCTCG
CTGCAGACCTGCGAGCAGGGAAACGCTCCCCTCACAGACGCGTTGAATTGTCCC
CACGCCGCGCCCCTGTAGAGAAATATAAAAGGTTAGGATTTGCCACTGAGGTTC
TTCTTTCATATACTTCCTTTTAAAATCTTGCTAGGATACAGTTCTCACATCACAT
CCGAACATAAACAACCATGGGTAAGGAAAAGACTCACGTTTCGAGGCCGCGAT
TAAATTCCAACATGGATGCTGATTTATATGGGTATAAATGGGCTCGCGATAATG
TCGGGCAATCAGGTGCGACAATCTATCGATTGTATGGGAAGCCCGATGCGCCA
GAGTTGTTTCTGAAACATGGCAAAGGTAGCGTTGCCAATGATGTTACAGATGAG
ATGGTCAGACTAAACTGGCTGACGGAATTTATGCCTCTTCCGACCATCAAGCAT
TTTATCCGTACTCCTGATGATGCATGGTTACTCACCACTGCGATCCCCGGCAAA
ACAGCATTCCAGGTATTAGAAGAATATCCTGATTCAGGTGAAAATATTGTTGAT
GCGCTGGCAGTGTTCCTGCGCCGGTTGCATTCGATTCCTGTTTGTAATTGTCCTT
TTAACAGCGATCGCGTATTTCGTCTCGCTCAGGCGCAATCACGAATGAATAACG
GTTTGGTTGATGCGAGTGATTTTGATGACGAGCGTAATGGCTGGCCTGTTGAAC
AAGTCTGGAAAGAAATGCATAAGCTTTTGCCATTCTCACCGGATTCAGTCGTCA
CTCATGGTGATTTCTCACTTGATAACCTTATTTTTGACGAGGGGAAATTAATAG
GTTGTATTGATGTTGGACGAGTCGGAATCGCAGACCGATACCAGGATCTTGCCA
TCCTATGGAACTGCCTCGGTGAGTTTTCTCCTTCATTACAGAAACGGCTTTTTCA
AAAATATGGTATTGATAATCCTGATATGAATAAATTGCAGTTTCATTTGATGCT
CGATGAGTTTTTCTAATCAGTACTGACAATAAAAAGATTCTTGTTTTCAAGAAC
TTGTCATTTGTATAGTTTTTTTATATTGTAGTTGTTCTATTTTAATCAAATGTTAG
CGTGATTTATATTTTTTTTCGCCTCGACATCATCTGCCCAGATGCGAAGTTAAGT
GCGCAGAAAGTAATATCATGCGTCAATCGTATGTGAATGCTGGTCGCTATACTG
CTGTCGATTCGATACTAACGCCGCCATCCAGTGTCGAAAACGAGCTCTCGAGAA
```

-continued

```
CCCTTAATATAACTTCGTATAATGTATGCTATACGAAGTTATTAGGTGATATCA
GATCCACTAGTGGCCTATGCGGTACCCAGCTTTTGTTCCCTTTAGTGAGGGTTAA
TTGCGCGCTTGGCGTAATCATGGTCATAGCTGTTTCCTGTGTGAAATTGTTATCC
GCTCACAATTCCACACAACATACGAGCCGGAAGCATAAAGTGTAAAGCCTGGG
GTGCCTAATGAGTGAGCTAACTCACATTAATTGCGTTGCGCTCACTGCCCGCTTT
CCAGTCGGGAAACCTGTCGTGCCAGCTGCATTAATGAATCGGCCAACGCGCGG
GGAGAGGCGGTTTGCGTATTGGGCGCTCTTCCGCTTCCTCGCTCACTGACTCGCT
GCGCTCGGTCGTTCGGCTGCGGCGAGCGGTATCAGCTCACTCAAAGGCGGTAAT
ACGGTTATCCACAGAATCAGGGGATAACGCAGGAAAGAACATGTGAGCAAAAG
GCCAGCAAAAGGCCAGGAACCGTAAAAAGGCCGCGTTGCTGGCGTTTTTCCAT
AGGCTCCGCCCCCCTGACGAGCATCACAAAAATCGACGCTCAAGTCAGAGGTG
GCGAAACCCGACAGGACTATAAAGATACCAGGCGTTTCCCCCTGGAAGCTCCCT
CGTGCGCTCTCCTGTTCCGACCCTGCCGCTTACCGGATACCTGTCCGCCTTTCTC
CCTTCGGGAAGCGTGGCGCTTTCTCATAGCTCACGCTGTAGGTATCTCAGTTCG
GTGTAGGTCGTTCGCTCCAAGCTGGGCTGTGTGCACGAACCCCCCGTTCAGCCC
GACCGCTGCGCCTTATCCGGTAACTATCGTCTTGAGTCCAACCCGGTAAGACAC
GACTTATCGCCACTGGCAGCAGCCACTGGTAACAGGATTAGCAGAGCGAGGTA
TGTAGGCGGTGCTACAGAGTTCTTGAAGTGGTGGCCTAACTACGGCTACACTAG
AAGGACAGTATTTGGTATCTGCGCTCTGCTGAAGCCAGTTACCTTCGGAAAAAG
AGTTGGTAGCTCTTGATCCGGCAAACAAACCACCGCTGGTAGCGGTGGTTTTTT
TGTTTGCAAGCAGCAGATTACGCGCAGAAAAAAAGGATCTCAAGAAGATCCTT
TGATCTTTTCTACGGGGTCTGACGCTCAGTGGAACGAAAACTCACGTTAAGGGA
TTTTGGTCATGAGATTATCAAAAAGGATCTTCACCTAGATCCTTTTAAATTAAA
AATGAAGTTTTAAATCAATCTAAAGTATATATGAGTAAACTTGGTCTGACAGTT
ACCAATGCTTAATCAGTGAGGCACCTATCTCAGCGATCTGTCTATTTCGTTCATC
CATAGTTGCCTGACTCCCCGTCGTGTAGATAACTACGATACGGGAGGGCTTACC
ATCTGGCCCCAGTGCTGCAATGATACCGCGAGACCCACGCTCACCGGCTCCAGA
TTTATCAGCAATAAACCAGCCAGCCGGAAGGGCCGAGCGCAGAAGTGGTCCTG
CAACTTTATCCGCCTCCATCCAGTCTATTAATTGTTGCCGGGAAGCTAGAGTAA
GTAGTTCGCCAGTTAATAGTTTGCGCAACGTTGTTGCCATTGCTACAGGCATCG
TGGTGTCACGCTCGTCGTTTGGTATGGCTTCATTCAGCTCCGGTTCCCAACGATC
AAGGCGAGTTACATGATCCCCCATGTTGTGCAAAAAAGCGGTTAGCTCCTTCGG
TCCTCCGATCGTTGTCAGAAGTAAGTTGGCCGCAGTGTTATCACTCATGGTTAT
GGCAGCACTGCATAATTCTCTTACTGTCATGCCATCCGTAAGATGCTTTTCTGTG
ACTGGTGAGTACTCAACCAAGTCATTCTGAGAATAGTGTATGCGGCGACCGAGT
TGCTCTTGCCCGGCGTCAATACGGGATAATACCGCGCCACATAGCAGAACTTTA
AAAGTGCTCATCATTGGAAAACGTTCTTCGGGGCGAAAACTCTCAAGGATCTTA
CCGCTGTTGAGATCCAGTTCGATGTAACCCACTCGTGCACCCAACTGATCTTCA
GCATCTTTTACTTTCACCAGCGTTTCTGGGTGAGCAAAAACAGGAAGGCAAAAT
GCCGCAAAAAAGGGAATAAGGGCGACACGGAAATGTTGAATACTCATACTCTT
CCTTTTTCAATATTATTGAAGCATTTATCAGGGTTATTGTCTCATGAGCGGATAC
```

-continued

ATATTTGAATGTATTTAGAAAAATAAACAAATAGGGGTTCCGCGCACATTTCCC

CGAAAAGTGCCACCTGACGCGCCCTGTAGCGGCGCATTAAGCGCGGCGGGTGT

GGTGGTTACGCGCAGCGTGACCGCTACACTTGCCAGCGCCCTAGCGCCCGCTCC

TTTCGCTTTCTTCCCTTCCTTTCTCGCCACGTTCGCCGGCTTTCCCCGTCAAGCTC

TAAATCGGGGGCTCCCTTTAGGGTTCCGATTTAGTGCTTTACGGCACCTCGACC

CCAAAAAACTTGATTAGGGTGATGGTTCACGTAGTGGGCCATCGCCCTGATAGA

CGGTTTTTCGCCCTTTGACGTTGGAGTCCACGTTCTTTAATAGTGGACTCTTGTT

CCAAACTGGAACAACACTCAACCCTATCTCGGTC

MBSV6_C_variant (SEQ ID NO: 3)
TATTCTTTTGATTTATAAGGGATTTTGCCGATTTCGGCCTATTGGTTAAAAAATG

AGCTGATTTAACAAAAATTTAACGCGAATTTTAACAAAATATTAACGCTTACAA

TTTCCATTCGCCATTCAGGCTGCGCAACTGTTGGGAAGGGCGATCGGTGCGGGC

CTCTTCGCTATTACGCCAGCTGGCGAAAGGGGATGTGCTGCAAGGCGATTAAG

TTGGGTAACGCCAGGGTTTTCCCAGTCACGACGTTGTAAAACGACGGCCAGTGA

GCGCGCGTAATACGACTCACTATAGGGCGAATTGGAGCTCCACCGCGGTGGCG

GCCGCTCTAGAACTAGTGGATCCCAGAGCCCCCTGGCAATCGCGGGGAGACGC

AGGACcACCGCGTCTTCACTCTCGCTTGCGCGGTATACGCAGGGAGCAACGTCA

CCCAGGGCGACACAGAGGAAcACCCTGTGTGGCCCCACGGTGCTACAAAGAAC

ATTCCGTATTGCTCACCAGTGTCACATGTGGAGGAcACCCCACAAGCGAGTCA

GGAAACCTTCGGGGCATCGCACCATTATCCCGAACAATCGACACGCAGGATcAC

CGCGTGGGACACTCTGTTCCCCGTCAAAATTGGACCATACCGGAGTCGGCTTAC

GTCATGCAGGATcACCGCATGCATGGTGCAGAATATCGGCATGTCTACTCGTAC

AGTCAAATCTACTCGTGTGGTCAGGAcCACCGACCACTTCTATTCTATTCATCTT

TTCGGTTGTGCAGGTATTCTGCCGATGTACGAGAAGACGATcACGCTTCTCGACT

ACCTTCATCATACATGGTGTGCAGATGGCCGCCAAGTTTTTTGCCAATGGAGGA

AcACCCCATTCTCTGTCAACCAACCCATGCAAAGTTTACACTCTGCTATGGCAGC

ACTGTCGCAGAGGAAcACCCTGCGAGCCAAAACGGCCCCCGGTGCGTGTATTGC

ATCTGCCTTGCGAGCATTCACAGGGACAAcACGCCCTGCCGTTGCATTACTTC

AATATGGGTGCTCTGTCGTCGTCATCAGGACCATTTGCGCAGGACcACCGCGCA

TATATCATCAGCACTCGTGCGGATACTTCTGGGATTCCTATTGTTACGCGAGCTC

AGGAAcACCGAGCTCTGGCGACAGAGACCCTCACACGgAAGATCTATCGATCTC

GACAACCCTTAATATAACTTCGTATAATGTATGCTATACGAAGTTATTAGGTCT

AGAGATCTGTTTAGCTTGCCTCGTCCCCGCCGGGTCACCCGGCCAGCGACATGG

AGGCCCAGAATACCCTCCTTGACAGTCTTGACGTGCGCAGCTCAGGGGCATGAT

GTGACTGTCGCCCGTACATTTAGCCCATACATCCCCATGTATAATCATTTGCATC

CATACATTTTGATGGCCGCACGGCGCGAAGCAAAAATTACGGCTCCTCGCTGCA

GACCTGCGAGCAGGGAAACGCTCCCCTCACAGACGCGTTGAATTGTCCCCACGC

CGCGCCCCTGTAGAGAAATATAAAAGGTTAGGATTTGCCACTGAGGTTCTTCTT

TCATATACTTCCTTTTAAAATCTTGCTAGGATACAGTTCTCACATCACATCCGAA

CATAAACAACCATGGGTAAGGAAAAGACTCACGTTTCGAGGCCGCGATTAAAT

-continued

```
TCCAACATGGATGCTGATTTATATGGGTATAAATGGGCTCGCGATAATGTCGGG

CAATCAGGTGCGACAATCTATCGATTGTATGGGAAGCCCGATGCGCCAGAGTTG

TTTCTGAAACATGGCAAAGGTAGCGTTGCCAATGATGTTACAGATGAGATGGTC

AGACTAAACTGGCTGACGGAATTTATGCCTCTTCCGACCATCAAGCATTTTATC

CGTACTCCTGATGATGCATGGTTACTCACCACTGCGATCCCCGGCAAAACAGCA

TTCCAGGTATTAGAAGAATATCCTGATTCAGGTGAAAATATTGTTGATGCGCTG

GCAGTGTTCCTGCGCCGGTTGCATTCGATTCCTGTTTGTAATTGTCCTTTTAACA

GCGATCGCGTATTTCGTCTCGCTCAGGCGCAATCACGAATGAATAACGGTTTGG

TTGATGCGAGTGATTTTGATGACGAGCGTAATGGCTGGCCTGTTGAACAAGTCT

GGAAAGAAATGCATAAGCTTTTGCCATTCTCACCGGATTCAGTCGTCACTCATG

GTGATTTCTCACTTGATAACCTTATTTTTGACGAGGGGAAATTAATAGGTTGTAT

TGATGTTGGACGAGTCGGAATCGCAGACCGATACCAGGATCTTGCCATCCTATG

GAACTGCCTCGGTGAGTTTTCTCCTTCATTACAGAAACGGCTTTTTCAAAAATAT

GGTATTGATAATCCTGATATGAATAAATTGCAGTTTCATTTGATGCTCGATGAG

TTTTTCTAATCAGTACTGACAATAAAAAGATTCTTGTTTTCAAGAACTTGTCATT

TGTATAGTTTTTTTATATTGTAGTTGTTCTATTTTAATCAAATGTTAGCGTGATTT

ATATTTTTTTCGCCTCGACATCATCTGCCCAGATGCGAAGTTAAGTGCGCAGA

AAGTAATATCATGCGTCAATCGTATGTGAATGCTGGTCGCTATACTGCTGTCGA

TTCGATACTAACGCCGCCATCCAGTGTCGAAAACGAGCTCTCGAGAACCCTTAA

TATAACTTCGTATAATGTATGCTATACGAAGTTATTAGGTGATATCAGATCCAC

TAGTGGCCTATGCGGTACCCAGCTTTTGTTCCCTTTAGTGAGGGTTAATTGCGCG

CTTGGCGTAATCATGGTCATAGCTGTTTCCTGTGTGAAATTGTTATCCGCTCACA

ATTCCACACAACATACGAGCCGGAAGCATAAAGTGTAAAGCCTGGGGTGCCTA

ATGAGTGAGCTAACTCACATTAATTGCGTTGCGCTCACTGCCCGCTTTCCAGTC

GGGAAACCTGTCGTGCCAGCTGCATTAATGAATCGGCCAACGCGCGGGGAGAG

GCGGTTTGCGTATTGGGCGCTCTTCCGCTTCCTCGCTCACTGACTCGCTGCGCTC

GGTCGTTCGGCTGCGGCGAGCGGTATCAGCTCACTCAAAGGCGGTAATACGGTT

ATCCACAGAATCAGGGGATAACGCAGGAAAGAACATGTGAGCAAAAGGCCAG

CAAAAGGCCAGGAACCGTAAAAAGGCCGCGTTGCTGGCGTTTTTCCATAGGCTC

CGCCCCCCTGACGAGCATCACAAAAATCGACGCTCAAGTCAGAGGTGGCGAAA

CCCGACAGGACTATAAAGATACCAGGCGTTTCCCCCTGGAAGCTCCCTCGTGCG

CTCTCCTGTTCCGACCCTGCCGCTTACCGGATACCTGTCCGCCTTTCTCCCTTCG

GGAAGCGTGGCGCTTTCTCATAGCTCACGCTGTAGGTATCTCAGTTCGGTGTAG

GTCGTTCGCTCCAAGCTGGGCTGTGTGCACGAACCCCCCGTTCAGCCCGACCGC

TGCGCCTTATCCGGTAACTATCGTCTTGAGTCCAACCCGGTAAGACACGACTTA

TCGCCACTGGCAGCAGCCACTGGTAACAGGATTAGCAGAGCGAGGTATGTAGG

CGGTGCTACAGAGTTCTTGAAGTGGTGGCCTAACTACGGCTACACTAGAAGGAC

AGTATTTGGTATCTGCGCTCTGCTGAAGCCAGTTACCTTCGGAAAAAGAGTTGG

TAGCTCTTGATCCGGCAAACAAACCACCGCTGGTAGCGGTGGTTTTTTTGTTTGC

AAGCAGCAGATTACGCGCAGAAAAAAAGGATCTCAAGAAGATCCTTTGATCTT

TTCTACGGGGTCTGACGCTCAGTGGAACGAAAACTCACGTTAAGGGATTTTGGT
```

-continued

CATGAGATTATCAAAAAGGATCTTCACCTAGATCCTTTTAAATTAAAAATGAAG

TTTTAAATCAATCTAAAGTATATATGAGTAAACTTGGTCTGACAGTTACCAATG

CTTAATCAGTGAGGCACCTATCTCAGCGATCTGTCTATTTCGTTCATCCATAGTT

GCCTGACTCCCCGTCGTGTAGATAACTACGATACGGGAGGGCTTACCATCTGGC

CCCAGTGCTGCAATGATACCGCGAGACCCACGCTCACCGGCTCCAGATTTATCA

GCAATAAACCAGCCAGCGGAAGGGCCGAGCGCAGAAGTGGTCCTGCAACTTT

ATCCGCCTCCATCCAGTCTATTAATTGTTGCCGGGAAGCTAGAGTAAGTAGTTC

GCCAGTTAATAGTTTGCGCAACGTTGTTGCCATTGCTACAGGCATCGTGGTGTC

ACGCTCGTCGTTTGGTATGGCTTCATTCAGCTCCGGTTCCCAACGATCAAGGCG

AGTTACATGATCCCCCATGTTGTGCAAAAAAGCGGTTAGCTCCTTCGGTCCTCC

GATCGTTGTCAGAAGTAAGTTGGCCGCAGTGTTATCACTCATGGTTATGGCAGC

ACTGCATAATTCTCTTACTGTCATGCCATCCGTAAGATGCTTTTCTGTGACTGGT

GAGTACTCAACCAAGTCATTCTGAGAATAGTGTATGCGGCGACCGAGTTGCTCT

TGCCCGGCGTCAATACGGGATAATACCGCGCCACATAGCAGAACTTTAAAAGT

GCTCATCATTGGAAAACGTTCTTCGGGGCGAAAACTCTCAAGGATCTTACCGCT

GTTGAGATCCAGTTCGATGTAACCCACTCGTGCACCCAACTGATCTTCAGCATC

TTTTACTTTCACCAGCGTTTCTGGGTGAGCAAAAACAGGAAGGCAAAATGCCGC

AAAAAAGGGAATAAGGGCGACACGGAAATGTTGAATACTCATACTCTTCCTTTT

TCAATATTATTGAAGCATTTATCAGGGTTATTGTCTCATGAGCGGATACATATTT

GAATGTATTTAGAAAAATAAACAAATAGGGGTTCCGCGCACATTTCCCCGAAA

AGTGCCACCTGACGCGCCCTGTAGCGGCGCATTAAGCGCGGCGGGTGTGGTGG

TTACGCGCAGCGTGACCGCTACACTTGCCAGCGCCCTAGCGCCCGCTCCTTTCG

CTTTCTTCCCTTCCTTTCTCGCCACGTTCGCCGGCTTTCCCCGTCAAGCTCTAAAT

CGGGGGCTCCCTTTAGGGTTCCGATTTAGTGCTTTACGGCACCTCGACCCCAAA

AAACTTGATTAGGGTGATGGTTCACGTAGTGGGCCATCGCCCTGATAGACGGTT

TTTCGCCCTTTGACGTTGGAGTCCACGTTCTTTAATAGTGGACTCTTGTTCCAAA

CTGGAACAACACTCAACCCTATCTCGGTC

YcpLac111CYC1p_MCP_NLS_2xGFP (SEQ ID NO: 4)
TACGCAAACCGCCTCTCCCCGCGCGTTGGCCGATTCATTAATGCAGCTGGCACG

ACAGGTTTCCCGACTGGAAAGCGGGCAGTGAGCGCAACGCAATTAATGTGAGT

TAGCTCACTCATTAGGCACCCCAGGCTTTACACTTTATGCTTCCGGCTCGTATGT

TGTGTGGAATTGTGAGCGGATAACAATTTCACACAGGAAACAGCTATGACCAT

GATTACGCCAAGCTTGCATGCCTGCAGGGAGCGTTGGTTGGTGGATCAAGCCCA

CGCGTAGGCAATCCTCGAGCAGATCCGCCGGGCGTGTATATAGCGTGGATGGC

CAGGCAACTTTAGTGCTGACACATACAGGCATATATATATGTGTGCGACGACAC

ATGATCATATGGCATGCATGTGCTCTGTATGTATATAAAACTCTTGTTTTCTTCT

TTTCTCTAAATATTCTTTCCTTATACATTAGGTCCTTTGTAGCATAAATTACTATA

CTTCTATAGACACGCAAACACAAATACACACACTAAATTAATAGGATCCATGCT

AGCCGTTAAAATGGCTTCTAACTTTACTCAGTTCGTTCTCGTCGACAATGGCGG

AACTGGCGACGTGACTGTCGCCCCAAGCAACTTCGCTAACGGGATCGCTGAATG

-continued

```
GATCAGCTCTAACTCGCGTTCACAGGCTTACAAAGTAACCTGTAGCGTTCGTCA

GAGCTCTGCGCAGAATCGCAAATACACCATCAAAGTCGAGGTGCCTAAAGGCG

CCTGGCGTTCGTACTTAAATATGGAACTAACCATTCCAATTTTCGCCACGAATTC

CGACTGCGAGCTTATTGTTAAGGCAATGCAAGGTCTCCTAAAAGATGGAAACCC

GATTCCCTCAGCAATCGCAGCAAACTCCGGCATCTACCCAAAAAAAAAAAGAA

AAGTTACCGGTTCTAAAGGTGAAGAATTATTCACTGGTGTTGTCCCAATTTTGG

TTGAATTAGATGGTGATGTTAATGGTCACAAATTTTCTGTCTCCGGTGAAGGTG

AAGGTGATGCTACTTACGGTAAATTGACCTTAAAATTTATTTGTACTACTGGTA

AATTGCCAGTTCCATGGCCAACCTTAGTCACTACTTTAACTTATGGTGTTCAATG

TTTTTCTAGATACCCAGATCATATGAAACAACATGACTTTTTCAAGTCTGCCATG

CCAGAAGGTTATGTTCAAGAAAGAACTATTTTTTTCAAAGATGACGGTAACTAC

AAGACCAGAGCTGAAGTCAAGTTTGAAGGTGATACCTTAGTTAATAGAATCAA

ATTAAAAGGTATTGATTTTAAAGAAGATGGTAACATTTTAGGTCACAAATTGGA

ATACAACTATAACTCTCACAATGTTTACATCATGGCTGACAAACAAAAGAATGG

TATCAAAGTTAACTTCAAAATTAGACACAACATTGAAGATGGTTCTGTTCAATT

AGCTGACCATTATCAACAAAATACTCCAATTGGTGATGGTCCAGTCTTGTTACC

AGACAACCATTACTTATCCACTCAATCTGCCTTATCCAAAGATCCAAACGAAAA

GAGAGACCACATGGTCTTGTTAGAATTTGTTACTGCTGCTGGTATTACCCATGG

TATGGATGAATTGTACAAATGTTTAAACTCTAAAGGTGAAGAATTATTCACTGG

TGTTGTCCCAATTTTGGTTGAATTAGATGGTGATGTTAATGGTCACAAATTTTCT

GTCTCCGGTGAAGGTGAAGGTGATGCTACTTACGGTAAATTGACCTTAAAATTT

ATTTGTACTACTGGTAAATTGCCAGTTCCATGGCCAACCTTAGTCACTACTTTAA

CTTATGGTGTTCAATGTTTTTCTAGATACCCAGATCATATGAAACAACATGACTT

TTTCAAGTCTGCCATGCCAGAAGGTTATGTTCAAGAAAGAACTATTTTTTTCAA

AGATGACGGTAACTACAAGACCAGAGCTGAAGTCAAGTTTGAAGGTGATACCT

TAGTTAATAGAATCGAATTAAAAGGTATTGATTTTAAAGAAGATGGTAACATTT

TAGGTCACAAATTGGAATACAACTATAACTCTCACAATGTTTACATCATGGCTG

ACAAACAAAAGAATGGTATCAAAGTTAACTTCAAAATTAGACACAACATTGAA

GATGGTTCTGTTCAATTAGCTGACCATTATCAACAAAATACTCCAATTGGTGAT

GGTCCAGTCTTGTTACCAGACAACCATTACTTATCCACTCAATCTGCCTTATCCA

AAGATCCAAACGAAAAGAGAGACCACATGGTCTTGTTAGAATTTGTTACTGCTG

CTGGTATTACCCATGGTATGGATGAATTGTACAAATAAGTTTAAACCCGCTGAT

CCTAGAGGGCCGCATCATGTAATTAGTTATGTCACGCTTACATTCACGCCCTCC

CCCCACATCCGCTCTAACCGAAAAGGAAGGAGTTAGACAACCTGAAGTCTAGG

TCCCTATTTATTTTTTATAGTTATGTTAGTATTAAGAACGTTATTTATATTTCAA

ATTTTTCTTTTTTTCTGTACAGACGCGTGTACGCATGTAACATTATACTGAAAA

CCTTGCTTGAGAAGGTTTTGGGACGCTCGAAGGCTTTAATTTGAGCTCGAATTC

ACTGGCCGTCGTTTTACAACGTCGTGACTGGGAAAACCCTGGCGTTACCCAACT

TAATCGCCTTGCAGCACATCCCCCTTTCGCCAGCTGGCGTAATAGCGAAGAGGC

CCGCACCGATCGCCCTTCCCAACAGTTGCGCAGCCTGAATGGCGAATGGCGCCT

GATGCGGTATTTTCTCCTTACGCATCTGTGCGGTATTTCACACCGCATAATCGCT
```

```
GGGCCATTCTCATGAAGAATATCTTGAATTTATTGTCATATTACTAGTTGGTGTG

GAAGTCCTAATATCGGTGATCAATATAGTGGTTGACATGCTGGCTAGTCAACAT

TGAGCCTTTTGATCATGCAAATATATTACGGTATTTTACAATCAAATATCAAACT

TAACTATTGACTTTATAACTTATTTAGGTGGTAACATTCTTATAAAAAGAAAA

AAATTACTGCAAAACAGTACTAGCTTTTAACTTGTATCCTAGGTTATCTATGCTG

TCTCACCATAGAGAATATTACCTATTTCAGAATGTATGTCCATGATTCGCCGGG

TAAATACATATAATACACAAATCTGGCTTAATAAAGTCTATAATATATCTCATA

AAGAAGTGCTAAATTGGCTAGTGCTATATATTTTTAAGAAAATTTCTTTTGACTA

AGTCCATATCGACTTTGTAAAAGTTCACATTAGCATACATATATTACACGAGCC

AGAAATAGTAACTTTTGCCTAAATCACAAATTGCAAAATTTAATTGCTTGCAAA

AGGTCACATGCTTATAATCAACTTTTTTAAAAATTTAAAATACTTTTTTATTTTTT

ATTTTTAAACATAAATGAAATAATTTATTTATTGTTTATGATTACCGAAACATAA

AACCTGCTCAAGAAAAGAAACTGTTTTGTCCTTGGAAAAAAAGCACTACCTA

GGAGCGGCCAAAATGCCGAGGCTTTCATAGCTTAAACTCTTTACAGAAAATAG

GCATTATAGATCAGTTCGAGTTTTCTTATTCTTCCTTCCGGTTTTATCGTCACAGT

TTTACAGTAAATAAGTATCACCTCTTAGAGTTCGATGATAAGCTGTCAAACATG

AGAATTAATTCCACATGTTAAAATAGTGAAGGAGCATGTTCGGCACACAGTGG

ACCGAACGTGGGGTAAGTGCACTAGGGTCCGGTTAAACGGATCTCGCATTGAT

GAGGCAACGCTAATTATCAACATATAGATTGTTATCTATCTGCATGAACACGAA

ATCTTTACTTGACGACTTGAGGCTGATGGTGTTTATGCAAAGAAACCACTGTGT

TTAATATGTGTCACTGTTTGATATTACTGTCAGCGTAGAAGATAATAGTAAAAG

CGGTTAATAAGTGTATTTGAGATAAGTGTGATAAAGTTTTTACAGCGAAAAGAC

GATAAATACAAGAAAATGATTACGAGGATACGGAGAGAGGTATGTACATGTGT

ATTTATATACTAAGCTGCCGGCGGTTGTTTGCAAGACCGAGAAAAGGCTAGCAA

GAATCGGGTCATTGTAGCGTATGCGCCTGTGAACATTCTCTTCAACAAGTTTGA

TTCCATTGCGGTGAAATGGTAAAAGTCAACCCCCTGCGATGTATATTTTCCTGT

ACAATCAATCAAAAAGCCAAATGATTTAGCATTATCTTTACATCTTGTTATTTTA

CAGATTTTATGTTTAGATCTTTTATGCTTGCTTTTCAAAAGGCTTGCAGGCAAGT

GCACAAACAATACTTAAATAAATACTACTCAGTAATAACCTATTTCTTAGCATT

TTTGACGAAATTTGCTATTTTGTTAGAGTCTTTTACACCATTTGTCTCCACACCT

CCGCTTACATCAACACCAATAACGCCATTTAATCTAAGCGCATCACCAACATTT

TCTGGCGTCAGTCCACCAGCTAACATAAAATGTAAGCTCTCGGGGCTCTCTTGC

CTTCCAACCCAGTCAGAAATCGAGTTCCAATCCAAAAGTTCACCTGTCCCACCT

GCTTCTGAATCAAACAAGGGAATAAACGAATGAGGTTTCTGTGAAGCTGCACT

GAGTAGTATGTTGCAGTCTTTTGGAAATACGAGTCTTTTAATAACTGGCAAACC

GAGGAACTCTTGGTATTCTTGCCACGACTCATCTCCATGCAGTTGGACGATCGA

TGATAAGCTGTCAAACATGAGAATTAATTCTACCCTATGAACATATTCCATTTT

GTAATTTCGTGTCGTTTCTATTATGAATTTCATTTATAAAGTTTATGTACAAATA

TCATAAAAAAGAGAATCTTTTTAAGCAAGGATTTTCTTAACTTCTTCGGCGAC

AGCATCACCGACTTCGGTGGTACTGTTGGAACCACCTAAATCACCAGTTCTGAT
```

-continued

```
ACCTGCATCCAAAACCTTTTTAACTGCATCTTCAATGGCCTTACCTTCTTCAGGC
AAGTTCAATGACAATTTCAACATCATTGCAGCAGACAAGATAGTGGCGATAGG
GTTGACCTTATTCTTTGGCAAATCTGGAGCAGAACCGTGGCATGGTTCGTACAA
ACCAAATGCGGTGTTCTTGTCTGGCAAAGAGGCCAAGGACGCAGATGGCAACA
AACCCAAGGAACCTGGGATAACGGAGGCTTCATCGGAGATGATATCACCAAAC
ATGTTGCTGGTGATTATAATACCATTTAGGTGGGTTGGGTTCTTAACTAGGATC
ATGGCGGCAGAATCAATCAATTGATGTTGAACCTTCAATGTAGGAAATTCGTTC
TTGATGGTTTCCTCCACAGTTTTTCTCCATAATCTTGAAGAGGCCAAAACATTAG
CTTTATCCAAGGACCAAATAGGCAATGGTGGCTCATGTTGTAGGGCCATGAAAG
CGGCCATTCTTGTGATTCTTTGCACTTCTGGAACGGTGTATTGTTCACTATCCCA
AGCGACACCATCACCATCGTCTTCCTTTCTCTTACCAAAGTAAATACCTCCCACT
AATTCTCTGACAACAACGAAGTCAGTACCTTTAGCAAATTGTGGCTTGATTGGA
GATAAGTCTAAAAGAGAGTCGGATGCAAAGTTACATGGTCTTAAGTTGGCGTA
CAATTGAAGTTCTTTACGGATTTTTAGTAAACCTTGTTCAGGTCTAACACTACCT
GTACCCCATTTAGGACCACCCACAGCACCTAACAAAACGGCATCAGCCTTCTTG
GAGGCTTCCAGCGCCTCATCTGGAAGTGGAACACCTGTAGCATCGATAGCAGC
ACCACCAATTAAATGATTTTCGAAATCGAACTTGACATTGGAACGAACATCAGA
AATAGCTTTAAGAACCTTAATGGCTTCGGCTGTGATTTCTTGACCAACGTGGTC
ACCTGGCAAAACGACGATCTTCTTAGGGGCAGACATTAGAATGGTATATCCTTG
AAATATATATATATATTGCTGAAATGTAAAAGGTAAGAAAAGTTAGAAAGTAA
GACGATTGCTAACCACCTATTGGAAAAAACAATAGGTCCTTAAATAATATTGTC
AACTTCAAGTATTGTGATGCAAGCATTTAGTCATGAACGCTTCTCTATTCTATAT
GAAAAGCCGGTTCCGGCGCTCTCACCTTTCCTTTTTCTCCCAATTTTTCAGTTGA
AAAAGGTATATGCGTCAGGCGACCTCTGAAATTAACAAAAAATTTCCAGTCATC
GAATTTGATTCTGTGCGATAGCGCCCCTGTGTGTTCTCGTTATGTTGAGGAAAA
AAATAATGGTTGCTAAGAGATTCGAACTCTTGCATCTTACGATACCTGAGTATT
CCCACAGTTAATTCTTGAAGACGAAAGGGCCTCGTGATACGCCTATTTTTATAG
GTTAATGTCATGATAATAATGGTTTCTTAGACGTCAGGTGGCACTTTTCGGGGA
AATGTGCGCGGAACCCCTATTTGTTTATTTTTCTAAATACATTCAAATATGTATC
CGCTCATGAGACAATAACCCTGATAAATGCTTCAATAATATTGAAAAAGGAAG
AGTATGAGTATTCAACATTTCCGTGTCGCCCTTATTCCCTTTTTTGCGGCATTTT
GCCTTCCTGTTTTTGCTCACCCAGAAACGCTGGTGAAAGTAAAAGATGCTGAAG
ATCAGTTGGGTGCACGAGTGGGTTACATCGAACTGGATCTCAACAGCGGTAAG
ATCCTTGAGAGTTTTCGCCCCGAAGAACGTTTTCCAATGATGAGCACTTTTAAA
GTTCTGCTATGTGGCGCGGTATTATCCCGTATTGACGCCGGGCAAGAGCAACTC
GGTCGCCGCATACACTATTCTCAGAATGACTTGGTTGAGTACTCACCAGTCACA
GAAAAGCATCTTACGGATGGCATGACAGTAAGAGAATTATGCAGTGCTGCCAT
AACCATGAGTGATAACACTGCGGCCAACTTACTTCTGACAACGATCGGAGGAC
CGAAGGAGCTAACCGCTTTTTTGCACAACATGGGGGATCATGTAACTCGCCTTG
ATCGTTGGGAACCGGAGCTGAATGAAGCCATACCAAACGACGAGCGTGACACC
ACGATGCCTGTAGCAATGGCAACAACGTTGCGCAAACTATTAACTGGCGAACT
```

-continued

ACTTACTCTAGCTTCCCGGCAACAATTAATAGACTGGATGGAGGCGGATAAAGT

TGCAGGACCACTTCTGCGCTCGGCCCTTCCGGCTGGCTGGTTTATTGCTGATAA

ATCTGGAGCCGGTGAGCGTGGGTCTCGCGGTATCATTGCAGCACTGGGGCCAG

ATGGTAAGCCCTCCCGTATCGTAGTTATCTACACGACGGGGAGTCAGGCAACTA

TGGATGAACGAAATAGACAGATCGCTGAGATAGGTGCCTCACTGATTAAGCAT

TGGTAACTGTCAGACCAAGTTTACTCATATATACTTTAGATTGATTTAAAACTTC

ATTTTTAATTTAAAAGGATCTAGGTGAAGATCCTTTTTGATAATCTCATGACCAA

AATCCCTTAACGTGAGTTTTCGTTCCACTGAGCGTCAGACCCCGTAGAAAAGAT

CAAAGGATCTTCTTGAGATCCTTTTTTTCTGCGCGTAATCTGCTGCTTGCAAACA

AAAAAACCACCGCTACCAGCGGTGGTTTGTTTGCCGGATCAAGAGCTACCAACT

CTTTTTCCGAAGGTAACTGGCTTCAGCAGAGCGCAGATACCAAATACTGTTCTT

CTAGTGTAGCCGTAGTTAGGCCACCACTTCAAGAACTCTGTAGCACCGCCTACA

TACCTCGCTCTGCTAATCCTGTTACCAGTGGCTGCTGCCAGTGGCGATAAGTCG

TGTCTTACCGGGTTGGACTCAAGACGATAGTTACCGGATAAGGCGCAGCGGTCG

GGCTGAACGGGGGGTTCGTGCACACAGCCCAGCTTGGAGCGAACGACCTACAC

CGAACTGAGATACCTACAGCGTGAGCTATGAGAAAGCGCCACGCTTCCCGAAG

GGAGAAAGGCGGACAGGTATCCGGTAAGCGGCAGGGTCGGAACAGGAGAGCG

CACGAGGGAGCTTCCAGGGGGAAACGCCTGGTATCTTTATAGTCCTGTCGGGTT

TCGCCACCTCTGACTTGAGCGTCGATTTTTGTGATGCTCGTCAGGGGGGCGGAG

CCTATGGAAAAACGCCAGCAACGCGGCCTTTTTACGGTTCCTGGCCTTTTGCTG

GCCTTTTGCTCACATGTTCTTTCCTGCGTTATCCCCTGATTCTGTGGATAACCGT

ATTACCGCCTTTGAGTGAGCTGATACCGCTCGCCGCAGCCGAACGACCGAGCGC

AGCGAGTCAGTGAGCGAGGAAGCGGAAGAGCGCCCAA (SEQ ID NO: 32)
TACGCAAACCGCCTCTCCCCGCGCGTTGGCCGATTCATTAATGCAGCT

GGCACGACAGGTTTCCCGACTGGAAAGCGGGCAGTGAGCGCAACGCAATTAAT

GTGAGTTAGCTCACTCATTAGGCACCCCAGGCTTTACACTTTATGCTTCCGGCTC

GTATGTTGTGTGGAATTGTGAGCGGATAACAATTTCACACAGGAAACAGCTATG

ACCATGATTACGCCAAGCTTGCATGCCTGCAGGGAGCGTTGGTTGGTGGATCAA

GCCCACGCGTAGGCAATCCTCGAGCAGATCCGCCGGGCGTGTATATAGCGTGG

ATGGCCAGGCAACTTTAGTGCTGACACATACAGGCATATATATATGTGTGCGAC

GACACATGATCATATGGCATGCATGTGCTCTGTATGTATATAAAACTCTTGTTTT

CTTCTTTTCTCTAAATATTCTTTCCTTATACATTAGGTCCTTTGTAGCATAAATTA

CTATACTTCTATAGACACGCAAACACAAATACACACACTAAATTAATAGGATCC

ATGCTAGCCGTTAAAATGGCTTCTAACTTTACTCAGTTCGTTCTCGTCGACAATG

GCGGAACTGGCGACGTGACTGTCGCCCCAAGCAACTTCGCTAACGGGATCGCT

GAATGGATCAGCTCTAACTCGCGTTCACAGGCTTACAAAGTAACCTGTAGCGTT

CGTCAGAGCTCTGCGCAGAATCGCAAATACACCATCAAAGTCGAGGTGCCTAA

AGGCGCCTGGCGTTCGTACTTAAATATGGAACTAACCATTCCAATTTTCGCCAC

GAATTCCGACTGCGAGCTTATTGTTAAGGCAATGCAAGGTCTCCTAAAAGATGG

AAACCCGATTCCCTCAGCAATCGCAGCAAACTCCGGCATCTACACCGGTTCTAA

-continued

```
AGGTGAAGAATTATTCACTGGTGTTGTCCCAATTTTGGTTGAATTAGATGGTGA
TGTTAATGGTCACAAATTTTCTGTCTCCGGTGAAGGTGAAGGTGATGCTACTTA
CGGTAAATTGACCTTAAAATTTATTTGTACTACTGGTAAATTGCCAGTTCCATGG
CCAACCTTAGTCACTACTTTAACTTATGGTGTTCAATGTTTTTCTAGATACCCAG
ATCATATGAAACAACATGACTTTTTCAAGTCTGCCATGCCAGAAGGTTATGTTC
AAGAAAGAACTATTTTTTTCAAAGATGACGGTAACTACAAGACCAGAGCTGAA
GTCAAGTTTGAAGGTGATACCTTAGTTAATAGAATCAAATTAAAAGGTATTGAT
TTTAAAGAAGATGGTAACATTTTAGGTCACAAATTGGAATACAACTATAACTCT
CACAATGTTTACATCATGGCTGACAAACAAAAGAATGGTATCAAAGTTAACTTC
AAAATTAGACACAACATTGAAGATGGTTCTGTTCAATTAGCTGACCATTATCAA
CAAAATACTCCAATTGGTGATGGTCCAGTCTTGTTACCAGACAACCATTACTTA
TCCACTCAATCTGCCTTATCCAAAGATCCAAACGAAAAGAGAGACCACATGGTC
TTGTTAGAATTTGTTACTGCTGCTGGTATTACCCATGGTATGGATGAATTGTACA
AATGTTTAAACTCTAAAGGTGAAGAATTATTCACTGGTGTTGTCCCAATTTTGGT
TGAATTAGATGGTGATGTTAATGGTCACAAATTTTCTGTCTCCGGTGAAGGTGA
AGGTGATGCTACTTACGGTAAATTGACCTTAAAATTTATTTGTACTACTGGTAA
ATTGCCAGTTCCATGGCCAACCTTAGTCACTACTTTAACTTATGGTGTTCAATGT
TTTTCTAGATACCCAGATCATATGAAACAACATGACTTTTTCAAGTCTGCCATGC
CAGAAGGTTATGTTCAAGAAAGAACTATTTTTTTCAAAGATGACGGTAACTACA
AGACCAGAGCTGAAGTCAAGTTTGAAGGTGATACCTTAGTTAATAGAATCGAA
TTAAAAGGTATTGATTTTAAAGAAGATGGTAACATTTTAGGTCACAAATTGGAA
TACAACTATAACTCTCACAATGTTTACATCATGGCTGACAAACAAAAGAATGGT
ATCAAAGTTAACTTCAAAATTAGACACAACATTGAAGATGGTTCTGTTCAATTA
GCTGACCATTATCAACAAAATACTCCAATTGGTGATGGTCCAGTCTTGTTACCA
GACAACCATTACTTATCCACTCAATCTGCCTTATCCAAAGATCCAAACGAAAAG
AGAGACCACATGGTCTTGTTAGAATTTGTTACTGCTGCTGGTATTACCCATGGT
ATGGATGAATTGTACAAATACCCCAAAAAAAAAAAGAAAAGTTtaaGTTTAAACC
CGCTGATCCTAGAGGGCCGCATCATGTAATTAGTTATGTCACGCTTACATTCAC
GCCCTCCCCCCACATCCGCTCTAACCGAAAAGGAAGGAGTTAGACAACCTGAA
GTCTAGGTCCCTATTTATTTTTTTATAGTTATGTTAGTATTAAGAACGTTATTTAT
ATTTCAAATTTTTCTTTTTTTTCTGTACAGACGCGTGTACGCATGTAACATTATA
CTGAAAACCTTGCTTGAGAAGGTTTTGGGACGCTCGAAGGCTTTAATTTGCAAG
CTGCGGCCCTGCATTGGCGCGTGTACGCATGTAACATTATACTGAAAACCTTGC
TTGAGAAGGTTTTGGGACGCTCGAAGGCTTTAATTTGAGCTCGAATTCACTGGC
CGTCGTTTTACAACGTCGTGACTGGGAAAACCCTGGCGTTACCCAACTTAATCG
CCTTGCAGCACATCCCCCTTTCGCCAGCTGGCGTAATAGCGAAGAGGCCCGCAC
CGATCGCCCTTCCCAACAGTTGCGCAGCCTGAATGGCGAATGGCGCCTGATGCG
GTATTTTCTCCTTACGCATCTGTGCGGTATTTCACACCGCATAATCGCTGGGCCA
TTCTCATGAAGAATATCTTGAATTTATTGTCATATTACTAGTTGGTGTGGAAGTC
CTAATATCGGTGATCAATATAGTGGTTGACATGCTGGCTAGTCAACATTGAGCC
```

-continued

```
TTTTGATCATGCAAATATATTACGGTATTTTACAATCAAATATCAAACTTAACTA

TTGACTTTATAACTTATTTAGGTGGTAACATTCTTATAAAAAAGAAAAAAATTA

CTGCAAAACAGTACTAGCTTTTAACTTGTATCCTAGGTTATCTATGCTGTCTCAC

CATAGAGAATATTACCTATTTCAGAATGTATGTCCATGATTCGCCGGGTAAATA

CATATAATACACAAATCTGGCTTAATAAAGTCTATAATATATCTCATAAAGAAG

TGCTAAATTGGCTAGTGCTATATATTTTTAAGAAAATTTCTTTTGACTAAGTCCA

TATCGACTTTGTAAAAGTTCACATTAGCATACATATATTACACGAGCCAGAAAT

AGTAACTTTTGCCTAAATCACAAATTGCAAAATTTAATTGCTTGCAAAAGGTCA

CATGCTTATAATCAACTTTTTTAAAAATTTAAAATACTTTTTTATTTTTTATTTTT

AAACATAAATGAAATAATTTATTTATTGTTTATGATTACCGAAACATAAAACCT

GCTCAAGAAAAGAAACTGTTTTGTCCTTGGAAAAAAAGCACTACCTAGGAGC

GGCCAAAATGCCGAGGCTTTCATAGCTTAAACTCTTTACAGAAAATAGGCATTA

TAGATCAGTTCGAGTTTTCTTATTCTTCCTTCCGGTTTTATCGTCACAGTTTTACA

GTAAATAAGTATCACCTCTTAGAGTTCGATGATAAGCTGTCAAACATGAGAATT

AATTCCACATGTTAAAATAGTGAAGGAGCATGTTCGGCACACAGTGGACCGAA

CGTGGGTAAGTGCACTAGGGTCCGGTTAAACGGATCTCGCATTGATGAGGCA

ACGCTAATTATCAACATATAGATTGTTATCTATCTGCATGAACACGAAATCTTT

ACTTGACGACTTGAGGCTGATGGTGTTTATGCAAAGAAACCACTGTGTTTAATA

TGTGTCACTGTTTGATATTACTGTCAGCGTAGAAGATAATAGTAAAAGCGGTTA

ATAAGTGTATTTGAGATAAGTGTGATAAAGTTTTTACAGCGAAAAGACGATAA

ATACAAGAAAATGATTACGAGGATACGGAGAGAGGTATGTACATGTGTATTTA

TATACTAAGCTGCCGGCGGTTGTTTGCAAGACCGAGAAAAGGCTAGCAAGAAT

CGGGTCATTGTAGCGTATGCGCCTGTGAACATTCTCTTCAACAAGTTTGATTCCA

TTGCGGTGAAATGGTAAAAGTCAACCCCCTGCGATGTATATTTTCCTGTACAAT

CAATCAAAAAGCCAAATGATTTAGCATTATCTTTACATCTTGTTATTTTACAGAT

TTTATGTTTAGATCTTTTATGCTTGCTTTTCAAAAGGCTTGCAGGCAAGTGCACA

AACAATACTTAAATAAATACTACTCAGTAATAACCTATTTCTTAGCATTTTTGAC

GAAATTTGCTATTTTGTTAGAGTCTTTTACACCATTTGTCTCCACACCTCCGCTT

ACATCAACACCAATAACGCCATTTAATCTAAGCGCATCACCAACATTTTCTGGC

GTCAGTCCACCAGCTAACATAAAATGTAAGCTCTCGGGGCTCTCTTGCCTTCCA

ACCCAGTCAGAAATCGAGTTCCAATCCAAAAGTTCACCTGTCCCACCTGCTTCT

GAATCAAACAAGGGAATAAACGAATGAGGTTTCTGTGAAGCTGCACTGAGTAG

TATGTTGCAGTCTTTTGGAAATACGAGTCTTTTAATAACTGGCAAACCGAGGAA

CTCTTGGTATTCTTGCCACGACTCATCTCCATGCAGTTGGACGATCGATGATAA

GCTGTCAAACATGAGAATTAATTCTACCCTATGAACATATTCCATTTTGTAATTT

CGTGTCGTTTCTATTATGAATTTCATTTATAAAGTTTATGTACAAATATCATAAA

AAAAGAGAATCTTTTTAAGCAAGGATTTTCTTAACTTCTTCGGCGACAGCATCA

CCGACTTCGGTGGTACTGTTGGAACCACCTAAATCACCAGTTCTGATACCTGCA

TCCAAAACCTTTTTAACTGCATCTTCAATGGCCTTACCTTCTTCAGGCAAGTTCA

ATGACAATTTCAACATCATTGCAGCAGACAAGATAGTGGCGATAGGGTTGACCT

TATTCTTTGGCAAATCTGGAGCAGAACCGTGGCATGGTTCGTACAAACCAAATG
```

```
CGGTGTTCTTGTCTGGCAAAGAGGCCAAGGACGCAGATGGCAACAAACCCAAG

GAACCTGGGATAACGGAGGCTTCATCGGAGATGATATCACCAAACATGTTGCT

GGTGATTATAATACCATTTAGGTGGGTTGGGTTCTTAACTAGGATCATGGCGGC

AGAATCAATCAATTGATGTTGAACCTTCAATGTAGGAAATTCGTTCTTGATGGT

TTCCTCCACAGTTTTTCTCCATAATCTTGAAGAGGCCAAAACATTAGCTTTATCC

AAGGACCAAATAGGCAATGGTGGCTCATGTTGTAGGGCCATGAAAGCGGCCAT

TCTTGTGATTCTTTGCACTTCTGGAACGGTGTATTGTTCACTATCCCAAGCGACA

CCATCACCATCGTCTTCCTTTCTCTTACCAAAGTAAATACCTCCCACTAATTCTC

TGACAACAACGAAGTCAGTACCTTTAGCAAATTGTGGCTTGATTGGAGATAAGT

CTAAAAGAGAGTCGGATGCAAAGTTACATGGTCTTAAGTTGGCGTACAATTGA

AGTTCTTTACGGATTTTTAGTAAACCTTGTTCAGGTCTAACACTACCTGTACCCC

ATTTAGGACCACCCACAGCACCTAACAAAACGGCATCAGCCTTCTTGGAGGCTT

CCAGCGCCTCATCTGGAAGTGGAACACCTGTAGCATCGATAGCAGCACCACCA

ATTAAATGATTTTCGAAATCGAACTTGACATTGGAACGAACATCAGAAATAGCT

TTAAGAACCTTAATGGCTTCGGCTGTGATTTCTTGACCAACGTGGTCACCTGGC

AAAACGACGATCTTCTTAGGGGCAGACATTAGAATGGTATATCCTTGAAATATA

TATATATATTGCTGAAATGTAAAAGGTAAGAAAAGTTAGAAAGTAAGACGATT

GCTAACCACCTATTGGAAAAAACAATAGGTCCTTAAATAATATTGTCAACTTCA

AGTATTGTGATGCAAGCATTTAGTCATGAACGCTTCTCTATTCTATATGAAAAG

CCGGTTCCGGCGCTCTCACCTTTCCTTTTTCTCCCAATTTTTCAGTTGAAAAAGG

TATATGCGTCAGGCGACCTCTGAAATTAACAAAAAATTTCCAGTCATCGAATTT

GATTCTGTGCGATAGCGCCCCTGTGTGTTCTCGTTATGTTGAGGAAAAAAATAA

TGGTTGCTAAGAGATTCGAACTCTTGCATCTTACGATACCTGAGTATTCCCACA

GTTAATTCTTGAAGACGAAAGGGCCTCGTGATACGCCTATTTTTATAGGTTAAT

GTCATGATAATAATGGTTTCTTAGACGTCAGGTGGCACTTTTCGGGGAAATGTG

CGCGGAACCCCTATTTGTTTATTTTTCTAAATACATTCAAATATGTATCCGCTCA

TGAGACAATAACCCTGATAAATGCTTCAATAATATTGAAAAAGGAAGAGTATG

AGTATTCAACATTTCCGTGTCGCCCTTATTCCCTTTTTTGCGGCATTTTGCCTTCC

TGTTTTTGCTCACCCAGAAACGCTGGTGAAAGTAAAAGATGCTGAAGATCAGTT

GGGTGCACGAGTGGGTTACATCGAACTGGATCTCAACAGCGGTAAGATCCTTG

AGAGTTTTCGCCCCGAAGAACGTTTTCCAATGATGAGCACTTTTAAAGTTCTGC

TATGTGGCGCGGTATTATCCCGTATTGACGCCGGGCAAGAGCAACTCGGTCGCC

GCATACACTATTCTCAGAATGACTTGGTTGAGTACTCACCAGTCACAGAAAAGC

ATCTTACGGATGGCATGACAGTAAGAGAATTATGCAGTGCTGCCATAACCATGA

GTGATAACACTGCGGCCAACTTACTTCTGACAACGATCGGAGGACCGAAGGAG

CTAACCGCTTTTTTGCACAACATGGGGGATCATGTAACTCGCCTTGATCGTTGG

GAACCGGAGCTGAATGAAGCCATACCAAACGACGAGCGTGACACCACGATGCC

TGTAGCAATGGCAACAACGTTGCGCAAACTATTAACTGGCGAACTACTTACTCT

AGCTTCCCGGCAACAATTAATAGACTGGATGGAGGCGGATAAAGTTGCAGGAC

CACTTCTGCGCTCGGCCCTTCCGGCTGGCTGGTTTATTGCTGATAAATCTGGAGC
```

-continued
CGGTGAGCGTGGGTCTCGCGGTATCATTGCAGCACTGGGGCCAGATGGTAAGC

CCTCCCGTATCGTAGTTATCTACACGACGGGGAGTCAGGCAACTATGGATGAAC

GAAATAGACAGATCGCTGAGATAGGTGCCTCACTGATTAAGCATTGGTAACTGT

CAGACCAAGTTTACTCATATATACTTTAGATTGATTTAAAACTTCATTTTTAATT

TAAAAGGATCTAGGTGAAGATCCTTTTTGATAATCTCATGACCAAAATCCCTTA

ACGTGAGTTTTCGTTCCACTGAGCGTCAGACCCCGTAGAAAAGATCAAAGGATC

TTCTTGAGATCCTTTTTTTCTGCGCGTAATCTGCTGCTTGCAAACAAAAAAACCA

CCGCTACCAGCGGTGGTTTGTTTGCCGGATCAAGAGCTACCAACTCTTTTTCCG

AAGGTAACTGGCTTCAGCAGAGCGCAGATACCAAATACTGTTCTTCTAGTGTAG

CCGTAGTTAGGCCACCACTTCAAGAACTCTGTAGCACCGCCTACATACCTCGCT

CTGCTAATCCTGTTACCAGTGGCTGCTGCCAGTGGCGATAAGTCGTGTCTTACC

GGGTTGGACTCAAGACGATAGTTACCGGATAAGGCGCAGCGGTCGGGCTGAAC

GGGGGGTTCGTGCACACAGCCCAGCTTGGAGCGAACGACCTACACCGAACTGA

GATACCTACAGCGTGAGCTATGAGAAAGCGCCACGCTTCCCGAAGGGAGAAAG

GCGGACAGGTATCCGGTAAGCGGCAGGGTCGGAACAGGAGAGCGCACGAGGG

AGCTTCCAGGGGGAAACGCCTGGTATCTTTATAGTCCTGTCGGGTTTCGCCACC

TCTGACTTGAGCGTCGATTTTTGTGATGCTCGTCAGGGGGCGGAGCCTATGGA

AAAACGCCAGCAACGCGGCCTTTTTACGGTTCCTGGCCTTTTGCTGGCCTTTTGC

TCACATGTTCTTTCCTGCGTTATCCCCTGATTCTGTGGATAACCGTATTACCGCC

TTTGAGTGAGCTGATACCGCTCGCCGCAGCCGAACGACCGAGCGCAGCGAGTC

AGTGAGCGAGGAAGCGGAAGAGCGCCCAA

REFERENCES

Bernardi, A., and Spahr, P. F. (1972). Nucleotide sequence at the binding site for coat protein on RNA of bacteriophage R17. Proceedings of the National Academy of Sciences of the United States of America 69, 3033-3037.

Bertrand, E., Chartrand, P., Schaefer, M., Shenoy, S. M., Singer, R. H., and Long, R. M. (1998). Localization of ASH1 mRNA particles in living yeast. Molecular cell 2, 437-445.

Caponigro, G., Muhlrad, D., and Parker, R. (1993). A small segment of the MAT alpha 1 transcript promotes mRNA decay in Saccharomyces cerevisiae: a stimulatory role for rare codons. Molecular and cellular biology 13, 5141-5148.

Chao, J. A., Patskovsky, Y., Almo, S. C., and Singer, R. H. (2008). Structural basis for the coevolution of a viral RNA-protein complex. Nature structural & molecular biology 15, 103-105.

Eser, P., Demel, C., Maier, K. C., Schwalb, B., Pirkl, N., Martin, D. E., Cramer, P., and Tresch, A. (2014). Periodic mRNA synthesis and degradation co-operate during cell cycle gene expression. Molecular systems biology 10, 717.

Fusco, D., Accornero, N., Lavoie, B., Shenoy, S. M., Blanchard, J. M., Singer, R. H., and Bertrand, E. (2003). Single mRNA molecules demonstrate probabilistic movement in living mammalian cells. Current biology: CB 13, 161-167.

Garcia, J. F., and Parker, R. (2015). MS2 coat protein bound to yeast mRNAs block 5' to 3' degradation and trap mRNA decay products: implications for the localization of mRNAs by MS2-MCP system. RNA (New York, N.Y.)

Garcia, J. F., and Parker, R. (2016). Ubiquitous accumulation of 3' mRNA decay fragments in Saccharomyces cerevisiae mRNAs with chromosomally integrated MS2 arrays. RNA (New York, N.Y. 22, 657-659).

Grunwald, D., and Singer, R. H. (2010). In vivo imaging of labelled endogenous beta-actin mRNA during nucleocytoplasmic transport. Nature 467, 604-607.

Guet, D., Burns, L. T., Maji, S., Boulanger, J., Hersen, P., Wente, S. R., Salamero, J., and Dargemont, C. (2015). Combining Spinach-tagged RNA and gene localization to image gene expression in live yeast. Nature communications 6, 8882.

Haim-Vilmovsky, L., Gadir, N., Herbst, R. H., and Gerst, J. E. (2011). A genomic integration method for the simultaneous visualization of endogenous mRNAs and their translation products in living yeast. RNA (New York, N.Y. 17, 2249-2255).

Haim-Vilmovsky, L., and Gerst, J. E. (2009). m-TAG: a PCR-based genomic integration method to visualize the localization of specific endogenous mRNAs in vivo in yeast. Nature protocols 4, 1274-1284.

Haim, L., Zipor, G., Aronov, S., and Gerst, J. E. (2007). A genomic integration method to visualize localization of endogenous mRNAs in living yeast. Nature methods 4, 409-412.

Haimovich, G., Medina, D. A., Causse, S. Z., Garber, M., Millan-Zambrano, G., Barkai, O., Chavez, S., Perez-Ortin, J. E., Darzacq, X., and Choder, M. (2013). Gene expression is circular: factors for mRNA degradation also foster mRNA synthesis. Cell 153, 1000-1011.

Haimovich, G., Zabezhinsky, D., Haas, B., Slobodin, B., Purushothaman, P., Fan, L., Levin, J. Z., Nusbaum, C., and Gerst, J. E. (2016). Use of the MS2 aptamer and coat protein for RNA localization in yeast: A response to "MS2 coat proteins bound to yeast mRNAs block 5' to 3' degradation and trap mRNA decay products: implications for the localization of mRNAs by MS2-MCP system". RNA (New York, N.Y. 22, 660-666).

Heinrich, S., Sidler, C. L., Azzalin, C. M., and Weis, K. (2017). Stem-loop RNA labeling can affect nuclear and cytoplasmic mRNA processing. RNA (New York, N.Y. 23, 134-141.

Heym, R. G., and Niessing, D. (2012). Principles of mRNA transport in yeast. Cellular and molecular life sciences: CMLS 69, 1843-1853.

Hocine, S., Raymond, P., Zenklusen, D., Chao, J. A., and Singer, R. H. (2013). Single-molecule analysis of gene expression using two-color RNA labeling in live yeast. Nature methods 10, 119-121.

Hsu, C., Scherrer, S., Buetti-Dinh, A., Ratna, P., Pizzolato, J., Jaquet, V., and Becskei, A. (2012). Stochastic signalling rewires the interaction map of a multiple feedback network during yeast evolution. Nature communications 3, 682.

Ingolia, N. T., Ghaemmaghami, S., Newman, J. R. S., and Weissman, J. S. (2009). Genome-Wide Analysis in Vivo of Translation with Nucleotide Resolution Using Ribosome Profiling. Science (New York, N.Y. 324, 218-223).

Kshirsagar, M., and Parker, R. (2004). Identification of Edc3p as an enhancer of mRNA decapping in *Saccharomyces cerevisiae*. Genetics 166, 729-739.

Larson, D. R., Zenklusen, D., Wu, B., Chao, J. A., and Singer, R. H. (2011). Real-time observation of transcription initiation and elongation on an endogenous yeast gene. Science (New York, N.Y. 332, 475-478).

Lohr, D., Venkov, P., and Zlatanova, J. (1995). Transcriptional regulation in the yeast GAL gene family: a complex genetic network. FASEB journal: official publication of the Federation of American Societies for Experimental Biology 9, 777-787.

Long, R. M., Chartrand, P., Gu, W., Meng, X. H., Schaefer, M. R., and Singer, R. H. (1997a). Characterization of transport and localization of ASH1 mRNA in yeast. Molecular biology of the cell 8, 2060-2060.

Long, R. M., Singer, R. H., Meng, X., Gonzalez, I., Nasmyth, K., and Jansen, R. P. (1997b). Mating type switching in yeast controlled by asymmetric localization of ASH1 mRNA. Science (New York, N.Y. 277, 383-387).

Lowary, P. T., and Uhlenbeck, O. C. (1987). An RNA mutation that increases the affinity of an RNA-protein interaction. Nucleic acids research 15, 10483-10493.

Mumberg, D., Muller, R., and Funk, M. (1995). Yeast vectors for the controlled expression of heterologous proteins in different genetic backgrounds. Gene 156, 119-122.

Nelles, D. A., Fang, M. Y., O'Connell, M. R., Xu, J. L., Markmiller, S. J., Doudna, J. A., and Yeo, G. W. (2016). Programmable RNA Tracking in Live Cells with CRISPR/Cas9. Cell 165, 488-496.

Pereira, G., and Schiebel, E. (2001). The role of the yeast spindle pole body and the mammalian centrosome in regulating late mitotic events. Current opinion in cell biology 13, 762-769.

Shav-Tal, Y., Darzacq, X., Shenoy, S. M., Fusco, D., Janicki, S. M., Spector, D. L., and Singer, R. H. (2004). Dynamics of single mRNPs in nuclei of living cells. Science (New York, N.Y. 304, 1797-1800.

Sheth, U., and Parker, R. (2003). Decapping and decay of messenger RNA occur in cytoplasmic processing bodies. Science (New York, N.Y. 300, 805-808).

Simpson, C. E., Lui, J., Kershaw, C. J., Sims, P. F., and Ashe, M. P. (2014). mRNA localization to P-bodies in yeast is bi-phasic with many mRNAs captured in a late Bfr1p-dependent wave. Journal of cell science 127, 1254-1262.

Trcek, T., Larson, D. R., Moldon, A., Query, C. C., and Singer, R. H. (2011). Single-molecule mRNA decay measurements reveal promoter-regulated mRNA stability in yeast. Cell 147, 1484-1497.

Valegard, K., Murray, J. B., Stockley, P. G., Stonehouse, N. J., and Liljas, L. (1994). Crystal structure of an RNA bacteriophage coat protein-operator complex. Nature 371, 623-626.

Valegard, K., Murray, J. B., Stonehouse, N.J., van den Worm, S., Stockley, P. G., and Liljas, L. (1997). The three-dimensional structures of two complexes between recombinant MS2 capsids and RNA operator fragments reveal sequence-specific protein-RNA interactions. Journal of molecular biology 270, 724-738.

Vera, M., Biswas, J., Senecal, A., Singer, R. H., and Park, H. Y. (2016). Single-Cell and Single-Molecule Analysis of Gene Expression Regulation. Annual review of genetics 50, 267-291.

Wu, B., Eliscovich, C., Yoon, Y. J., and Singer, R. H. (2016). Translation dynamics of single mRNAs in live cells and neurons. Science (New York, N.Y. 352, 1430-1435.

Wu, B., Miskolci, V., Sato, H., Tutucci, E., Kenworthy, C. A., Donnelly, S. K., Yoon, Y. J., Cox, D., Singer, R. H., and Hodgson, L. (2015). Synonymous modification results in high-fidelity gene expression of repetitive protein and nucleotide sequences. Genes & development 29, 876-886.

Zenklusen, D., Larson, D. R., and Singer, R. H. (2008). Single-RNA counting reveals alternative modes of gene expression in yeast. Nature structural & molecular biology 15, 1263-1271.

Zid, B. M., and O'Shea, E. K. (2014). Promoter sequences direct cytoplasmic localization and translation of mRNAs during starvation in yeast. Nature 514, 117-121.

Zipor, G., Haim-Vilmovsky, L., Gelin-Licht, R., Gadir, N., Brocard, C., and Gerst, J. E. (2009). Localization of mRNAs coding for peroxisomal proteins in the yeast, *Saccharomyces cerevisiae*. Proceedings of the National Academy of Sciences of the United States of America 106, 19848-19853.

Caponigro, G., Muhlrad, D., and Parker, R. (1993). A small segment of the MAT alpha 1 transcript promotes mRNA decay in *Saccharomyces cerevisiae*: a stimulatory role for rare codons. Molecular and cellular biology 13, 5141-5148.

Chao, J. A., Patskovsky, Y., Almo, S. C., and Singer, R. H. (2008). Structural basis for the coevolution of a viral RNA-protein complex. Nature structural & molecular biology 15, 103-105.

Lionnet, T., Czaplinski, K., Darzacq, X., Shav-Tal, Y., Wells, A. L., Chao, J. A., Park, H. Y., de Turns, V., Lopez-Jones, M., and Singer, R. H. (2011). A transgenic mouse for in vivo detection of endogenous labeled mRNA. Nature methods 8, 165-170.

Mueller, F., Senecal, A., Tantale, K., Marie-Nelly, H., Ly, N., Collin, O., Basyuk, E., Bertrand, E., Darzacq, X., and Zimmer, C. (2013). FISH-quant: automatic counting of transcripts in 3D FISH images. Nature methods 10, 277-278.

Passos, D. O., and Parker, R. (2008). Analysis of cytoplasmic mRNA decay in *Saccharomyces cerevisiae*. Methods in enzymology 448, 409-427.

Trcek, T., Chao, J. A., Larson, D. R., Park, H. Y., Zenklusen, D., Shenoy, S. M., and Singer, R. H. (2012). SinglemRNA counting using fluorescent in situ hybridization in budding yeast. Nature protocols 7, 408-419.

Wu, B., Chao, J. A., and Singer, R. H. (2012). Fluorescence fluctuation spectroscopy enables quantitative imaging of single mRNAs in living cells. Biophysical journal 102, 2936-2944.

Wu, B., Eliscovich, C., Yoon, Y. J., and Singer, R. H. (2016). Translation dynamics of single mRNAs in live cells and neurons. Science (New York, N.Y. 352, 1430-1435).

What is claimed is:

1. A single stranded nucleic acid comprising twelve to twenty four loops of 5'-ANUA-3', wherein the 5' end of each of the loops is directly connected to a sequence of eight nucleotides, seven nucleotides of the sequence of eight nucleotides are complementary to seven nucleotides of a sequence of seven nucleotides directly connected to the 3' end of the same loop, such that a stem and a loop structure is formed in each of the loops, and wherein a stem of each of the loops is separated from a stem of its adjacent loop of the loops by a nucleotide sequence of 40-55 nucleotides.

2. The nucleic acid of claim 1, wherein the nucleic acid, at its 3' portion, further comprises two LoxP sites, optionally separated by a marker gene.

3. The nucleic acid of claim 1, wherein the twelve to twenty four loops of 5'-ANUA-3' are twelve loops of 5'-ANUA-3'.

4. The nucleic acid of claim 1, wherein the nucleotide sequence of 40-55 nucleotides is a nucleotide sequence of 50 nucleotides.

5. The nucleic acid of claim 1, wherein the stem of the stem and loop structure in each of the loops has a different sequence.

6. The nucleic acid of claim 1, wherein the stem of the stem and loop structure in each of the loops has the same sequence.

7. A single stranded nucleic acid encoding from seven to twelve loops of 5'-ANUA-3', wherein the 5' end of each loop is directly connected to a sequence of eight nucleotides, seven nucleotides of the sequence of eight nucleotides are complementary to seven nucleotides of a sequence of seven nucleotides directly connected to the 3' end of the same loop, such that a stem and loop structure is formed in each of the loops, and wherein a stem of each of the loops is separated from a stem of its adjacent loop by a nucleotide sequence of 45-55 nucleotides.

8. A kit comprising the nucleic acid of claim 1, and instructions for use in visualizing an RNA of interest in a cell.

* * * * *

SEQUENCE LISTING

```
<160> NUMBER OF SEQ ID NOS: 39

<210> SEQ ID NO 1

<400> SEQUENCE: 1

000

<210> SEQ ID NO 2
<211> LENGTH: 5330
<212> TYPE: DNA
<213> ORGANISM: Unknown
<220> FEATURE:
<223> OTHER INFORMATION: Description of Unknown: Plasmid sequence

<400> SEQUENCE: 2
tattcttttg atttataagg gattttgccg atttcggcct attggttaaa aaatgagctg      60
atttaacaaa aatttaacgc gaattttaac aaaatattaa cgcttacaat ttccattcgc     120
cattcaggct gcgcaactgt tgggaagggc gatcggtgcg ggcctcttcg ctattacgcc     180
agctggcgaa aggggggatgt gctgcaaggc gattaagttg ggtaacgcca gggttttccc     240
agtcacgacg ttgtaaaacg acggccagtg agcgcgcgta atacgactca ctatagggcg     300
aattggagct ccaccgcggt ggcggccgct ctagaactag tggatcccag agcccctgg      360 caatcgcggg gagacgcagg actaccgcgt cttcactctc gcttgcgcgg tatacgcagg     420
gagcaacgtc acccagggcg acacagagga ataccctgtg tggccccacg gtgctacaaa     480
gaacattccg tattgctcac cagtgtcaca tgtggaggac taccccacaa gcgagtcagg     540
aaaccttcgg ggcatcgcac cattatcccg aacaatcgac acgcaggatt accgcgtggg     600
acactctgtt ccccgtcaaa attggaccat accggagtcg gcttacgtca tgcaggatta     660
ccgcatgcat ggtgcagaat atcggcatgt ctactcgtac agtcaaatct actcgtgtgg     720
tcaggactac cgaccacttc tattctattc atcttttcgg ttgtgcaggt attctgccga     780
tgtacgagaa gacgattacg cttctcgact accttcatca tacatggtgt gcagatggcc     840
gccaagtttt ttgccaatgg aggaataccc cattctctgt caaccaaccc atgcaaagtt     900
tacactctgc tatggcagca ctgtcgcaga ggaatacct gcgagccaaa acggccccg      960 gtgcgtgtat tgcatctgcc ttgcgagcat tcacagggac gaatacgccc tgccgttgca    1020
ttacttcaat atgggtgctc tgtcgtcgtc atcaggacca tttgcgcagg actaccgcgc    1080
atatatcatc agcactcgtg cggatacttc tgggattcct attgttacgc gagctcagga    1140
ataccgagct ctggcgacag agaccctcac acggaagatc tatcgatctc gacaaccctt    1200
aatataactt cgtataatgt atgctatacg aagttattag gtctagagat ctgtttagct    1260
tgcctcgtcc ccgccgggtc acccggccag cgacatggag gcccagaata ccctccttga    1320
cagtcttgac gtgcgcagct caggggcatg atgtgactgt cgcccgtaca tttagcccat    1380
acatccccat gtataatcat ttgcatccat acattttgat ggccgcacgg cgcgaagcaa    1440
aaattacggc tcctcgctgc agacctgcga gcagggaaac gctcccctca cagacgcgtt    1500
```

```
gaattgtccc cacgccgcgc ccctgtagag aaatataaaa ggttaggatt tgccactgag   1560
gttcttcttt catatacttc cttttaaaat cttgctagga tacagttctc acatcacatc   1620
cgaacataaa caaccatggg taaggaaaag actcacgttt cgaggccgcg attaaattcc   1680
aacatggatg ctgatttata tgggtataaa tgggctcgcg ataatgtcgg gcaatcaggt   1740
gcgacaatct atcgattgta tgggaagccc gatgcgccag agttgtttct gaaacatggc   1800
aaaggtagcg ttgccaatga tgttacagat gagatggtca gactaaactg gctgacggaa   1860
tttatgcctc ttccgaccat caagcatttt atccgtactc ctgatgatgc atggttactc   1920
accactgcga tccccggcaa aacagcattc caggtattag aagaatatcc tgattcaggt   1980
gaaaatattg ttgatgcgct ggcagtgttc ctgcgccggt tgcattcgat tcctgtttgt   2040
aattgtcctt ttaacagcga tcgcgtattt cgtctcgctc aggcgcaatc acgaatgaat   2100
aacggtttgg ttgatgcgag tgattttgat gacgagcgta atggctggcc tgttgaacaa   2160
gtctggaaag aaatgcataa gcttttgcca ttctcaccgg attcagtcgt cactcatggt   2220
gatttctcac ttgataacct tattttttgac gaggggaaat taataggttg tattgatgtt   2280
ggacgagtcg gaatcgcaga ccgataccag gatcttgcca tcctatggaa ctgcctcggt   2340
gagttttctc cttcattaca gaacggctt tttcaaaaat atggtattga taatcctgat   2400
atgaataaat tgcagtttca tttgatgctc gatgagtttt tctaatcagt actgacaata   2460
aaaagattct tgttttcaag aacttgtcat ttgtatagtt tttttatatt gtagttgttc   2520
tattttaatc aaatgttagc gtgatttata ttttttttcg cctcgacatc atctgcccag   2580
atgcgaagtt aagtgcgcag aaagtaatat catgcgtcaa tcgtatgtga atgctggtcg   2640
ctatactgct gtcgattcga tactaacgcc gccatccagt gtcgaaaacg agctctcgag   2700 aaccctttaat ataacttcgt ataatgtatg ctatacgaag ttattaggtg atatcagatc   2760
cactagtggc ctatgcggta cccagctttt gttccctta gtgagggtta attgcgcgct   2820
tggcgtaatc atggtcatag ctgtttcctg tgtgaaattg ttatccgctc acaattccac   2880
acaacatacg agccggaagc ataaagtgta aagcctgggg tgcctaatga gtgagctaac   2940
tcacattaat tgcgttgcgc tcactgcccg ctttccagtc gggaaacctg tcgtgccagc   3000
tgcattaatg aatcggccaa cgcgcgggga gaggcggttt gcgtattggg cgctcttccg   3060
cttcctcgct cactgactcg ctgcgctcgg tcgttcggct gcggcgagcg gtatcagctc   3120
actcaaaggc ggtaatacgg ttatccacag aatcagggga taacgcagga aagaacatgt   3180
gagcaaaagg ccagcaaaag gccaggaacc gtaaaaaggc cgcgttgctg gcgttttttcc   3240 ataggctccg ccccctgac gagcatcaca aaaatcgacg ctcaagtcag aggtggcgaa   3300
acccgacagg actataaaga taccaggcgt ttccccctgg aagctccctc gtgcgctctc   3360
ctgttccgac cctgccgctt accggatacc tgtccgcctt tctcccttcg ggaagcgtgg   3420
cgctttctca tagctcacgc tgtaggtatc tcagttcggt gtaggtcgtt cgctccaagc   3480
tgggctgtgt gcacgaaccc cccgttcagc ccgaccgctg cgccttatcc ggtaactatc   3540
gtcttgagtc aacccggta agacacgact tatcgccact ggcagcagcc actggtaaca   3600
ggattagcag agcgaggtat gtaggcggtg ctacagagtt cttgaagtgg tggcctaact   3660
acggctacac tagaaggaca gtatttggta tctgcgctct gctgaagcca gttaccttcg   3720
gaaaaagagt tggtagctct tgatccggca aacaaaccac cgctggtagc ggtggttttt   3780
ttgtttgcaa gcagcagatt acgcgcagaa aaaaaggatc tcaagaagat cctttgatct   3840
tttctacggg gtctgacgct cagtggaacg aaaactcacg ttaagggatt ttggtcatga   3900
```

-continued

```
gattatcaaa aaggatcttc acctagatcc ttttaaatta aaatgaagt tttaaatcaa     3960 tctaaagtat atatgagtaa acttggtctg acagttacca atgcttaatc agtgaggcac    4020
ctatctcagc gatctgtcta tttcgttcat ccatagttgc ctgactcccc gtcgtgtaga    4080
taactacgat acgggagggc ttaccatctg gccccagtgc tgcaatgata ccgcgagacc    4140
cacgctcacc ggctccagat ttatcagcaa taaaccagcc agccggaagg gccgagcgca    4200
gaagtggtcc tgcaacttta tccgcctcca tccagtctat taattgttgc cgggaagcta    4260
gagtaagtag ttcgccagtt aatagtttgc gcaacgttgt tgccattgct acaggcatcg    4320
tggtgtcacg ctcgtcgttt ggtatggctt cattcagctc cggttcccaa cgatcaaggc    4380
gagttacatg atcccccatg ttgtgcaaaa aagcggttag ctccttcggt cctccgatcg    4440
ttgtcagaag taagttggcc gcagtgttat cactcatggt tatggcagca ctgcataatt    4500
ctcttactgt catgccatcc gtaagatgct tttctgtgac tggtgagtac tcaaccaagt    4560
cattctgaga atagtgtatg cggcgaccga gttgctcttg cccggcgtca atacgggata    4620
ataccgcgcc acatagcaga actttaaaag tgctcatcat tggaaaacgt tcttcggggc    4680
gaaaactctc aaggatctta ccgctgttga gatccagttc gatgtaaccc actcgtgcac    4740
ccaactgatc ttcagcatct tttactttca ccagcgtttc tgggtgagca aaaacaggaa    4800
ggcaaaatgc cgcaaaaaag gaataaggg cgacacggaa atgttgaata ctcatactct    4860
tcctttttca atattattga agcatttatc agggttattg tctcatgagc ggatacatat    4920
ttgaatgtat ttagaaaaat aaacaaatag gggttccgcg cacatttccc cgaaaagtgc    4980
cacctgacgc gccctgtagc ggcgcattaa gcgcggcggg tgtggtggtt acgcgcagcg    5040
tgaccgctac acttgccagc gccctagcgc ccgctccttt cgctttcttc ccttcctttc    5100
tcgccacgtt cgccggcttt ccccgtcaag ctctaaatcg ggggctccct ttagggttcc    5160
gatttagtgc tttacggcac ctcgacccca aaaaacttga ttagggtgat ggttcacgta    5220
gtgggccatc gccctgatag acggtttttc gccctttgac gttggagtcc acgttcttta    5280
atagtggact cttgttccaa actggaacaa cactcaaccc tatctcggtc                5330
```

<210> SEQ ID NO 3
<211> LENGTH: 5330
<212> TYPE: DNA
<213> ORGANISM: Unknown
<220> FEATURE:
<223> OTHER INFORMATION: Description of Unknown: Plasmid sequence

<400> SEQUENCE: 3

```
tattcttttg atttataagg gattttgccg atttcggcct attggttaaa aaatgagctg      60
atttaacaaa aatttaacgc gaattttaac aaaatattaa cgcttacaat ttccattcgc     120
cattcaggct gcgcaactgt tgggaagggc gatcggtgcg ggcctcttcg ctattacgcc     180
agctggcgaa agggggatgt gctgcaaggc gattaagttg ggtaacgcca gggttttccc     240
agtcacgacg ttgtaaaacg acggccagtg agcgcgcgta atacgactca ctatagggcg     300
aattggagct ccaccgcggt ggcggccgct ctagaactag tggatcccag agccccctgg     360
caatcgcggg gagacgcagg accaccgcgt cttcactctc gcttgcgcgg tatacgcagg     420
gagcaacgtc acccagggcg acacagagga acaccctgtg tggccccacg gtgctacaaa     480
gaacattccg tattgctcac cagtgtcaca tgtggaggac cacccacaa gcagtcagg      540 aaaccttcgg ggcatcgcac cattatcccg aacaatcgac acgcaggatc accgcgtggg    600
```

```
acactctgtt ccccgtcaaa attggaccat accggagtcg gcttacgtca tgcaggatca    660
ccgcatgcat ggtgcagaat atcggcatgt ctactcgtac agtcaaatct actcgtgtgg    720
tcaggaccac cgaccacttc tattctattc atcttttcgg ttgtgcaggt attctgccga    780
tgtacgagaa gacgatcacg cttctcgact accttcatca tacatggtgt gcagatggcc    840
gccaagtttt ttgccaatgg aggaacaccc cattctctgt caaccaaccc atgcaaagtt    900
tacactctgc tatggcagca ctgtcgcaga ggaacaccct gcgagccaaa acggcccccg    960
gtgcgtgtat tgcatctgcc ttgcgagcat tcacagggac gaacacgccc tgccgttgca   1020
ttacttcaat atgggtgctc tgtcgtcgtc atcaggacca tttgcgcagg accaccgcgc   1080
atatatcatc agcactcgtg cggatacttc tgggattcct attgttacgc gagctcagga   1140
acaccgagct ctggcgacag agaccctcac acggaagatc tatcgatctc gacaacccttt   1200 aatataactt cgtataatgt atgctatacg aagttattag gtctagagat ctgtttagct   1260
tgcctcgtcc ccgccgggtc acccggccag cgacatggag cccagaata ccctccttga    1320 cagtcttgac gtgcgcagct caggggcatg atgtgactgt cgcccgtaca tttagcccat   1380
acatccccat gtataatcat ttgcatccat acattttgat ggccgcacgg cgcgaagcaa   1440
aaattacggc tcctcgctgc agacctgcga gcagggaaac gctcccctca cagacgcgtt   1500
gaattgtccc cacgccgcgc ccctgtagag aaatataaaa ggttaggatt tgccactgag   1560
gttcttcttt catatacttc cttttaaaat cttgctagga tacagttctc acatcacatc   1620
cgaacataaa caaccatggg taaggaaaag actcacgttt cgaggccgcg attaaattcc   1680
aacatggatg ctgatttata tgggtataaa tgggctcgcg ataatgtcgg gcaatcaggt   1740
gcgacaatct atcgattgta tgggaagccc gatgcgccag agttgtttct gaaacatggc   1800
aaaggtagcg ttgccaatga tgttacagat gagatggtca gactaaactg gctgacggaa   1860
tttatgcctc ttccgaccat caagcatttt atccgtactc ctgatgatgc atggttactc   1920
accactgcga tccccggcaa aacagcattc aggtattag aagaatatcc tgattccaggt   1980 gaaaatattg ttgatgcgct ggcagtgttc ctgcgccggt tgcattcgat tcctgtttgt   2040
aattgtcctt ttaacagcga tcgcgtattt cgtctcgctc aggcgcaatc acgaatgaat   2100
aacggtttgg ttgatgcgag tgattttgat gacgagcgta atggctggcc tgttgaacaa   2160
gtctggaaag aaatgcataa gcttttgcca ttctcaccgg attcagtcgt cactcatggt   2220
gatttctcac ttgataacct tatttttgac gaggggaaat taataggttg tattgatgtt   2280
ggacgagtcg gaatcgcaga ccgataccag gatcttgcca tcctatggaa ctgcctcggt   2340
gagttttctc cttcattaca gaaacggctt tttcaaaaat atggtattga taatcctgat   2400
atgaataaat tgcagtttca tttgatgctc gatgagtttt tctaatcagt actgacaata   2460
aaaagattct tgttttcaag aacttgtcat ttgtatagtt tttttatatt gtagttgttc   2520
tattttaatc aaatgttagc gtgatttata tttttttttcg cctcgacatc atctgcccag   2580
atgcgaagtt aagtgcgcag aaagtaatat catgcgtcaa tcgtatgtga atgctggtcg   2640
ctatactgct gtcgattcga tactaacgcc gccatccagt gtcgaaaacg agctctcgag   2700
aacccttaat ataacttcgt ataatgtatg ctatacgaag ttattaggtg atatcagatc   2760
cactagtggc ctatgcggta cccagctttt gttcccttta gtgagggtta attgcgcgct   2820
tggcgtaatc atggtcatag ctgtttcctg tgtgaaattg ttatccgctc acaattccac   2880
acaacatacg agccggaagc ataaagtgta aagcctgggg tgcctaatga gtgagctaac   2940
tcacattaat tgcgttgcgc tcactgcccg ctttccagtc gggaaacctg tcgtgccagc   3000
```

```
tgcattaatg aatcggccaa cgcgcgggga gaggcggttt gcgtattggg cgctcttccg    3060
cttcctcgct cactgactcg ctgcgctcgg tcgttcggct gcggcgagcg gtatcagctc    3120
actcaaaggc ggtaatacgg ttatccacag aatcagggga taacgcagga agaacatgt    3180
gagcaaaagg ccagcaaaag gccaggaacc gtaaaaaggc cgcgttgctg gcgttttcc    3240
ataggctccg cccccctgac gagcatcaca aaaatcgacg ctcaagtcag aggtggcgaa    3300
acccgacagg actataaaga taccaggcgt ttccccctgg aagctccctc gtgcgctctc    3360
ctgttccgac cctgccgctt accggatacc tgtccgcctt tctcccttcg ggaagcgtgg    3420
cgctttctca tagctcacgc tgtaggtatc tcagttcggt gtaggtcgtt cgctccaagc    3480
tgggctgtgt gcacgaaccc cccgttcagc ccgaccgctg cgccttatcc ggtaactatc    3540
gtcttgagtc caacccggta agacacgact tatcgccact ggcagcagcc actggtaaca    3600
ggattagcag agcgaggtat gtaggcggtg ctacagagtt cttgaagtgg tggcctaact    3660
acggctacac tagaaggaca gtatttggta tctgcgctct gctgaagcca gttaccttcg    3720
gaaaaagagt tggtagctct tgatccggca acaaaccac cgctggtagc ggtggttttt    3780
ttgtttgcaa gcagcagatt acgcgcagaa aaaaaggatc tcaagaagat cctttgatct    3840
tttctacggg gtctgacgct cagtggaacg aaaactcacg ttaagggatt ttggtcatga    3900
gattatcaaa aaggatcttc acctagatcc ttttaaatta aaaatgaagt tttaaatcaa    3960
tctaaagtat atatgagtaa acttggtctg acagttacca atgcttaatc agtgaggcac    4020
ctatctcagc gatctgtcta tttcgttcat ccatagttgc ctgactcccc gtcgtgtaga    4080
taactacgat acgggagggc ttaccatctg gccccagtgc tgcaatgata ccgcgagacc    4140
cacgctcacc ggctccagat ttatcagcaa taaaccagcc agccggaagg gccgagcgca    4200
gaagtggtcc tgcaacttta tccgcctcca tccagtctat taattgttgc cgggaagcta    4260
gagtaagtag ttcgccagtt aatagtttgc gcaacgttgt tgccattgct acaggcatcg    4320
tggtgtcacg ctcgtcgttt ggtatggctt cattcagctc cggttcccaa cgatcaaggc    4380
gagttacatg atcccccatg ttgtgcaaaa aagcggttag ctccttcggt cctccgatcg    4440
ttgtcagaag taagttggcc gcagtgttat cactcatggt tatggcagca ctgcataatt    4500
ctcttactgt catgccatcc gtaagatgct tttctgtgac tggtgagtac tcaaccaagt    4560
cattctgaga atagtgtatg cggcgaccga gttgctcttg cccggcgtca atacgggata    4620
ataccgcgcc acatagcaga actttaaaag tgctcatcat tggaaaacgt tcttcggggc    4680
gaaaactctc aaggatctta ccgctgttga tccagttc gatgtaaccc actcgtgcac    4740
ccaactgatc ttcagcatct tttactttca ccagcgtttc tgggtgagca aaaacaggaa    4800
ggcaaaatgc cgcaaaaaag gaataagggc gacacggaa atgttgaata ctcatactct    4860
tcctttttca atattattga agcatttatc agggttattg tctcatgagc ggatacatat    4920
ttgaatgtat ttagaaaaat aaacaaatag gggttccgcg cacatttccc cgaaaagtgc    4980
cacctgacgc gccctgtagc ggcgcattaa gcgcggcggg tgtggtggtt acgcgcagcg    5040
tgaccgctac acttgccagc gccctagcgc ccgctccttt cgctttcttc ccttccttc    5100
tcgccacgtt cgccggcttt ccccgtcaag ctctaaatcg gggctccct ttagggttcc    5160
gatttagtgc tttacggcac ctcgaccca aaaaacttga ttagggtgat ggttcacgta    5220
gtgggccatc gccctgatag acggtttttc gccctttgac gttggagtcc acgttcttta    5280
atagtggact cttgttccaa actggaacaa cactcaaccc tatctcggtc              5330
```

```
<210> SEQ ID NO 4
<211> LENGTH: 8469
<212> TYPE: DNA
<213> ORGANISM: Unknown
<220> FEATURE:
<223> OTHER INFORMATION: Description of Unknown: Plasmid sequence

<400> SEQUENCE: 4
tacgcaaacc gcctctcccc gcgcgttggc cgattcatta atgcagctgg cacgacaggt      60
ttcccgactg gaaagcgggc agtgagcgca acgcaattaa tgtgagttag ctcactcatt     120
aggcacccca ggctttacac tttatgcttc cggctcgtat gttgtgtgga attgtgagcg     180 ataacaatt tcacacagga acagctatg accatgatta cgccaagctt gcatgcctgc      240
agggagcgtt ggttggtgga tcaagcccac gcgtaggcaa tcctcgagca gatccgccgg     300
gcgtgtatat agcgtggatg gccaggcaac tttagtgctg acacatacag gcatatatat     360
atgtgtgcga cgacacatga tcatatggca tgcatgtgct ctgtatgtat ataaaactct     420
tgttttcttc ttttctctaa atattctttc cttatacatt aggtcctttg tagcataaat     480
tactatactt ctatagacac gcaaacacaa atacacacac taaattaata ggatccatgc     540
tagccgttaa aatggcttct aactttactc agttcgttct cgtcgacaat ggcggaactg     600
gcgacgtgac tgtcgcccca agcaacttcg ctaacgggat cgctgaatgg atcagctcta     660
actcgcgttc acaggcttac aaagtaacct gtagcgttcg tcagctctct gcgcagaatc     720
gcaaatacac catcaaagtc gaggtgccta aggcgcctg gcgttcgtac ttaaatatgg     780
aactaaccat tccaatttc gccacgaatt ccgactgcga gcttattgtt aaggcaatgc     840
aaggtctcct aaaagatgga aacccgattc cctcagcaat cgcagcaaac tccggcatct     900
acccaaaaaa aaaagaaaa gttaccggtt ctaaaggtga agaattattc actggtgttg     960
tcccaatttt ggttgaatta gatggtgatg ttaatggtca caaattttct gtctccggtg    1020
aaggtgaagg tgatgctact tacggtaaat tgaccttaaa attatttgt actactggta    1080 aattgccagt tccatggcca accttagtca ctactttaac ttatggtgtt caatgttttt    1140
ctagataccc agatcatatg aaacaacatg acttttcaa gtctgccatg ccagaaggtt    1200
atgttcaaga agaactatt ttttcaaag atgacggtaa ctacaagacc agagctgaag    1260
tcaagtttga aggtgatacc ttagttaata gaatcaaatt aaaaggtatt gattttaaag    1320
aagatggtaa catttaggt cacaaattgg aatacaacta taactctcac aatgtttaca    1380
tcatggctga caacaaaag aatggtatca agttaactt caaaattaga cacaacattg    1440
aagatggttc tgttcaatta gctgaccatt atcaacaaaa tactccaatt ggtgatggtc    1500
cagtcttgtt accagacaac cattacttat ccactcaatc tgccttatcc aaagatccaa    1560
acgaaaagag agaccacatg gtcttgttag aatttgttac tgctgctggt attacccatg    1620
gtatggatga attgtacaaa tgtttaaact ctaaaggtga agaattattc actggtgttg    1680
tcccaatttt ggttgaatta gatggtgatg ttaatggtca caaattttct gtctccggtg    1740
aaggtgaagg tgatgctact tacggtaaat tgaccttaaa attatttgt actactggta    1800 aattgccagt tccatggcca accttagtca ctactttaac ttatggtgtt caatgttttt    1860
ctagataccc agatcatatg aaacaacatg acttttcaa gtctgccatg ccagaaggtt    1920
atgttcaaga agaactatt ttttcaaag atgacggtaa ctacaagacc agagctgaag    1980
tcaagtttga aggtgatacc ttagttaata gaatcgaatt aaaaggtatt gattttaaag    2040
aagatggtaa catttaggt cacaaattgg aatacaacta taactctcac aatgtttaca    2100
```

```
tcatggctga caaacaaaag aatggtatca aagttaactt caaaattaga cacaacattg    2160
aagatggttc tgttcaatta gctgaccatt atcaacaaaa tactccaatt ggtgatggtc    2220
cagtcttgtt accagacaac cattacttat ccactcaatc tgccttatcc aaagatccaa    2280
acgaaaagag agaccacatg gtcttgttag aatttgttac tgctgctggt attacccatg    2340
gtatggatga attgtacaaa taagtttaaa cccgctgatc ctagagggcc gcatcatgta    2400
attagttatg tcacgcttac attcacgccc tccccccaca tccgctctaa ccgaaaagga    2460
aggagttaga caacctgaag tctaggtccc tatttatttt tttatagtta tgttagtatt    2520
aagaacgtta tttatatttc aaattttttct tttttttctg tacagacgcg tgtacgcatg    2580
taacattata ctgaaaacct tgcttgagaa ggttttggga cgctcgaagg ctttaatttg    2640
agctcgaatt cactggccgt cgttttacaa cgtcgtgact gggaaaaccc tggcgttacc    2700
caacttaatc gccttgcagc acatccccct ttcgccagct ggcgtaatag cgaagaggcc    2760
cgcaccgatc gcccttccca acagttgcgc agcctgaatg gcgaatggcg cctgatgcgg    2820
tattttctcc ttacgcatct gtgcggtatt tcacaccgca taatcgctgg gccattctca    2880
tgaagaatat cttgaattta ttgtcatatt actagttggt gtggaagtcc taatatcggt    2940
gatcaatata gtggttgaca tgctggctag tcaacattga gccttttgat catgcaaata    3000
tattacggta ttttacaatc aaatatcaaa cttaactatt gacttataa cttatttagg     3060 tggtaacatt cttataaaaa agaaaaaaat tactgcaaaa cagtactagc ttttaacttg    3120
tatcctaggt tatctatgct gtctcaccat agagaatatt acctatttca gaatgtatgt    3180
ccatgattcg ccgggtaaat acatataata cacaaatctg gcttaataaa gtctataata    3240
tatctcataa agaagtgcta aattggctag tgctatatat ttttaagaaa atttcttttg    3300
actaagtcca tatcgacttt gtaaaagttc acattagcat acatatatta cacgagccag    3360
aaatagtaac ttttgcctaa atcacaaatt gcaaattta attgcttgca aaaggtcaca     3420
tgcttataat caacttttttt aaaaatttaa aatacttttt tatttttat ttttaaacat    3480 aaatgaaata atttatttat tgtttatgat taccgaaaca taaaacctgc tcaagaaaaa    3540
gaaactgttt tgtccttgga aaaaagcac tacctaggag cggccaaaat gccgaggctt     3600
tcatagctta aactctttac agaaaatagg cattatagat cagttcgagt tttcttattc    3660
ttccttccgg ttttatcgtc acagttttac agtaaataag tatcacctct tagagttcga    3720
tgataagctg tcaaacatga gaattaattc cacatgttaa aatagtgaag gagcatgttc    3780
ggcacacagt ggaccgaacg tggggtaagt gcactagggt ccggttaaac ggatctcgca    3840
ttgatgaggc aacgctaatt atcaacatat agattgttat ctatctgcat gaacacgaaa    3900
tctttacttg acgacttgag gctgatggtg tttatgcaaa gaaaccactg tgtttaatat    3960
gtgtcactgt ttgatattac tgtcagcgta gaagataata gtaaagcgg ttaataagtg      4020 tatttgagat aagtgtgata agttttttac agcgaaaaga cgataaatac aagaaaatga    4080
ttacgaggat acggagagag gtatgtacat gtgtatttat atactaagct gccggcggtt    4140
gtttgcaaga ccgagaaaag gctagcaaga atcgggtcat tgtagcgtat gcgcctgtga    4200
acattctctt caacaagttt gattccattg cggtgaaatg gtaaaagtca accccctgcg    4260
atgtatattt tcctgtacaa tcaatcaaaa agccaaatga tttagcatta tctttacatc    4320
ttgttatttt acagatttta tgtttagatc ttttatgctt gcttttcaaa aggcttgcag    4380
gcaagtgcac aaacaatact taaataaata ctactcagta ataacctatt tcttagcatt    4440
```

| | | | | | |
|---|---|---|---|---|---|
| tttgacgaaa | tttgctattt | tgttagagtc | ttttacacca | tttgtctcca | cacctccgct | 4500 |
| tacatcaaca | ccaataacgc | catttaatct | aagcgcatca | ccaacatttt | ctggcgtcag | 4560 |
| tccaccagct | aacataaaat | gtaagctctc | ggggctctct | tgccttccaa | cccagtcaga | 4620 |
| aatcgagttc | caatccaaaa | gttcacctgt | cccacctgct | tctgaatcaa | acaagggaat | 4680 |
| aaacgaatga | ggtttctgtg | aagctgcact | gagtagtatg | ttgcagtctt | ttggaaatac | 4740 |
| gagtctttta | ataactggca | aaccgaggaa | ctcttggtat | tcttgccacg | actcatctcc | 4800 |
| atgcagttgg | acgatcgatg | ataagctgtc | aaacatgaga | attaattcta | ccctatgaac | 4860 |
| atattccatt | ttgtaatttc | gtgtcgtttc | tattatgaat | tcatttata | aagtttatgt | 4920 |
| acaaatatca | taaaaaaaga | gaatctttt | aagcaaggat | tttcttaact | tcttcggcga | 4980 |
| cagcatcacc | gacttcggtg | gtactgttgg | aaccacctaa | atcaccagtt | ctgatacctg | 5040 |
| catccaaaac | ctttttaact | gcatcttcaa | tggccttacc | ttcttcaggc | aagttcaatg | 5100 |
| acaatttcaa | catcattgca | gcagacaaga | tagtggcgat | agggttgacc | ttattctttg | 5160 |
| gcaaatctgg | agcagaaccg | tggcatggtt | cgtacaaacc | aaatgcggtg | ttcttgtctg | 5220 |
| gcaaagaggc | caaggacgca | gatggcaaca | aacccaagga | acctgggata | acggaggctt | 5280 |
| catcggagat | gatatcacca | aacatgttgc | tggtgattat | aataccattt | aggtgggttg | 5340 |
| ggttcttaac | taggatcatg | gcggcagaat | caatcaattg | atgttgaacc | ttcaatgtag | 5400 |
| gaaattcgtt | cttgatggtt | tcctccacag | ttttctcca | taatcttgaa | gaggccaaaa | 5460 |
| cattagcttt | atccaaggac | caaataggca | atggtggctc | atgttgtagg | gccatgaaag | 5520 |
| cggccattct | tgtgattctt | tgcacttctg | gaacggtgta | ttgttcacta | tcccaagcga | 5580 |
| caccatcacc | atcgtcttcc | tttctcttac | caagtaaat | acctcccact | aattctctga | 5640 |
| caacaacgaa | gtcagtacct | ttagcaaatt | gtggcttgat | tggagataag | tctaaaagag | 5700 |
| agtcggatgc | aaagttacat | ggtcttaagt | tggcgtacaa | ttgaagttct | ttacggattt | 5760 |
| ttagtaaacc | ttgttcaggt | ctaacactac | ctgtaccca | tttaggacca | cccacagcac | 5820 |
| ctaacaaaac | ggcatcagcc | ttcttggagg | cttccagcgc | ctcatctgga | agtggaacac | 5880 |
| ctgtagcatc | gatagcagca | ccaccaatta | aatgattttc | gaaatcgaac | ttgacattgg | 5940 |
| aacgaacatc | agaaatagct | ttaagaacct | taatggcttc | ggctgtgatt | tcttgaccaa | 6000 |
| cgtggtcacc | tggcaaaacg | acgatcttct | taggggcaga | cattagaatg | gtatatcctt | 6060 |
| gaaatatata | tatatattgc | tgaaatgtaa | aaggtaagaa | aagttagaaa | gtaagacgat | 6120 |
| tgctaaccac | ctattggaaa | aaacaatagg | tccttaaata | atattgtcaa | cttcaagtat | 6180 |
| tgtgatgcaa | gcatttagtc | atgaacgctt | ctctattcta | tatgaaaagc | cggttccggc | 6240 |
| gctctcacct | ttccttttc | tcccaatttt | tcagttgaaa | aaggtatatg | cgtcaggcga | 6300 |
| cctctgaaat | taacaaaaaa | tttccagtca | tcgaatttga | ttctgtgcga | tagcgcccct | 6360 |
| gtgtgttctc | gttatgttga | ggaaaaaaat | aatggttgct | aagagattcg | aactcttgca | 6420 |
| tcttacgata | cctgagtatt | cccacagtta | attcttgaag | acgaaagggc | ctcgtgatac | 6480 |
| gcctattttt | ataggttaat | gtcatgataa | taatggtttc | ttagacgtca | ggtggcactt | 6540 |
| ttcggggaaa | tgtgcgcgga | acccctattt | gtttattttt | ctaaatacat | tcaaatatgt | 6600 |
| atccgctcat | gagacaataa | ccctgataaa | tgcttcaata | atattgaaaa | aggaagagta | 6660 |
| tgagtattca | acatttccgt | gtcgccctta | ttcccttttt | tgcggcattt | tgccttcctg | 6720 |
| tttttgctca | cccagaaacg | ctggtgaaag | taaaagatgc | tgaagatcag | ttgggtgcac | 6780 |
| gagtgggtta | catcgaactg | gatctcaaca | gcggtaagat | ccttgagagt | tttcgccccg | 6840 |

-continued

| | |
|---|---|
| aagaacgttt tccaatgatg agcactttta aagttctgct atgtggcgcg gtattatccc | 6900 |
| gtattgacgc cgggcaagag caactcggtc gccgcataca ctattctcag aatgacttgg | 6960 |
| ttgagtactc accagtcaca gaaaagcatc ttacggatgg catgacagta agagaattat | 7020 |
| gcagtgctgc cataaccatg agtgataaca ctgcggccaa cttacttctg acaacgatcg | 7080 |
| gaggaccgaa ggagctaacc gcttttttgc acaacatggg ggatcatgta actcgccttg | 7140 |
| atcgttggga accggagctg aatgaagcca taccaaacga cgagcgtgac accacgatgc | 7200 |
| ctgtagcaat ggcaacaacg ttgcgcaaac tattaactgg cgaactactt actctagctt | 7260 |
| cccggcaaca attaatagac tggatggagg cggataaagt tgcaggacca cttctgcgct | 7320 |
| cggcccttcc ggctggctgg tttattgctg ataaatctgg agccggtgag cgtgggtctc | 7380 |
| gcggtatcat tgcagcactg gggccagatg gtaagccctc ccgtatcgta gttatctaca | 7440 |
| cgacggggag tcaggcaact atggatgaac gaaatagaca gatcgctgag ataggtgcct | 7500 |
| cactgattaa gcattggtaa ctgtcagacc aagtttactc atatatactt tagattgatt | 7560 |
| taaaacttca ttttaattt aaaaggatct aggtgaagat cctttttgat aatctcatga | 7620 |
| ccaaaatccc ttaacgtgag ttttcgttcc actgagcgtc agaccccgta gaaaagatca | 7680 |
| aaggatcttc ttgagatcct tttttctgc gcgtaatctg ctgcttgcaa acaaaaaaac | 7740 |
| caccgctacc agcggtggtt tgtttgccgg atcaagagct accaactctt tttccgaagg | 7800 |
| taactggctt cagcagagcg cagataccaa atactgttct tctagtgtag ccgtagttag | 7860 |
| gccaccactt caagaactct gtagcaccgc ctacatacct cgctctgcta atcctgttac | 7920 |
| cagtggctgc tgccagtggc gataagtcgt gtcttaccgg gttggactca agacgatagt | 7980 |
| taccggataa ggcgcagcgg tcgggctgaa cggggggttc gtgcacacag cccagcttgg | 8040 |
| agcgaacgac ctacaccgaa ctgagatacc tacagcgtga gctatgagaa agcgccacgc | 8100 |
| ttcccgaagg gagaaaggcg gacaggtatc cggtaagcgg cagggtcgga acaggagagc | 8160 |
| gcacgaggga gcttccaggg ggaaacgcct ggtatcttta tagtcctgtc gggtttcgcc | 8220 |
| acctctgact tgagcgtcga tttttgtgat gctcgtcagg gggcggagc ctatggaaaa | 8280 |
| acgccagcaa cgcggccttt ttacggttcc tggccttttg ctggcctttt gctcacatgt | 8340 |
| tctttcctgc gttatcccct gattctgtgg ataaccgtat taccgccttt gagtgagctg | 8400 |
| ataccgctcg ccgcagccga acgaccgagc gcagcgagtc agtgagcgag gaagcggaag | 8460 |
| agcgcccaa | 8469 |

<210> SEQ ID NO 5
<211> LENGTH: 19
<212> TYPE: DNA
<213> ORGANISM: Unknown
<220> FEATURE:
<223> OTHER INFORMATION: Description of Unknown: Bacteriophage MS2
      sequence

<400> SEQUENCE: 5
acatgaggat tacccatgt                                                19

<210> SEQ ID NO 6
<211> LENGTH: 19
<212> TYPE: DNA
<213> ORGANISM: Unknown
<220> FEATURE:
<223> OTHER INFORMATION: Description of Unknown: Bacteriophage MS2
      sequence

```
<400> SEQUENCE: 6
acatgaggat cacccatgt                                                  19

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      variant based on Bacteriophage MS2 sequence

<400> SEQUENCE: 7
gacgcaggac taccgcgtc                                                  19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      variant based on Bacteriophage MS2 sequence

<400> SEQUENCE: 8
gacgcaggac caccgcgtc                                                  19

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      variant based on Bacteriophage MS2 sequence

<400> SEQUENCE: 9
cgcagaggaa taccctgcg                                                  19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      variant based on Bacteriophage MS2 sequence

<400> SEQUENCE: 10
cgcagaggaa caccctgcg                                                  19

<210> SEQ ID NO 11
<211> LENGTH: 50
<212> TYPE: DNA
<213> ORGANISM: Drosophila sp.

<400> SEQUENCE: 11
acaaggagag aaatgtacaa ttgtttcgtg ataatgtctc ttattagttg                 50

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      ORP100 PROBE sequence

<400> SEQUENCE: 12
gtctagccgc gaggaagg                                                   18
```

<210> SEQ ID NO 13
<211> LENGTH: 87
<212> TYPE: DNA
<213> ORGANISM: Drosophila sp.

<400> SEQUENCE: 13

```
tgcgaaattg aagggtaccg ttgcttattt tgtaattaca taactgagac agtagagaat    60
tgaaacctac aaacgggtgg aggatca                                        87
```

<210> SEQ ID NO 14
<211> LENGTH: 83
<212> TYPE: DNA
<213> ORGANISM: Drosophila sp.

<400> SEQUENCE: 14

```
tgcgaaattg aagggtaccg ttgcttattt tgtaattaca taactgagac agtagagaat    60
tgaccgctct agaactagtg gat                                            83
```

<210> SEQ ID NO 15
<211> LENGTH: 82
<212> TYPE: DNA
<213> ORGANISM: Drosophila sp.

<400> SEQUENCE: 15

```
tgtacaattg tttcgtgata atgtctctta ttagttgaaa gagattcagt tatccatgta    60
gcataggcca ctagtggatc tg                                             82
```

<210> SEQ ID NO 16
<211> LENGTH: 23
<212> TYPE: DNA
<213> ORGANISM: Drosophila sp.

<400> SEQUENCE: 16

```
aacacataca agatgtttga acg                                            23
```

<210> SEQ ID NO 17
<211> LENGTH: 21
<212> TYPE: DNA
<213> ORGANISM: Brucella abortus

<400> SEQUENCE: 17

```
ctgattgccc gacattatcg c                                              21
```

<210> SEQ ID NO 18
<211> LENGTH: 90
<212> TYPE: DNA
<213> ORGANISM: Unknown
<220> FEATURE:
<223> OTHER INFORMATION: Description of Unknown: Yeast sequence

<400> SEQUENCE: 18

```
gcttgcaaac atcaaaagga gctatgggaa cgtgccaagg tttaaggata ttttcgacga    60
tctctcctaa ccgctctaga actagtggat                                     90
```

<210> SEQ ID NO 19
<211> LENGTH: 92
<212> TYPE: DNA
<213> ORGANISM: Unknown
<220> FEATURE:
<223> OTHER INFORMATION: Description of Unknown: Yeast sequence

<400> SEQUENCE: 19

```
gggcagaaag aattttaaag attatttgct atctagacat tatgtgtttt atatgattgc    60
tgtaaaagta gcataggcca ctagtggatc tg                                 92

<210> SEQ ID NO 20
<211> LENGTH: 20
<212> TYPE: DNA
<213> ORGANISM: Unknown
<220> FEATURE:
<223> OTHER INFORMATION: Description of Unknown: Yeast sequence

<400> SEQUENCE: 20
ggaacgtgcc aaggtttaag                                               20

<210> SEQ ID NO 21
<211> LENGTH: 95
<212> TYPE: DNA
<213> ORGANISM: Homo sapiens

<400> SEQUENCE: 21
cacgatataa gcgaactacc cgaaatgctt tcactgattt tgcgtcaata ctttacagac    60
ctggcatcca gctaacgctc tagaactagt ggatc                              95

<210> SEQ ID NO 22
<211> LENGTH: 98
<212> TYPE: DNA
<213> ORGANISM: Homo sapiens

<400> SEQUENCE: 22 tttttttca gttccatgat ttttttgttc ctttgattcg tgtagtaaac ctcctcttct    60
tggttttcac gatatacact agtggatctg atatcacc                           98

<210> SEQ ID NO 23
<211> LENGTH: 69
<212> TYPE: DNA
<213> ORGANISM: Homo sapiens

<400> SEQUENCE: 23
ttcactgatt ttgcgtcaat actttacaga cctggcatcc agctaagccg ctctagaact    60
agtggatcc                                                           69

<210> SEQ ID NO 24
<211> LENGTH: 69
<212> TYPE: DNA
<213> ORGANISM: Homo sapiens

<400> SEQUENCE: 24
cctttgattc gtgtagtaaa cctcctcttc ttggttttca cgatatagca taggccacta    60
gtggatctg                                                           69

<210> SEQ ID NO 25
<211> LENGTH: 21
<212> TYPE: DNA
<213> ORGANISM: Brucella abortus

<400> SEQUENCE: 25
ctgattgccc gacattatcg c                                             21

<210> SEQ ID NO 26
<211> LENGTH: 22
<212> TYPE: DNA
```

-continued

```
<213> ORGANISM: Homo sapiens

<400> SEQUENCE: 26
gatggtattt gcgaagacca tg                                          22

<210> SEQ ID NO 27
<211> LENGTH: 85
<212> TYPE: DNA
<213> ORGANISM: Unknown
<220> FEATURE:
<223> OTHER INFORMATION: Description of Unknown: Yeast sequence

<400> SEQUENCE: 27
tgctgagcta gaaaatgcta tcatcgtctc taaaccagca ttgggcagct gtctatatga    60
attataagcc cctggcaatc gcggg                                          85

<210> SEQ ID NO 28
<211> LENGTH: 94
<212> TYPE: DNA
<213> ORGANISM: Unknown
<220> FEATURE:
<223> OTHER INFORMATION: Description of Unknown: Yeast sequence

<400> SEQUENCE: 28
ttttgtgatg ctaaagttat gagtagaaaa aaatgagaag ttgttctgaa caaagtaaaa    60
aaaagaagta tacactagtg gatctgatat cacc                                94

<210> SEQ ID NO 29
<211> LENGTH: 94
<212> TYPE: DNA
<213> ORGANISM: Unknown
<220> FEATURE:
<223> OTHER INFORMATION: Description of Unknown: Yeast sequence

<400> SEQUENCE: 29
ttttgtgatg ctaaagttat gagtagaaaa aaatgagaag ttgttctgaa caaagtaaaa    60
aaaagaagta tacactagtg gatctgatat cacc                                94

<210> SEQ ID NO 30
<211> LENGTH: 21
<212> TYPE: DNA
<213> ORGANISM: Unknown
<220> FEATURE:
<223> OTHER INFORMATION: Description of Unknown: Yeast sequence

<400> SEQUENCE: 30
gaagcccttg ccaatgagtt c                                              21

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence:
      probe based on Drosophila

<400> SEQUENCE: 31
gtttcgtgat aatgtctctt attagttg                                       28

<210> SEQ ID NO 32
<211> LENGTH: 8567
<212> TYPE: DNA
<213> ORGANISM: Unknown
<220> FEATURE:
```

<223> OTHER INFORMATION: Description of Unknown: Plasmid sequence

<400> SEQUENCE: 32

```
tacgcaaacc gcctctcccc gcgcgttggc cgattcatta atgcagctgg cacgacaggt      60
ttcccgactg gaaagcgggc agtgagcgca acgcaattaa tgtgagttag ctcactcatt     120
aggcacccca ggctttacac tttatgcttc cggctcgtat gttgtgtgga attgtgagcg     180
gataacaatt tcacacagga acagctatg accatgatta cgccaagctt gcatgcctgc      240
agggagcgtt ggttggtgga tcaagcccac gcgtaggcaa tcctcgagca gatccgccgg     300
gcgtgtatat agcgtggatg gccaggcaac tttagtgctg acacatacag gcatatatat     360
atgtgtgcga cgacacatga tcatatggca tgcatgtgct ctgtatgtat ataaaactct     420
tgttttcttc ttttctctaa atattctttc cttatacatt aggtcctttg tagcataaat     480
tactatactt ctatagacac gcaaacacaa atacacacac taaattaata ggatccatgc     540
tagccgttaa aatggcttct aactttactc agttcgttct cgtcgacaat ggcggaactg     600
gcgacgtgac tgtcgcccca agcaacttcg ctaacgggat cgctgaatgg atcagctcta     660
actcgcgttc acaggcttac aaagtaacct gtagcgttcg tcagagctct gcgcagaatc     720
gcaaatacac catcaaagtc gaggtgccta aaggcgcctg gcgttcgtac ttaaatatgg     780
aactaaccat tccaattttc gccacgaatt ccgactgcga gcttattgtt aaggcaatgc     840
aaggtctcct aaaagatgga aacccgattc cctcagcaat cgcagcaaac tccggcatct     900
acaccggttc taaaggtgaa gaattattca ctggtgttgt cccaattttg gttgaattag     960
atggtgatgt taatggtcac aaattttctg tctccggtga aggtgaaggt gatgctactt    1020
acggtaaatt gaccttaaaa tttatttgta ctactggtaa attgccagtt ccatggccaa    1080
ccttagtcac tactttaact tatggtgttc aatgtttttc tagataccca gatcatatga    1140
aacaacatga cttttcaag tctgccatgc cagaaggtta tgttcaagaa gaactatt       1200
ttttcaaaga tgacggtaac tacaagacca gagctgaagt caagtttgaa ggtgatacct    1260
tagttaatag aatcaaatta aaaggtattg attttaaaga agatggtaac attttaggtc    1320
acaaattgga atacaactat aactctcaca atgtttacat catggctgac aaacaaaaga    1380
atggtatcaa agttaacttc aaaattagac acaacattga agatggttct gttcaattag    1440
ctgaccatta tcaacaaaat actccaattg gtgatggtcc agtcttgtta ccagacaacc    1500
attacttatc cactcaatct gccttatcca aagatccaaa cgaaaagaga gaccacatgg    1560
tcttgttaga atttgttact gctgctggta ttacccatgg tatggatgaa ttgtacaaat    1620
gtttaaactc taaaggtgaa gaattattca ctggtgttgt cccaattttg gttgaattag    1680
atggtgatgt taatggtcac aaattttctg tctccggtga aggtgaaggt gatgctactt    1740
acggtaaatt gaccttaaaa tttatttgta ctactggtaa attgccagtt ccatggccaa    1800
ccttagtcac tactttaact tatggtgttc aatgtttttc tagataccca gatcatatga    1860
aacaacatga cttttcaag tctgccatgc cagaaggtta tgttcaagaa gaactatt       1920
ttttcaaaga tgacggtaac tacaagacca gagctgaagt caagtttgaa ggtgatacct    1980
tagttaatag aatcgaatta aaaggtattg attttaaaga agatggtaac attttaggtc    2040
acaaattgga atacaactat aactctcaca atgtttacat catggctgac aaacaaaaga    2100
atggtatcaa agttaacttc aaaattagac acaacattga agatggttct gttcaattag    2160
ctgaccatta tcaacaaaat actccaattg gtgatggtcc agtcttgtta ccagacaacc    2220
attacttatc cactcaatct gccttatcca aagatccaaa cgaaaagaga gaccacatgg    2280
```

```
tcttgttaga atttgttact gctgctggta ttacccatgg tatggatgaa ttgtacaaat    2340
acccaaaaaa aaaagaaaa gtttaagttt aaacccgctg atcctagagg gccgcatcat    2400
gtaattagtt atgtcacgct tacattcacg ccctccccc acatccgctc taaccgaaaa    2460
ggaaggagtt agacaacctg aagtctaggt ccctatttat ttttttatag ttatgttagt    2520
attaagaacg ttatttatat ttcaaatttt tcttttttt ctgtacagac gcgtgtacgc    2580
atgtaacatt atactgaaaa ccttgcttga aaggttttg gacgctcga aggctttaat    2640 ttgcaagctg cggccctgca ttggcgcgtg tacgcatgta acattatact gaaaaccttg    2700
cttgagaagg ttttgggacg ctcgaaggct taatttgag ctcgaattca ctggccgtcg    2760
ttttacaacg tcgtgactgg gaaaaccctg gcgttaccca acttaatcgc cttgcagcac    2820 atccccttt cgccagctgg cgtaatagcg aagaggcccg caccgatcgc ccttcccaac    2880
agttgcgcag cctgaatggc gaatggcgcc tgatgcggta ttttctcctt acgcatctgt    2940
gcggtatttc acaccgcata atcgctgggc cattctcatg aagaatatct tgaatttatt    3000
gtcatattac tagttggtgt ggaagtccta atatcggtga tcaatatagt ggttgacatg    3060
ctggctagtc aacattgagc cttttgatca tgcaaatata ttacggtatt ttacaatcaa    3120
atatcaaact taactattga cttttataact tatttaggtg gtaacattct tataaaaaag    3180 aaaaaatta ctgcaaaaca gtactagctt ttaacttgta tcctaggtta tctatgctgt    3240
ctcaccatag agaatattac ctatttcaga atgtatgtcc atgattcgcc gggtaaatac    3300
atataataca caaatctggc ttaataaagt ctataatata tctcataaag aagtgctaaa    3360
ttggctagtg ctatatattt ttaagaaaat ttcttttgac taagtccata tcgactttgt    3420
aaaagttcac attagcatac atatattaca cgagccagaa atagtaactt ttgcctaaat    3480
cacaaattgc aaaatttaat tgcttgcaaa aggtcacatg cttataatca acttttttaa    3540
aaatttaaaa tactttttta tttttttattt ttaaacataa atgaaataat ttatttattg    3600
tttatgatta ccgaaacata aaacctgctc aagaaaaaga aactgtttg tccttggaaa    3660 aaaagcacta cctaggagcg gccaaaatgc cgaggctttc atagcttaaa ctctttacag    3720
aaaataggca ttatagatca gttcgagttt tcttattctt ccttccggtt ttatcgtcac    3780
agttttacag taaataagta tcacctctta gagttcgatg ataagctgtc aaacatgaga    3840
attaattcca catgttaaaa tagtgaagga gcatgttcgg cacacagtgg accgaacgtg    3900
gggtaagtgc actagggtcc ggttaaacgg atctcgcatt gatgaggcaa cgctaattat    3960
caacatatag attgttatct atctgcatga acacgaaatc tttacttgac gacttgaggc    4020
tgatggtgtt tatgcaaaga aaccactgtg tttaatatgt gtcactgttt gatattactg    4080
tcagcgtaga agataaatagt aaaagcggtt aataagtgta tttgagataa gtgtgataaa    4140 gttttttacag cgaaaagacg ataaatacaa gaaaatgatt acgaggatac ggagagaggt    4200
atgtacatgt gtatttatat actaagctgc cggcggttgt ttgcaagacc gagaaaaggc    4260
tagcaagaat cgggtcattg tagcgtatgc gcctgtgaac attctcttca acaagtttga    4320
ttccattgcg gtgaaatggt aaaagtcaac cccctgcgat gtatattttc ctgtacaatc    4380
aatcaaaaag ccaaatgatt tagcattatc tttacatctt gttattttac agattttatg    4440
tttagatctt ttatgcttgc ttttcaaaag gcttgcaggc aagtgcacaa acaatactta    4500
aataaatact actcagtaat aacctatttc ttagcatttt tgacgaaatt tgctattttg    4560
ttagagtctt ttacaccatt tgtctccaca cctccgctta catcaacacc aataacgcca    4620
```

-continued

```
tttaatctaa gcgcatcacc aacatttttct ggcgtcagtc caccagctaa cataaaatgt      4680
aagctctcgg ggctctcttg ccttccaacc cagtcagaaa tcgagttcca atccaaaagt      4740
tcacctgtcc cacctgcttc tgaatcaaac aagggaataa acgaatgagg tttctgtgaa      4800
gctgcactga gtagtatgtt gcagtctttt ggaaatacga gtcttttaat aactggcaaa      4860
ccgaggaact cttggtattc ttgccacgac tcatctccat gcagttggac gatcgatgat      4920
aagctgtcaa acatgagaat taattctacc ctatgaacat attccattttt gtaatttcgt     4980 gtcgtttcta ttatgaattt catttataaa gtttatgtac aaatatcata aaaaagaga      5040 atctttttaa gcaaggattt tcttaacttc ttcggcgaca gcatcaccga cttcggtggt      5100
actgttggaa ccacctaaat caccagttct gatacctgca tccaaaacct ttttaactgc      5160
atcttcaatg gccttacctt cttcaggcaa gttcaatgac aatttcaaca tcattgcagc      5220
agacaagata gtggcgatag ggttgacctt attctttggc aaatctggag cagaaccgtg      5280
gcatggttcg tacaaaccaa atgcggtgtt cttgtctggc aaagaggcca aggacgcaga      5340
tggcaacaaa cccaaggaac ctgggataac ggaggcttca tcggagatga tatcaccaaa      5400
catgttgctg gtgattataa taccatttag gtgggttggg ttcttaacta ggatcatggc      5460
ggcagaatca atcaattgat gttgaacctt caatgtagga aattcgttct tgatggtttc      5520
ctccacagtt tttctccata atcttgaaga ggccaaaaca ttagctttat ccaaggacca      5580
aataggcaat ggtggctcat gttgtagggc catgaaagcg gccattcttg tgattctttg      5640
cacttctgga acgtgtatt gttcactatc ccaagcgaca ccatcaccat cgtcttcctt       5700
tctcttacca aagtaaatac ctcccactaa ttctctgaca acaacgaagt cagtaccttt      5760
agcaaattgt ggcttgattg gagataagtc taaagagag tcggatgcaa agttacatgg       5820
tcttaagttg gcgtacaatt gaagttcttt acggattttt agtaaacctt gttcaggtct      5880
aacactacct gtaccccatt taggaccacc cacagcacct aacaaacgg catcagcctt       5940 cttggaggct tccagcgcct catctggaag tggaacacct gtagcatcga tagcagcacc      6000
accaattaaa tgattttcga atcgaactt gacattggaa cgaacatcag aaatagcttt       6060 aagaaccta atggcttcgg ctgtgatttc ttgaccaacg tggtcacctg gcaaaacgac       6120
gatcttctta ggggcagaca ttagaatggt atatccttga aatatatata tatattgctg      6180
aaatgtaaaa ggtaagaaaa gttagaaagt aagacgattg ctaaccaccct attggaaaaa     6240 acaataggtc cttaaataat attgtcaact tcaagtattg tgatgcaagc atttagtcat      6300
gaacgcttct ctattctata tgaaaagccg gttccggcgc tctcacctt cctttttctc       6360 ccaatttttc agttgaaaaa ggtatatgcg tcaggcgacc tctgaaatta acaaaaaatt      6420
tccagtcatc gaatttgatt ctgtgcgata gcgcccctgt gtgttctcgt tatgttgagg      6480
aaaaaaataa tggttgctaa gagattcgaa ctcttgcatc ttacgatacc tgagtattcc      6540
cacagttaat tcttgaagac gaaagggcct cgtgatacgc ctatttttat aggttaatgt      6600
catgataata atggtttctt agacgtcagg tggcacttttt cggggaaatg tgcgcggaac    6660
ccctatttgt ttattttctt aaatacattc aaatatgtat ccgctcatga gacaataacc    6720
ctgataaatg cttcaataat attgaaaaag gaagagtatg agtattcaac atttccgtgt      6780
cgcccttatt ccctttttttg cggcattttg ccttcctgtt tttgctcacc cagaaacgct    6840
ggtgaaagta aaagatgctg aagatcagtt gggtgcacga gtgggttaca tcgaactgga     6900
tctcaacagc ggtaagatcc ttgagagttt tcgccccgaa gaacgttttc caatgatgag     6960
cacttttaaa gttctgctat gtggcgcggt attatcccgt attgacgccg gcaagagca     7020
```

```
actcggtcgc cgcatacact attctcagaa tgacttggtt gagtactcac cagtcacaga    7080
aaagcatctt acggatggca tgacagtaag agaattatgc agtgctgcca taaccatgag    7140
tgataacact gcggccaact tacttctgac aacgatcgga ggaccgaagg agctaaccgc    7200
ttttttgcac aacatggggg atcatgtaac tcgccttgat cgttgggaac cggagctgaa    7260
tgaagccata ccaaacgacg agcgtgacac cacgatgcct gtagcaatgg caacaacgtt    7320
gcgcaaacta ttaactggcg aactacttac tctagcttcc cggcaacaat taatagactg    7380
gatggaggcg gataaagttg caggaccact tctgcgctcg gcccttccgg ctggctggtt    7440
tattgctgat aaatctggag ccggtgagcg tgggtctcgc ggtatcattg cagcactggg    7500
gccagatggt aagccctccc gtatcgtagt tatctacacg acggggagtc aggcaactat    7560
ggatgaacga aatagacaga tcgctgagat aggtgcctca ctgattaagc attggtaact    7620
gtcagaccaa gtttactcat atatacttta gattgattta aaacttcatt tttaatttaa    7680
aaggatctag gtgaagatcc ttttgataa tctcatgacc aaaatccctt aacgtgagtt    7740
ttcgttccac tgagcgtcag accccgtaga aaagatcaaa ggatcttctt gagatccttt    7800
ttttctgcgc gtaatctgct gcttgcaaac aaaaaaacca ccgctaccag cggtggtttg    7860
tttgccggat caagagctac caactctttt tccgaaggta actggcttca gcagagcgca    7920
gataccaaat actgttcttc tagtgtagcc gtagttaggc caccacttca agaactctgt    7980
agcaccgcct acatacctcg ctctgctaat cctgttacca gtggctgctg ccagtggcga    8040
taagtcgtgt cttaccgggt tggactcaag acgatagtta ccggataagg cgcagcggtc    8100
gggctgaacg gggggttcgt gcacacagcc cagcttggag cgaacgacct acaccgaact    8160
gagataccta cagcgtgagc tatgagaaag cgccacgctt cccgaaggga gaaaggcgga    8220
caggtatccg gtaagcggca gggtcggaac aggagagcgc acgagggagc ttccaggggg    8280
aaacgcctgg tatctttata gtcctgtcgg gtttcgccac ctctgacttg agcgtcgatt    8340
tttgtgatgc tcgtcagggg gcggagcct atggaaaaac gccagcaacg cggcctttt     8400
acggttcctg gccttttgct ggccttttgc tcacatgttc tttcctgcgt tatcccctga    8460
ttctgtggat aaccgtatta ccgcctttga gtgagctgat accgctcgcc gcagccgaac    8520
gaccgagcgc agcgagtcag tgagcgagga agcggaagag cgcccaa                  8567
```

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
       artificial sequence based on phage genome

<400> SEQUENCE: 33
acaucaccau uacccaucu                                                  19

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
       artificial sequence based on phage genome

<400> SEQUENCE: 34
acaugaggau cacccaugu                                                  19

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      artificial sequence based on phage genome

<400> SEQUENCE: 35
acaugaggau uacccaugu                                                    19

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      artificial sequence based on phage genome

<400> SEQUENCE: 36
gacgcaggac caccgcguc                                                    19

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
      artificial sequence based on phage genome

<400> SEQUENCE: 37
gacgcaggac uaccgcguc                                                    19

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      artificial sequence based on phage genome

<400> SEQUENCE: 38
cgcagaggaa cacccugcg                                                    19

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      artificial sequence based on phage genome

<400> SEQUENCE: 39
cgcagaggaa uacccugcg                                                    19